(12) United States Patent
Brown et al.

(10) Patent No.: US 11,707,294 B2
(45) Date of Patent: Jul. 25, 2023

(54) MEDICAL DEVICE FOR ACCESSING THE CENTRAL NERVOUS SYSTEM

(71) Applicant: MINNETRONIX NEURO, INC., St. Paul, MN (US)

(72) Inventors: Corey Daniel Brown, Coon Rapids, MN (US); Don William Eldon Evans, St. Paul, MN (US); Philip Jon Haarstad, Chanhassen, MN (US); Brian Dale Nelson, Birchwood, MN (US)

(73) Assignee: MINNETRONIX NEURO, INC., St. Paul, MN (US)

( * ) Notice: Subject to any disclaimer, the term of this patent is extended or adjusted under 35 U.S.C. 154(b) by 183 days.

(21) Appl. No.: 16/277,957

(22) Filed: Feb. 15, 2019

(65) Prior Publication Data

US 2019/0247087 A1 Aug. 15, 2019

Related U.S. Application Data

(60) Provisional application No. 62/734,043, filed on Sep. 20, 2018, provisional application No. 62/703,180, (Continued)

(51) Int. Cl.
*A61B 17/34* (2006.01)
*A61M 25/01* (2006.01)
(Continued)

(52) U.S. Cl.
CPC ...... *A61B 17/3415* (2013.01); *A61B 17/0293* (2013.01); *A61B 17/3431* (2013.01);
(Continued)

(58) Field of Classification Search
CPC ............ A61B 17/3417; A61B 17/3423; A61B 17/0293; A61B 17/3415; A61B 17/3431;
(Continued)

(56) References Cited

U.S. PATENT DOCUMENTS 4,130,113 A    12/1978   Graham
4,355,631 A * 10/1982   LeVahn .............. A61B 17/0293
                                                       600/230
(Continued)

FOREIGN PATENT DOCUMENTS

WO     2007075791 A2    7/2007

OTHER PUBLICATIONS

Kuan et al. "Conceptual Design of a New Neurosurgical Brain Retractor" Mechanisms, Transmissions and Applications, vol. 31: pp. 261-269 Feb. 2015.
(Continued)

*Primary Examiner* — Kathleen S Holwerda
(74) *Attorney, Agent, or Firm* — Seager, Tufte & Wickhem LLP

(57) ABSTRACT

Medical devices for accessing the central nervous system, as well as making and using medical devices, are disclosed. An example medical device may include an expandable access sheath having a proximal end region and a distal end region. The expandable access sheath may be designed to shift between a first configuration and an expanded configuration. The expandable access sheath may include a tubular body having one or more axial support members disposed along the tubular body. The medical device may include an expansion member designed to shift the expandable access sheath between the first configuration and the expanded configuration.

7 Claims, 45 Drawing Sheets

Related U.S. Application Data filed on Jul. 25, 2018, provisional application No. 62/631,339, filed on Feb. 15, 2018.

(51) Int. Cl.
*A61M 25/09* (2006.01)
*A61B 17/02* (2006.01)
*A61M 25/06* (2006.01)

(52) U.S. Cl.
CPC ..... *A61B 17/3439* (2013.01); *A61M 25/0102* (2013.01); *A61M 25/09041* (2013.01); *A61M 25/0662* (2013.01); *A61M 2025/09008* (2013.01); *A61M 2025/09166* (2013.01)

(58) Field of Classification Search
CPC ............ A61B 17/3439; A61B 17/0206; A61B 17/025; A61B 17/1671; A61B 17/1757; A61B 17/7062; A61B 17/7065; A61B 17/7067; A61B 17/8866; A61B 2017/0256; A61B 2090/033; A61B 17/3414; A61M 25/01; A61M 2025/09008; A61M 2025/09166; A61M 25/0102; A61M 25/0662; A61M 25/09041
See application file for complete search history.

(56) References Cited

U.S. PATENT DOCUMENTS

| | | | |
|---|---|---|---|
| 5,580,344 A * | 12/1996 | Hasson | A61B 17/0293 600/201 |
| 5,779,681 A | 7/1998 | Bonn | |
| 6,730,021 B2 | 5/2004 | Vassiliades et al. | |
| 6,923,799 B1 | 8/2005 | Asfora | |
| 7,150,714 B2 | 12/2006 | Myles | |
| 7,182,729 B2 | 2/2007 | Abdelgany et al. | |
| 7,204,840 B2 | 4/2007 | Skakoon et al. | |
| 7,235,084 B2 | 6/2007 | Skakoon et al. | |
| 7,374,534 B2 * | 5/2008 | Dalton | A61B 17/0218 600/222 |
| 7,393,322 B2 | 7/2008 | Wenchell | |
| 7,435,219 B2 | 10/2008 | Kim | |
| 7,473,223 B2 | 1/2009 | Fetzer | |
| 7,481,766 B2 | 1/2009 | Lee et al. | |
| 7,513,869 B2 | 4/2009 | Branch et al. | |
| 7,553,290 B1 | 6/2009 | Asfora | |
| 7,594,888 B2 | 9/2009 | Raymond et al. | |
| 7,645,232 B2 | 1/2010 | Shluzas | |
| 7,691,120 B2 | 4/2010 | Shluzas et al. | |
| 7,694,821 B1 | 4/2010 | Asfora | |
| 7,758,501 B2 | 7/2010 | Frasier et al. | |
| 7,766,823 B2 | 8/2010 | Moll et al. | |
| 7,815,651 B2 | 10/2010 | Skakoon et al. | |
| 7,828,809 B2 | 11/2010 | Skakoon et al. | |
| 7,833,231 B2 | 11/2010 | Skakoon et al. | |
| 7,850,608 B2 | 12/2010 | Hamada | |
| 7,857,820 B2 | 12/2010 | Skakoon et al. | |
| 7,892,174 B2 | 2/2011 | Hestad et al. | |
| 7,896,088 B2 | 3/2011 | Guerrero et al. | |
| 7,931,589 B2 | 4/2011 | Cohen et al. | |
| 7,935,053 B2 | 5/2011 | Karpowicz et al. | |
| 7,981,031 B2 | 7/2011 | Frasier et al. | |
| 8,029,493 B2 | 10/2011 | Asfora | |
| 8,105,236 B2 | 1/2012 | Malandain et al. | |
| 8,123,682 B2 | 2/2012 | Wenchell | |
| 8,152,721 B2 | 4/2012 | Michaeli et al. | |
| 8,291,781 B2 | 10/2012 | Guerrero et al. | |
| 8,328,844 B2 | 12/2012 | Wenchell | |
| 8,343,138 B2 | 1/2013 | Asfora | |
| 8,353,826 B2 | 1/2013 | Weiman | |
| 8,360,970 B2 | 1/2013 | Mangiardi | |
| 8,409,083 B2 | 4/2013 | Mangiardi | |
| 8,409,089 B2 | 4/2013 | Michaeli et al. | |
| 8,454,504 B2 | 6/2013 | Michaeli et al. | |
| 8,517,935 B2 | 8/2013 | Marchek et al. | |
| 8,550,995 B2 | 10/2013 | Frasier et al. | |
| 8,574,154 B2 | 11/2013 | Loftus et al. | |
| 8,579,809 B2 | 11/2013 | Parker | |
| 8,602,984 B2 | 12/2013 | Raymond et al. | |
| 8,608,650 B2 | 12/2013 | Mangiardi | |
| 8,622,897 B2 | 1/2014 | Raymond et al. | |
| 8,663,102 B2 | 3/2014 | Michaeli et al. | |
| 8,733,453 B2 | 5/2014 | Guerrero et al. | |
| 8,845,656 B2 | 9/2014 | Skakoon et al. | |
| 8,876,687 B2 | 11/2014 | Jones et al. | |
| 8,894,573 B2 | 11/2014 | Loftus et al. | |
| 8,911,452 B2 | 12/2014 | Skakoon et al. | |
| 8,956,285 B2 | 2/2015 | Gephart et al. | |
| 8,961,535 B2 | 2/2015 | Burg et al. | |
| 8,974,380 B2 * | 3/2015 | Michaeli | A61B 17/0293 600/222 |
| 8,992,425 B2 | 3/2015 | Karpowicz et al. | |
| 8,992,558 B2 | 3/2015 | Stone et al. | |
| 9,028,402 B2 | 5/2015 | Wenchell | |
| 9,072,501 B2 * | 7/2015 | Menchaca | A61B 17/0293 |
| 9,161,820 B2 | 10/2015 | Mark et al. | |
| 9,169,634 B2 | 10/2015 | Guerrero et al. | |
| 9,179,903 B2 | 11/2015 | Cianfrani et al. | |
| 9,186,175 B2 | 11/2015 | Mark et al. | |
| 9,216,015 B2 | 12/2015 | Wilson | |
| 9,265,523 B2 | 2/2016 | Mark et al. | |
| 9,307,969 B2 | 4/2016 | Novak et al. | |
| 9,386,974 B2 | 7/2016 | Wilson | |
| 9,387,010 B2 | 7/2016 | Mark et al. | |
| 9,492,065 B2 | 11/2016 | Tesar et al. | |
| 9,566,052 B2 | 2/2017 | Novak | |
| 9,579,121 B2 | 2/2017 | Mark et al. | |
| 9,622,777 B2 | 4/2017 | Mark et al. | |
| 9,675,331 B2 | 6/2017 | Mangiardi | |
| 9,675,333 B2 * | 6/2017 | Lauchner | A61B 17/3421 |
| 9,693,761 B2 | 7/2017 | Fedorov et al. | |
| 9,737,287 B2 | 8/2017 | Gifford et al. | |
| 9,757,147 B2 | 9/2017 | Mark et al. | |
| 9,770,261 B2 | 9/2017 | Mark et al. | |
| 9,782,157 B2 | 10/2017 | Novak et al. | |
| 9,848,864 B2 * | 12/2017 | Lauchner | A61B 90/30 |
| 9,855,027 B2 | 1/2018 | Ziolo et al. | |
| 9,949,814 B2 | 4/2018 | Alexander et al. | |
| 9,968,414 B2 | 5/2018 | Wilson | |
| 9,968,415 B2 | 5/2018 | Wilson | |
| 9,980,745 B2 | 5/2018 | Burg et al. | |
| 10,022,520 B2 | 7/2018 | Mark | |
| 10,105,485 B2 | 10/2018 | Piferi et al. | |
| 10,143,366 B2 | 12/2018 | Mark et al. | |
| 10,687,797 B2 * | 6/2020 | Stone | A61B 17/0293 |
| 2005/0165281 A1 * | 7/2005 | Ravikumar | A61B 17/0293 600/204 |
| 2006/0206008 A1 * | 9/2006 | Dalton | A61B 17/0218 600/215 |
| 2006/0206088 A1 | 9/2006 | Lavon | |
| 2006/0271096 A1 * | 11/2006 | Hamada | A61B 17/3439 606/198 |
| 2006/0287583 A1 | 12/2006 | Mangiardi | |
| 2007/0276370 A1 * | 11/2007 | Altarac | A61B 17/1697 606/86 A |
| 2008/0319268 A1 | 12/2008 | Michaeli | |
| 2011/0054405 A1 | 3/2011 | Whiting et al. | |
| 2011/0301421 A1 * | 12/2011 | Michaeli | A61B 17/0293 600/211 |
| 2013/0190575 A1 | 7/2013 | Mast et al. | |
| 2013/0261402 A1 | 10/2013 | Hawkins et al. | |
| 2014/0114138 A1 | 4/2014 | Fedorov et al. | |
| 2015/0223832 A1 | 8/2015 | Swaney et al. | |
| 2016/0128720 A1 | 5/2016 | Mark et al. | |
| 2016/0128722 A1 | 5/2016 | Mark et al. | |
| 2016/0278755 A1 | 9/2016 | Stone | |
| 2016/0317182 A1 | 11/2016 | Mark et al. | |
| 2016/0317795 A1 | 11/2016 | Mark et al. | |
| 2017/0000579 A1 | 1/2017 | Mark et al. | |
| 2017/0215860 A1 | 8/2017 | Trimarche et al. | |
| 2017/0265879 A1 | 9/2017 | Washburn, II et al. | |
| 2017/0265893 A1 | 9/2017 | Mark et al. | |
| 2017/0265894 A1 | 9/2017 | Mark et al. | |

(56) References Cited

U.S. PATENT DOCUMENTS

| | | |
|---|---|---|
| 2017/0333017 A1 | 11/2017 | Gifford et al. |
| 2017/0367731 A1 | 12/2017 | Mark et al. |
| 2018/0125471 A1 | 5/2018 | Schaefer |
| 2018/0125603 A1 | 5/2018 | Cantor et al. |
| 2018/0263660 A1 | 9/2018 | Burg et al. |
| 2018/0296797 A1 | 10/2018 | Mark |
| 2019/0247087 A1 | 8/2019 | Brown et al. |

OTHER PUBLICATIONS

International Search Report and Written Opinion dated May 14, 2019 for International Application No. PCT/US2019/018354.

* cited by examiner

MEDICAL DEVICE FOR ACCESSING THE CENTRAL NERVOUS SYSTEM

CROSS-REFERENCE TO RELATED APPLICATIONS

This application claims the benefit of priority under 35 U.S.C. § 119 of U.S. Provisional Application No. 62/631,339, filed Feb. 15, 2018; U.S. Provisional Application No. 62/703,180, filed Jul. 25, 2018, and U.S. Provisional Application No. 62/734,043, filed Sep. 20, 2018, the entire disclosures of which are hereby incorporated by reference.

TECHNICAL FIELD

The present disclosure pertains to medical devices, and methods for manufacturing medical devices. More particularly, the present disclosure pertains to medical devices for accessing the central nervous system.

BACKGROUND

A wide variety of medical devices have been developed for medical use. Some of these devices include access sheaths, guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A medical device for accessing the central nervous system is disclosed. The medical device comprises: an expandable access sheath having a proximal end region and a distal end region; wherein the expandable access sheath is designed to shift between a first configuration and an expanded configuration; wherein the expandable access sheath includes a tubular body having one or more axial support members disposed along the tubular body; an expansion member designed to shift the expandable access sheath between the first configuration and the expanded configuration.

Alternatively or additionally to any of the embodiments above, the first configuration is a collapsed configuration.

Alternatively or additionally to any of the embodiments above, the expandable access sheath is biased to be in the first configuration.

Alternatively or additionally to any of the embodiments above, the expandable access sheath is designed to be in the first configuration when not subjected to a radially-outward expansion force, expand to the expanded configuration when subjected to the radially-outward expansion force, and return to the first configuration when the radially-outward expansion force is removed.

Alternatively or additionally to any of the embodiments above, the expandable access sheath is designed to be in the first configuration in the absence of the expansion member, expand to the expanded configuration when the expansion member is disposed within the tubular body, and return to the first configuration when the expansion member is removed from the tubular body.

Alternatively or additionally to any of the embodiments above, the one or more axial support members are designed to limit foreshortening of the tubular body.

Alternatively or additionally to any of the embodiments above, the one or more axial support members are designed to fix the length of the tubular body.

Alternatively or additionally to any of the embodiments above, the tubular body has a first length when the expandable access sheath is in the first configuration and wherein the tubular body has a second length when the expandable access sheath is in the expanded configuration.

Alternatively or additionally to any of the embodiments above, the first length is substantially the same as the second length.

Alternatively or additionally to any of the embodiments above, the tubular body includes a polymeric sleeve.

Alternatively or additionally to any of the embodiments above, at least some of the one or more axial support members are substantially straight.

Alternatively or additionally to any of the embodiments above, all of the one or more axial support members are substantially straight.

Alternatively or additionally to any of the embodiments above, at least some of the one or more axial support members have a proximal curved region.

Alternatively or additionally to any of the embodiments above, each of the one or more axial support members have a proximal curved region.

Alternatively or additionally to any of the embodiments above, the one or more axial support members includes a first axial support member and a second axial support member, and further comprising one or more struts extending between the first axial support member and the second axial support member.

Alternatively or additionally to any of the embodiments above, the expansion member includes a trocar.

Alternatively or additionally to any of the embodiments above, the expansion member includes a cannula.

Alternatively or additionally to any of the embodiments above, the expansion member includes a trocar and a cannula.

Alternatively or additionally to any of the embodiments above, the expansion member includes a proximal iris member coupled to the one or more axial support members.

Alternatively or additionally to any of the embodiments above, actuation of the proximal iris member shifts the expandable access sheath from the first configuration to the expanded configuration.

Alternatively or additionally to any of the embodiments above, the expansion member includes a rotatable bolt coupled to the one or more axial support members.

Alternatively or additionally to any of the embodiments above, rotation of the rotatable bolt shifts the expandable access sheath from the first configuration to the expanded configuration.

Alternatively or additionally to any of the embodiments above, at least some of the one or more axial support members includes a curved region, and wherein rotation of the rotatable bolt engages with the rotatable bolt with the curved region.

Alternatively or additionally to any of the embodiments above, engaging the rotatable bolt with the curved region shifts the expandable access sheath from the first configuration to the expanded configuration.

Alternatively or additionally to any of the embodiments above, further comprising a stylet extending at least partially through the expandable access sheath.

Alternatively or additionally to any of the embodiments above, the expandable access sheath is in the first configuration when the stylet extends at least partially through the expandable access sheath.

Alternatively or additionally to any of the embodiments above, the stylet includes a distal camera.

Alternatively or additionally to any of the embodiments above, the stylet includes one or more marker members or sensors.

Alternatively or additionally to any of the embodiments above, at least some of the one or more marker members include visual markers.

Alternatively or additionally to any of the embodiments above, at least some of the one or more marker members include markers that detectable by fluoroscopic imaging.

Alternatively or additionally to any of the embodiments above, at least some of the one or more marker members include markers that detectable by magnetic resonance imaging.

Alternatively or additionally to any of the embodiments above, at least some of the one or more marker members include markers that detectable by optical coherence tomography imaging.

Alternatively or additionally to any of the embodiments above, further comprising a device orienting assembly coupled to the expandable access sheath.

Alternatively or additionally to any of the embodiments above, the device orienting assembly includes a base designed to engage a patient.

Alternatively or additionally to any of the embodiments above, the device orienting assembly includes one or more adjustable legs designed to engage a patient.

Alternatively or additionally to any of the embodiments above, the device orienting assembly includes a stylet.

Alternatively or additionally to any of the embodiments above, further comprising a locking arm coupled to the device orienting assembly.

Alternatively or additionally to any of the embodiments above, the device orienting assembly includes a base and an adjustable member coupled to the base.

Alternatively or additionally to any of the embodiments above, the adjustable member is axially adjustable relative to the base.

Alternatively or additionally to any of the embodiments above, the adjustable member is pivotably adjustable relative to the base.

A medical device for accessing a target region within the brain is disclosed. The medical device comprises: an expandable brain port designed to reversibly shift between a first configuration and an expanded configuration; wherein the expandable brain port includes a polymeric sleeve and a stent-like lattice coupled to the polymeric sleeve, wherein the stent-like lattice includes one or more axial support members; an expansion member designed to shift the expandable brain port between the first configuration and the expanded configuration.

Alternatively or additionally to any of the embodiments above, the first configuration is a collapsed configuration.

Alternatively or additionally to any of the embodiments above, the expandable brain port is biased to be in the first configuration.

Alternatively or additionally to any of the embodiments above, the expandable brain port is designed to be in the first configuration when not subjected to a radially-outward expansion force, expand to the expanded configuration when subjected to the radially-outward expansion force, and return to the first configuration when the radially-outward expansion force is removed.

Alternatively or additionally to any of the embodiments above, the expandable brain port is designed to be in the first configuration in the absence of the expansion member, expand to the expanded configuration when the expansion member is disposed within the expandable brain port, and return to the first configuration when the expansion member is removed from the expandable brain port.

Alternatively or additionally to any of the embodiments above, the one or more axial support members are designed to limit foreshortening of the expandable brain port.

Alternatively or additionally to any of the embodiments above, the one or more axial support members are designed to fix the length of the expandable brain port.

Alternatively or additionally to any of the embodiments above, the expandable brain port has a first length when the expandable brain port is in the first configuration and wherein the expandable brain port has a second length when the expandable brain port is in the expanded configuration.

Alternatively or additionally to any of the embodiments above, the first length is substantially the same as the second length.

Alternatively or additionally to any of the embodiments above, at least some of the one or more axial support members are substantially straight.

Alternatively or additionally to any of the embodiments above, all of the one or more axial support members are substantially straight.

Alternatively or additionally to any of the embodiments above, at least some of the one or more axial support members have a proximal curved region.

Alternatively or additionally to any of the embodiments above, each of the one or more axial support members have a proximal curved region.

Alternatively or additionally to any of the embodiments above, the one or more axial support members includes a first axial support member and a second axial support member, and further comprising one or more struts extending between the first axial support member and the second axial support member.

Alternatively or additionally to any of the embodiments above, the expansion member includes a trocar.

Alternatively or additionally to any of the embodiments above, the expansion member includes a cannula.

Alternatively or additionally to any of the embodiments above, the expansion member includes a trocar and a cannula.

Alternatively or additionally to any of the embodiments above, the expansion member includes a proximal iris member coupled to the one or more axial support members.

Alternatively or additionally to any of the embodiments above, actuation of the proximal iris member shifts the expandable brain port from the first configuration to the expanded configuration.

Alternatively or additionally to any of the embodiments above, the expansion member includes a rotatable bolt coupled to the one or more axial support members.

Alternatively or additionally to any of the embodiments above, rotation of the rotatable bolt shifts the expandable brain port from the first configuration to the expanded configuration.

Alternatively or additionally to any of the embodiments above, at least some of the one or more axial support members includes a curved region, and wherein rotation of the rotatable bolt engages with the rotatable bolt with the curved region.

Alternatively or additionally to any of the embodiments above, engaging the rotatable bolt with the curved region shifts the expandable brain port from the first configuration to the expanded configuration.

Alternatively or additionally to any of the embodiments above, further comprising a stylet extending at least partially through the expandable brain port.

Alternatively or additionally to any of the embodiments above, the expandable brain port is in the first configuration when the stylet extends at least partially through the expandable brain port.

Alternatively or additionally to any of the embodiments above, the stylet includes a distal camera.

Alternatively or additionally to any of the embodiments above, the stylet includes one or more marker members or sensors.

Alternatively or additionally to any of the embodiments above, at least some of the one or more marker members include visual markers.

Alternatively or additionally to any of the embodiments above, at least some of the one or more marker members include markers that detectable by fluoroscopic imaging.

Alternatively or additionally to any of the embodiments above, at least some of the one or more marker members include markers that detectable by magnetic resonance imaging.

Alternatively or additionally to any of the embodiments above, at least some of the one or more marker members include markers that detectable by optical coherence tomography imaging.

Alternatively or additionally to any of the embodiments above, further comprising a device orienting assembly coupled to the expandable brain port.

Alternatively or additionally to any of the embodiments above, the device orienting assembly includes a base designed to engage a patient.

Alternatively or additionally to any of the embodiments above, the device orienting assembly includes one or more adjustable legs designed to engage a patient.

Alternatively or additionally to any of the embodiments above, the device orienting assembly includes a stylet.

Alternatively or additionally to any of the embodiments above, further comprising a locking arm coupled to the device orienting assembly.

Alternatively or additionally to any of the embodiments above, the device orienting assembly includes a base and an adjustable member coupled to the base.

Alternatively or additionally to any of the embodiments above, the adjustable member is axially adjustable relative to the base.

Alternatively or additionally to any of the embodiments above, the adjustable member is pivotably adjustable relative to the base.

A method for accessing a target region is disclosed. The method comprises: advancing an expandable access sheath through a body tissue to a position adjacent to a target region in the central nervous system; and advancing an expansion member through the expandable access sheath to shift the expandable access sheath from a first configuration to an expanded configuration.

Alternatively or additionally to any of the embodiments above, a stylet is disposed within the expandable access sheath, and wherein advancing an expandable access sheath through a body tissue to a position adjacent to a target region in the central nervous system includes advancing the expandable access sheath and the stylet to the position adjacent to the target region.

Alternatively or additionally to any of the embodiments above, when the stylet is disposed within the expandable access sheath, the expandable access sheath is in the first configuration.

Alternatively or additionally to any of the embodiments above, further comprising removing the stylet from the expandable access sheath.

Alternatively or additionally to any of the embodiments above, further comprising securing the expandable access sheath to a device orienting assembly.

Alternatively or additionally to any of the embodiments above, further comprising adjusting the axial position of the expandable access sheath relative to the device orienting assembly.

Alternatively or additionally to any of the embodiments above, further comprising advancing a medical device at least partially through the expandable access sheath while the expandable access sheath is in the expanded configuration.

A method for accessing a target region is disclosed. The method comprises: advancing an expandable brain port through a body tissue to a position adjacent to a target region in the brain; and advancing an expansion member through the expandable brain port to shift the expandable brain port from a first configuration to an expanded configuration.

Alternatively or additionally to any of the embodiments above, a stylet is disposed within the expandable brain port, and wherein advancing an expandable brain port through a body tissue to a position adjacent to a target region in the brain includes advancing the expandable brain port and the imaging de stylet vice to the position adjacent to the target region.

Alternatively or additionally to any of the embodiments above, when the stylet is disposed within the expandable brain port, the expandable brain port is in the first configuration.

Alternatively or additionally to any of the embodiments above, further comprising removing the stylet from the expandable access sheath.

Alternatively or additionally to any of the embodiments above, further comprising securing the expandable brain port to a device orienting assembly.

Alternatively or additionally to any of the embodiments above, further comprising adjusting the axial position of the expandable brain port relative to the device orienting assembly.

Alternatively or additionally to any of the embodiments above, further comprising advancing a medical device at least partially through the expandable brain port while the expandable brain port is in the expanded configuration.

A medical device for accessing the central nervous system is disclosed. The medical device comprises: an expandable access sheath including a plurality of axially-extending support members; wherein the expandable access sheath is designed to shift between a first configuration and an expanded configuration; wherein each of the axially-extending support bars includes a distal end region and a curved proximal end region; a hub disposed adjacent to the curved proximal end region, the hub including a first thread; a bolt coupled to the hub, the bolt including a second thread designed to be threadably engaged with the first thread; and wherein rotation of the bolt cause the bolt to engage the curved proximal end regions of the axially-extending support bars and shift the expandable access sheath from the first configuration toward the expanded configuration.

An expandable access port is disclosed. The expandable access port comprises: a housing having a plurality of tines coupled thereto, the plurality of tines including a first tine; an actuation member coupled to the housing, the actuation member being designed to shift the plurality of tines between a first configuration and an expanded configuration; and a nose cone coupled to the first tine.

Alternatively or additionally to any of the embodiments above, the housing includes a threaded region.

Alternatively or additionally to any of the embodiments above, the actuation member includes a nut threadably engaged with the threaded region.

Alternatively or additionally to any of the embodiments above, at least one of the plurality of tines is secured to the housing with a pivot member.

Alternatively or additionally to any of the embodiments above, the pivot member includes a pivot pin.

Alternatively or additionally to any of the embodiments above, at least one of the plurality of tines includes a proximal end region with an angled surface.

Alternatively or additionally to any of the embodiments above, the actuation member includes an actuation surface designed to engage the angled surface.

Alternatively or additionally to any of the embodiments above, further comprising a sleeve extending along at least some of the plurality of tines.

Alternatively or additionally to any of the embodiments above, the sleeve extends along an outer surface of each of the plurality of tines.

Alternatively or additionally to any of the embodiments above, the sleeve includes an elastomeric material.

Alternatively or additionally to any of the embodiments above, at least one of the plurality of tines includes a gripping region designed to engage the sleeve.

Alternatively or additionally to any of the embodiments above, the housing defines a central axis and wherein the nose cone is aligned with the central axis when the plurality of tines are in the first configuration.

Alternatively or additionally to any of the embodiments above, the housing defines a central axis and wherein the nose cone is radially offset from the central axis when the plurality of tines are in the expanded configuration.

Alternatively or additionally to any of the embodiments above, the housing has a proximal opening formed therein and wherein the plurality of tines define a distal opening.

Alternatively or additionally to any of the embodiments above, the distal opening has substantially the same width or a smaller width than the proximal opening when the plurality of tines are in the first configuration.

Alternatively or additionally to any of the embodiments above, the distal opening has substantially the same width or a larger width than the proximal opening when the plurality of tines are in the expanded configuration.

Alternatively or additionally to any of the embodiments above, further comprising one or more stabilization members coupled to the housing.

Alternatively or additionally to any of the embodiments above, the one or more stabilization members are designed to axially translate relative to the housing.

Alternatively or additionally to any of the embodiments above, the one or more stabilization members includes a stabilizing bar extending radially from the housing.

An expandable access port is disclosed. The expandable access port comprises: a housing having an expandable conduit coupled thereto, the expandable conduit including a plurality of tines, the plurality of tines including a first tine; an actuation member coupled to the housing, the actuation member being designed to shift the expandable conduit between a first configuration and an expanded configuration; and a nose cone coupled to the first tine.

Alternatively or additionally to any of the embodiments above, the housing includes a threaded region.

Alternatively or additionally to any of the embodiments above, the actuation member includes a nut threadably engaged with the threaded region.

Alternatively or additionally to any of the embodiments above, the first tine is secured to the housing with a pivot member.

Alternatively or additionally to any of the embodiments above, the pivot member includes a pivot pin.

Alternatively or additionally to any of the embodiments above, the first tine includes a proximal end region with an angled surface.

Alternatively or additionally to any of the embodiments above, the actuation member includes an actuation surface designed to engage the angled surface.

Alternatively or additionally to any of the embodiments above, the expandable conduit includes a sleeve extending along at least some of the plurality of tines.

Alternatively or additionally to any of the embodiments above, the sleeve extends along an outer surface of the first tine.

Alternatively or additionally to any of the embodiments above, the sleeve includes an elastomeric material.

Alternatively or additionally to any of the embodiments above, the first tine includes a gripping region designed to engage the sleeve.

Alternatively or additionally to any of the embodiments above, the housing defines a central axis and wherein the nose cone is aligned with the central axis when the expandable conduit in the first configuration.

Alternatively or additionally to any of the embodiments above, the housing defines a central axis and wherein the nose cone is radially offset from the central axis when the expandable conduit in the expanded configuration.

Alternatively or additionally to any of the embodiments above, the housing has a proximal opening formed therein and wherein the expandable conduit defines a distal opening.

Alternatively or additionally to any of the embodiments above, the distal opening has substantially the same width or a smaller width than the proximal opening when the expandable conduit is the first configuration.

Alternatively or additionally to any of the embodiments above, the distal opening has substantially the same width or a larger width than the proximal opening when the expandable conduit is in the expanded configuration.

Alternatively or additionally to any of the embodiments above, further comprising one or more stabilization members coupled to the housing.

Alternatively or additionally to any of the embodiments above, the one or more stabilization members are designed to axially translate relative to the housing.

Alternatively or additionally to any of the embodiments above, the one or more stabilization members includes a stabilizing bar extending radially from the housing.

A system for accessing the central nervous system is disclosed. The system comprises: an expandable access port, the expandable access port comprising: a housing having a plurality of tines coupled thereto, the plurality of tines including a first tine, and an actuation member coupled to the housing, the actuation member being designed to shift the plurality of tines between a first configuration and an expanded configuration; and a holder designed to extend through the housing, the holder comprising: a tubular base, a shaft extending from the tubular base, and a nose cone attached to the shaft.

Alternatively or additionally to any of the embodiments above, the housing includes a threaded region.

Alternatively or additionally to any of the embodiments above, the actuation member includes a nut threadably engaged with the threaded region.

Alternatively or additionally to any of the embodiments above, at least one of the plurality of tines is secured to the housing with a pivot member.

Alternatively or additionally to any of the embodiments above, the pivot member includes a pivot pin.

Alternatively or additionally to any of the embodiments above, at least one of the plurality of tines includes a proximal end region with an angled surface.

Alternatively or additionally to any of the embodiments above, the actuation member includes an actuation surface designed to engage the angled surface.

Alternatively or additionally to any of the embodiments above, further comprising a sleeve extending along at least some of the plurality of tines.

Alternatively or additionally to any of the embodiments above, the sleeve extends along an outer surface of each of the plurality of tines.

Alternatively or additionally to any of the embodiments above, the sleeve includes an elastomeric material.

Alternatively or additionally to any of the embodiments above, at least one of the plurality of tines includes a gripping region designed to engage the sleeve.

Alternatively or additionally to any of the embodiments above, the housing defines a central axis and wherein the nose cone is aligned with the central axis when the plurality of tines are in the first configuration.

Alternatively or additionally to any of the embodiments above, the housing defines a central axis and wherein the nose cone is radially offset from the central axis when the plurality of tines are in the expanded configuration.

Alternatively or additionally to any of the embodiments above, the housing has a proximal opening formed therein and wherein the plurality of tines define a distal opening.

Alternatively or additionally to any of the embodiments above, the distal opening has substantially the same width or a smaller width than the proximal opening when the plurality of tines are in the first configuration.

Alternatively or additionally to any of the embodiments above, the distal opening has substantially the same width or a larger width than the proximal opening when the plurality of tines are in the expanded configuration.

Alternatively or additionally to any of the embodiments above, further comprising one or more stabilization members coupled to the housing.

Alternatively or additionally to any of the embodiments above, the one or more stabilization members are designed to axially translate relative to the housing.

Alternatively or additionally to any of the embodiments above, the one or more stabilization members includes a stabilizing bar extending radially from the housing.

Alternatively or additionally to any of the embodiments above, the holder includes a proximal flange.

Alternatively or additionally to any of the embodiments above, the nose cone has a tapered proximal end region.

Alternatively or additionally to any of the embodiments above, the nose cone has a tapered distal end region.

A system for accessing the central nervous system is disclosed. The system comprises: an expandable access port, the expandable access port comprising: a housing having an expandable conduit coupled thereto, the expandable conduit including a plurality of tines, the plurality of tines including a first tine, and an actuation member coupled to the housing, the actuation member being designed to shift the expandable conduit between a first configuration and an expanded configuration; and a holder designed to extend at least partially through the expandable conduit, the holder comprising: a tubular base, a shaft extending from the tubular base, and a nose cone attached to the shaft.

Alternatively or additionally to any of the embodiments above, the housing includes a threaded region.

Alternatively or additionally to any of the embodiments above, the actuation member includes a nut threadably engaged with the threaded region.

Alternatively or additionally to any of the embodiments above, the first tine is secured to the housing with a pivot member.

Alternatively or additionally to any of the embodiments above, the pivot member includes a pivot pin.

Alternatively or additionally to any of the embodiments above, the first tine includes a proximal end region with an angled surface.

Alternatively or additionally to any of the embodiments above, the actuation member includes an actuation surface designed to engage the angled surface.

Alternatively or additionally to any of the embodiments above, the expandable conduit includes a sleeve extending along at least some of the plurality of tines.

Alternatively or additionally to any of the embodiments above, the sleeve extends along an outer surface of the first tine.

Alternatively or additionally to any of the embodiments above, the sleeve includes an elastomeric material.

Alternatively or additionally to any of the embodiments above, the first tine includes a gripping region designed to engage the sleeve.

Alternatively or additionally to any of the embodiments above, the housing defines a central axis and wherein the nose cone is aligned with the central axis when the expandable conduit in the first configuration.

Alternatively or additionally to any of the embodiments above, the housing defines a central axis and wherein the nose cone is radially offset from the central axis when the expandable conduit in the expanded configuration.

Alternatively or additionally to any of the embodiments above, the housing has a proximal opening formed therein and wherein the expandable conduit defines a distal opening.

Alternatively or additionally to any of the embodiments above, the distal opening has substantially the same width or a smaller width than the proximal opening when the expandable conduit is the first configuration.

Alternatively or additionally to any of the embodiments above, the distal opening has substantially the same width or a larger width than the proximal opening when the expandable conduit is in the expanded configuration.

Alternatively or additionally to any of the embodiments above, further comprising one or more stabilization members coupled to the housing.

Alternatively or additionally to any of the embodiments above, the one or more stabilization members are designed to axially translate relative to the housing.

Alternatively or additionally to any of the embodiments above, the one or more stabilization members includes a stabilizing bar extending radially from the housing.

Alternatively or additionally to any of the embodiments above, the holder includes a proximal flange.

Alternatively or additionally to any of the embodiments above, the nose cone has a tapered proximal end region.

Alternatively or additionally to any of the embodiments above, the nose cone has a tapered distal end region.

An expandable access port is disclosed. The expandable access port comprises: a housing having an expandable conduit coupled thereto, the expandable conduit including a plurality of tines and a sleeve coupled to the plurality of tines; an actuation member coupled to the housing, the actuation member being designed to shift the expandable conduit between a first configuration and an expanded configuration; and a cap coupled to the housing, the cap including an attachment region designed to have an adjustment mechanism releasable attached thereto.

Alternatively or additionally to any of the embodiments above, further comprising the adjustment mechanism releasable coupled to the attachment region.

Alternatively or additionally to any of the embodiments above, the cap further comprises a second attachment region, and further comprising a second adjustment mechanism releasable coupled to the second attachment region.

Alternatively or additionally to any of the embodiments above, the adjustment mechanism includes a set screw.

Alternatively or additionally to any of the embodiments above, the adjustment mechanism includes a stabilizing bar.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1A:
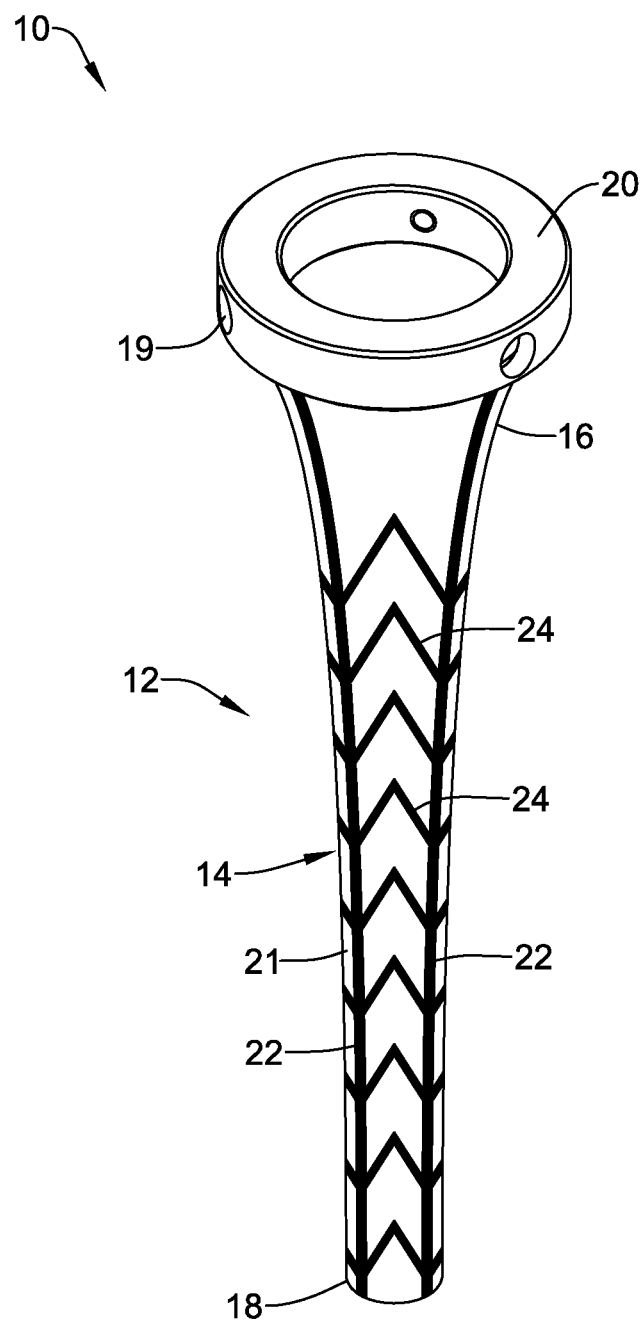
FIG. 1A is a perspective view of a portion of an example medical device and depicts an example expandable access sheath.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Lesions, clots, tumors, and/or other malformations in the brain may be challenging to treat. At least some of the challenges associated with such treatments may be associated with gaining access to the target side. For example, accessing a clot within the brain may require navigating a treatment device through regions of the brain. This may require relatively delicate traversal through brain tissue. It may be desirable to access regions of the brain in a manner that reduces trauma to the brain tissue, increases the ability to image/visualize regions of the brain, and/or otherwise provides better access to a target region. Disclosed herein are medical devices that are designed to provide improved access to body regions including regions along the central nervous system and/or the brain. Also disclosed are methods for making and using such devices.

FIG. 1A is a perspective view of a portion of an example medical device 10 for accessing the central nervous system. In this example, an example expandable access sheath 12 is depicted. In general, the expandable access sheath 12 may be designed to be inserted into a body opening, cavity, or the like in order to provide access to a target region. For example, the expandable access sheath 12 may be designed to be inserted through an opening in the head of a patient, through the skull, and into the brain so as to provide access to a target (e.g., a lesion, clot, tumor, or the like, etc.) within the brain. Furthermore, due to the expandable access sheath 12 being "expandable", the expandable access sheath 12 can be placed near a target site (e.g., within the brain) and expanded. When doing so, the expandable access sheath 12 may atraumatically push, move, and/or otherwise expand brain tissue adjacent to the target site, which may provide for better access, visualization (e.g. including direct visualization by a clinician through the expandable access sheath 12), etc. of the target site.

The expandable access sheath 12 may include a tubular body 14 having a proximal end region 16 and a distal end region 18. A hub or flange 20 may be disposed at the proximal end region 16. The hub 20 may have a variety of shapes and/or configurations. In some instances, the hub 20 may include one or more openings 19 that may be used to secure the expandable access sheath 12 to another component of the medical device 10 and/or a part of a medical device system (e.g., a system including the medical device 10). For example, the openings 19 may have a size or shape (e.g., which may include a thread, a tapered or narrowed shape, etc.) designed to engage a fastener or set screw.

The tubular body 14 of the expandable access sheath 12 may include a sheath or sleeve 21. In some instances, the sleeve 21 may include a polymeric or silicone material. The material of the sleeve 21 may elastic and/or resilient in nature, which may allow for appropriate expansion and/or contraction as desired without significant plastic deformation. Some example of polymeric materials that may be used for the sleeve, or other components of the sheath 12 are given below. Other materials are contemplated. One or more axial support members 22 may be disposed along, coupled to, or embedded in the sleeve 21. The axial support members 22 may take the form of rods or wires. The axial support members 22 may have a circular cross-sectional shape or a non-circular cross-sectional shape, e.g. rectangular, square, or other polygon. The expandable access sheath 12 may include 1, 2, 3, 4, 5, 6, 7, 8, or more axial support members 22. In some instances, one or more struts 24 may extend between adjacent axial support members 22. The struts 24 may be substantially straight or may include one or more bends or turns. In some instances, the axial support members 22 and struts 24 may resemble or otherwise form a stent-like lattice or configuration. Additionally, the sleeve 21 and/or one or more axial support members 22 may be made of and/or include an elastic and/or resilient and/or superelastic material that may provide a biasing force into a closed configuration—for example as discussed relative to one example use of the sheath 12 below.

Figure 1B:
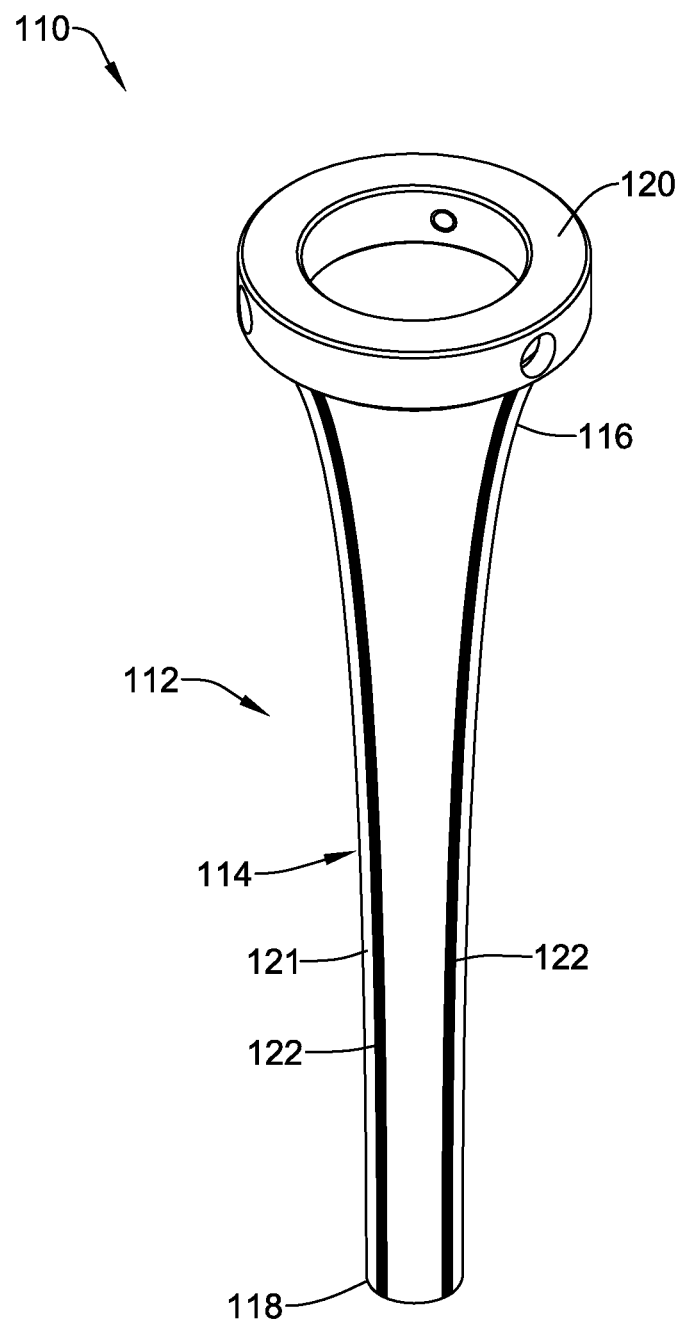
FIG. 1B is a perspective view of a portion of an example medical device and depicts an example expandable access sheath.

FIG. 1B is a perspective view of a portion of another example medical device 110 for accessing the central nervous system. The example medical device 110 may resemble the medical device 10 in form and function such that attributes of the device 10 may be applied, as appropriate, to the device 110. In this example, another example expandable access sheath 112 is depicted. The expandable access sheath 112 may include a tubular body 114 having a proximal end region 116 and a distal end region 118. A hub or flange 120 may be disposed at the proximal end region 116. The tubular body 114 of the expandable access sheath 112 may include a sheath or sleeve 121. One or more axial support members 122 may be disposed along, coupled to, or embedded in the sleeve 121. Unlike the expandable access sheath 12 depicted in FIG. 1A, the expandable access sheath 112 may lack struts (e.g., similar to struts 24) extending between the axial support members 122. Additionally, the sleeve 121 and/or one or more axial support members 122 may be made of and/or include an elastic and/or resilient and/or superelastic material that may provide a biasing force into a closed configuration—for example as discussed relative to the sheath 12 below.

Figure 1C:
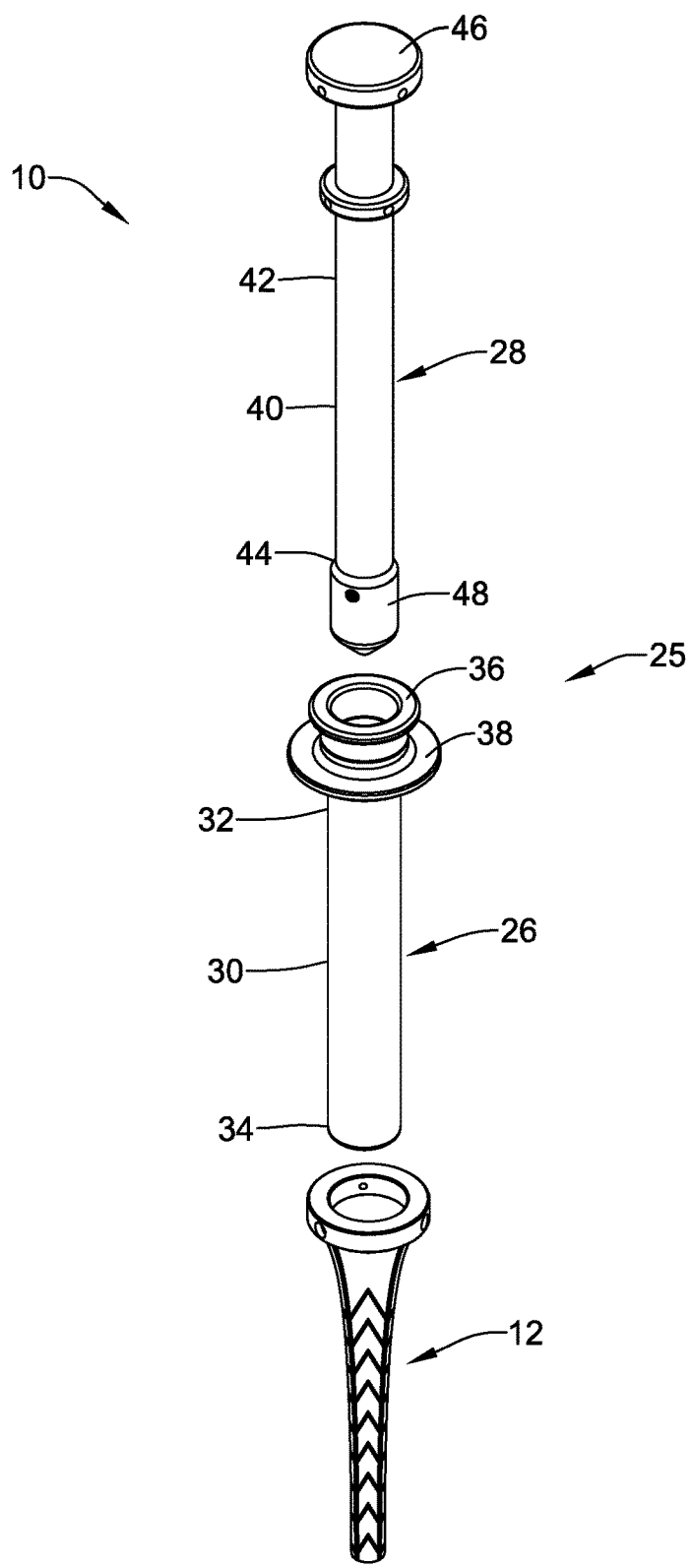
FIGS. 1C-1F illustrate an example medical device for accessing the central nervous system.

FIG. 1C illustrates the expandable access sheath 12 as well as some of the other components of the medical device 10. For example, the medical device may include an expansion member or assembly 25. In this example, the expansion member 25 may include a cannula 26 and/or a trocar 28. The cannula 26 may include a tubular body 30 having a proximal end region 32 and a distal end region 34. A hub 36 may be disposed at the proximal end region 32. The hub 36 may include a flanged region 38. The trocar 28 may include a body region 40 having a proximal end region 42 and a distal end region 44. A hub 46 may be disposed at the proximal end region 42. A tip 48 may be disposed at the distal end region 44. The tip 48 may have a tapered or atraumatic shape.

The expandable access sheath 12 may be designed to shift between a first configuration (e.g., as depicted in FIG. 1A and FIG. 1C; e.g., as depicted for the expandable access sheath 112 in FIG. 1B) and a second or expanded configuration. In some instances, the expandable access sheath 12 may be designed to be in the first configuration when in a natural state or when free of forces tending to expand the expandable access sheath 12. In other words, the expandable access sheath 12 may be understood to be biased to be in first configuration. In at least some instances, the expandable access sheath 12 may be described as being "collapsible" in that the expandable access sheath 12 may revert or shift back to the first configuration from an expanded configuration when expansion forces/mechanisms are removed from the expandable access sheath 12. In some embodiments, the material of the sleeve 21, may be elastic and/or resilient and/or possibly superelastic in nature, and may provide the biasing force towards the collapsed configuration of the sheath. For example, at rest, the sleeve 21 may be biased to the collapsed configuration, but expandable with some force to an expanded configuration. But when the expansion force is removed, the elastic and/or resilient nature of the sleeve 21 will allow it to revert back toward the collapsed configuration. The material of the sleeve 21 may allow for appropriate expansion and/or contraction as desired without significant plastic deformation. In some embodiments, the one or more axial support members 22 and/or struts 24 may also be made from and/or include a material that is elastic and/or resilient and/or possibly superelastic in nature, and may provide a requisite biasing force to the collapsed configuration—either in combination with and/or in lieu of the material of the sleeve 21.

Figure 1D:
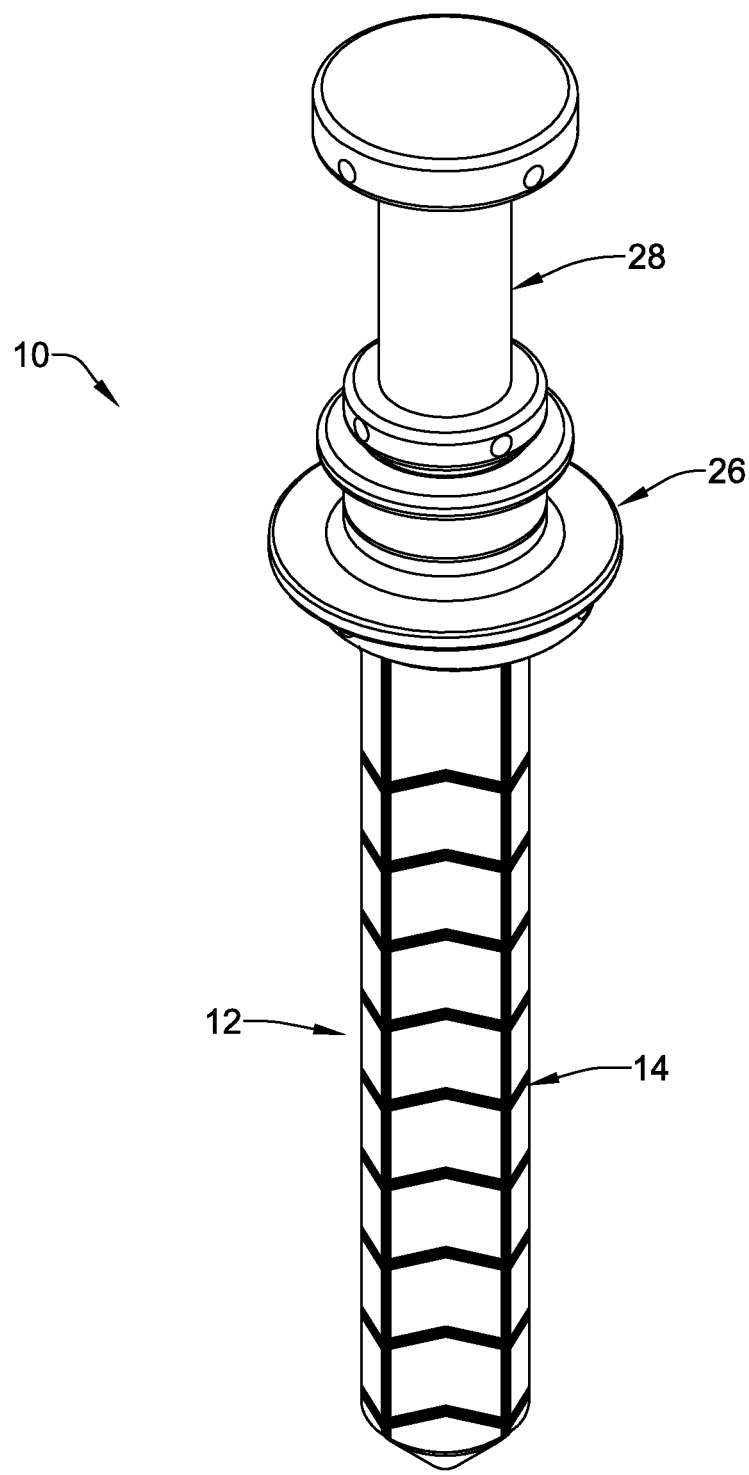
Figure 1E:
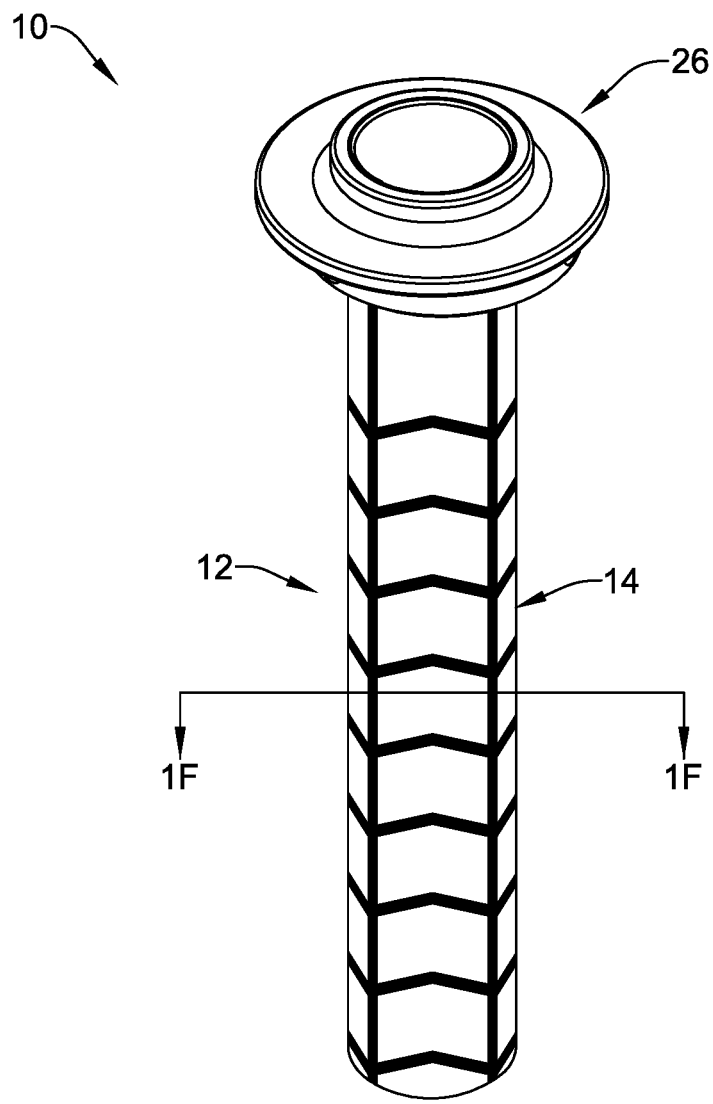

In at least some instances, the expandable access sheath 12 may be shifted to the expanded configuration by advancing or otherwise disposing the expansion member 25 within the expandable access sheath 12 as shown in FIG. 1D. For example, shifting the expandable access sheath to the expanded configuration may include disposing only the cannula 26 within the expandable access sheath 12, disposing only the trocar 28 within the expandable access sheath 12, extending both the cannula 26 and the trocar 28 within the expandable access sheath 12, and/or expanding the expandable access sheath 12 with another structural mechanism such as a balloon. In some instances, the trocar 28 may be removed from the expandable access sheath 12 as shown in FIG. 1E, leaving just the cannula 26 within the expandable access sheath 12. In at least some instances, the cannula 26 may be sufficient to hold the expandable access sheath 12 in the expanded configuration.

Figure 1F:
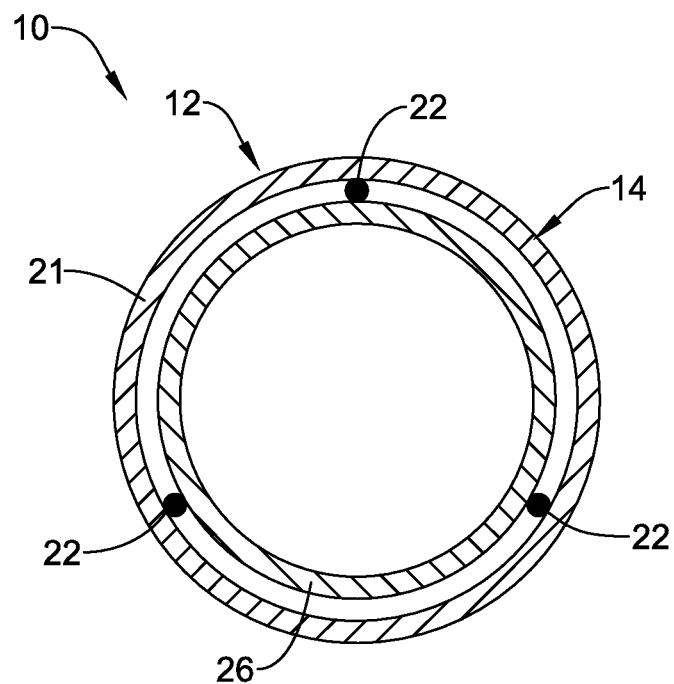

A cross-sectional view of the expandable access sheath 12 is shown in FIG. 1F. Here the sleeve 21, the axial support members 22, and the cannula 26 can be seen. In this example, the axial support members 22 are disposed along an inner surface of the sleeve 21. However, other configurations (e.g., embedded, outer surface, etc.) are contemplated. In at least some instances, the axial support members 22 may provide axial support to the sleeve 21 (and/or the expandable access sheath 12, in general) during navigation, expansion, and use. This may include the axial support members 22 helping to substantially reduce the likelihood that the sleeve 21 foreshortening during expansion. For example, the axial support members 22 may be understood to substantially fix the length of the sleeve 21 (and/or the expandable access sheath 12, in general). In some aspects, the axial supports 22 may function to maintain a generally fixed length of the sheath 12, even during radial expansion and/or contraction of the sheath 12.

FIGS. 2A-2D illustrate another example medical device 210 that may be similar in form and function to other medical devices disclosed herein. The medical device 210 may include an expandable access sheath 212. The expandable access sheath 212 may include a tubular body 214 having a proximal end region 216 and a distal end region 218. The tubular body 214 of the expandable access sheath 212 may include a sheath or sleeve 221. One or more axial support member 222 may be disposed along, coupled to, or embedded in the sleeve 221.

Figure 2A:
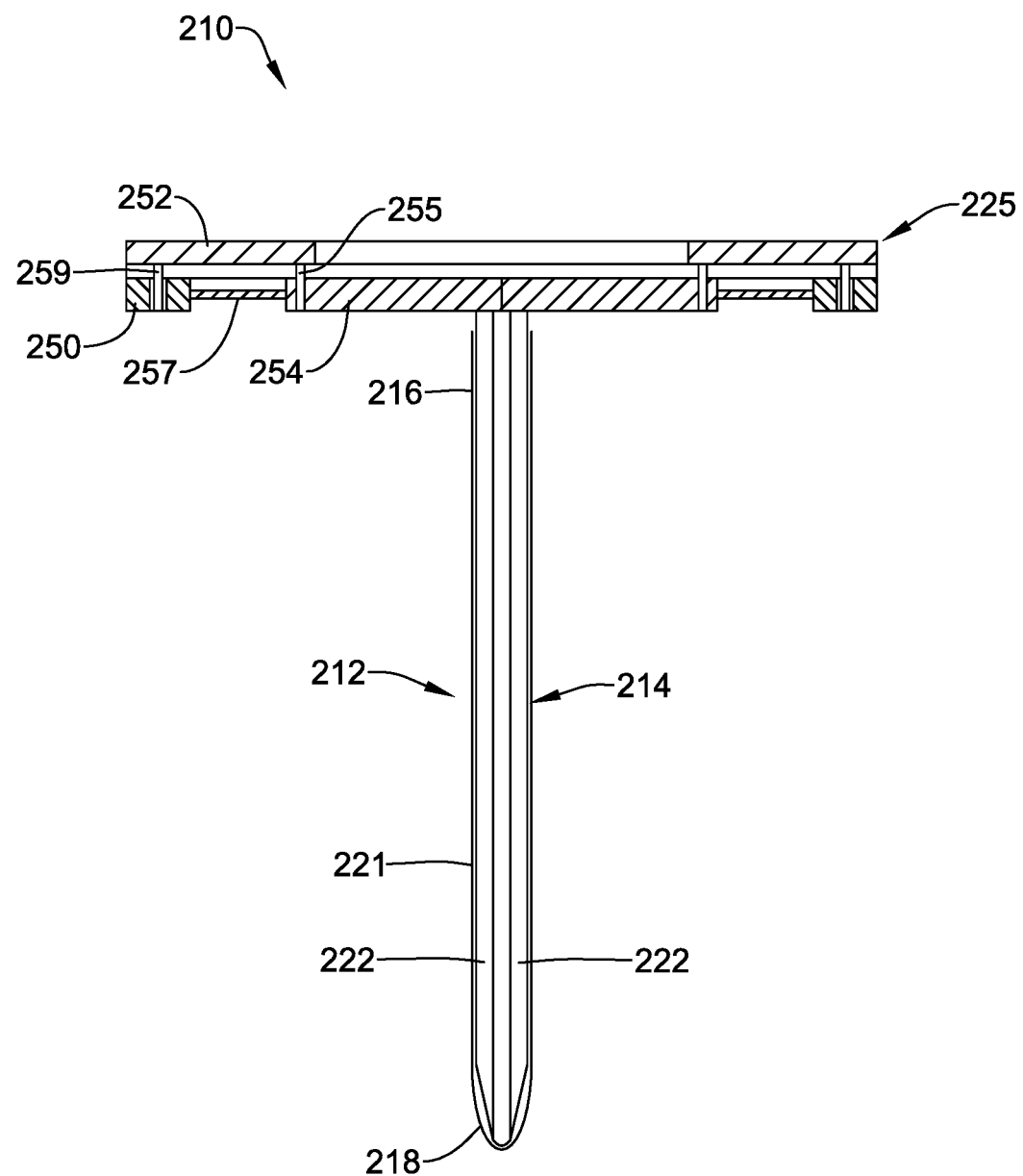
FIGS. 2A-2D illustrate an example medical device for accessing the central nervous system.
Figure 2B:
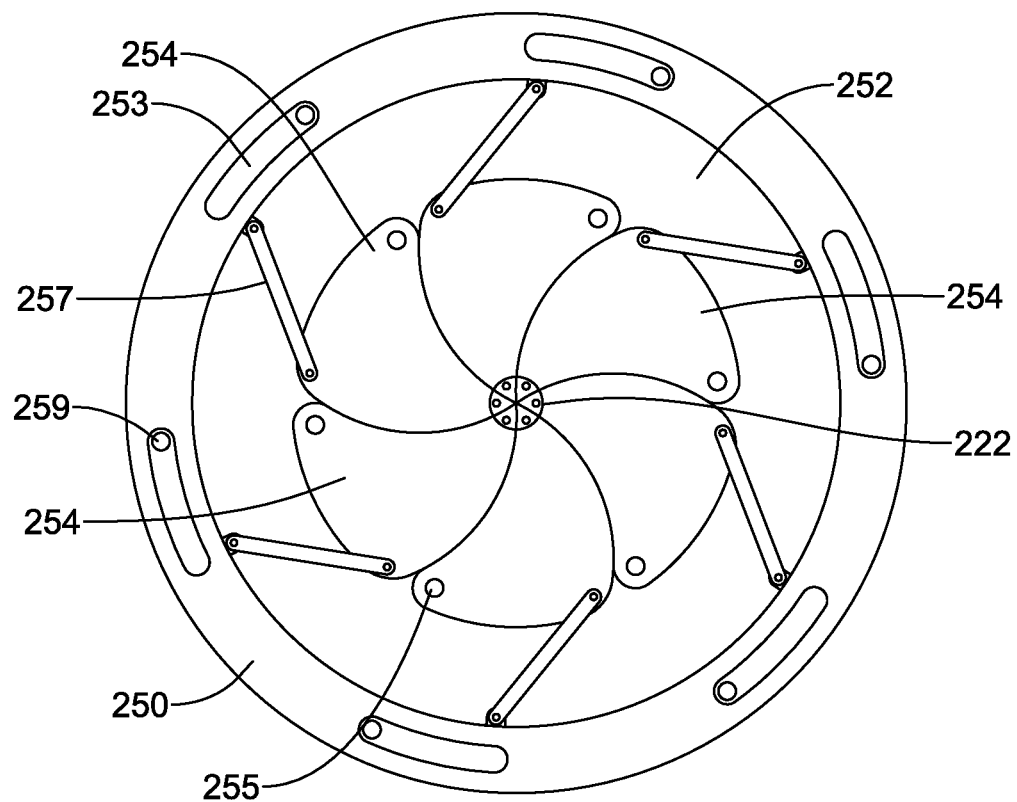
Figure 2C:
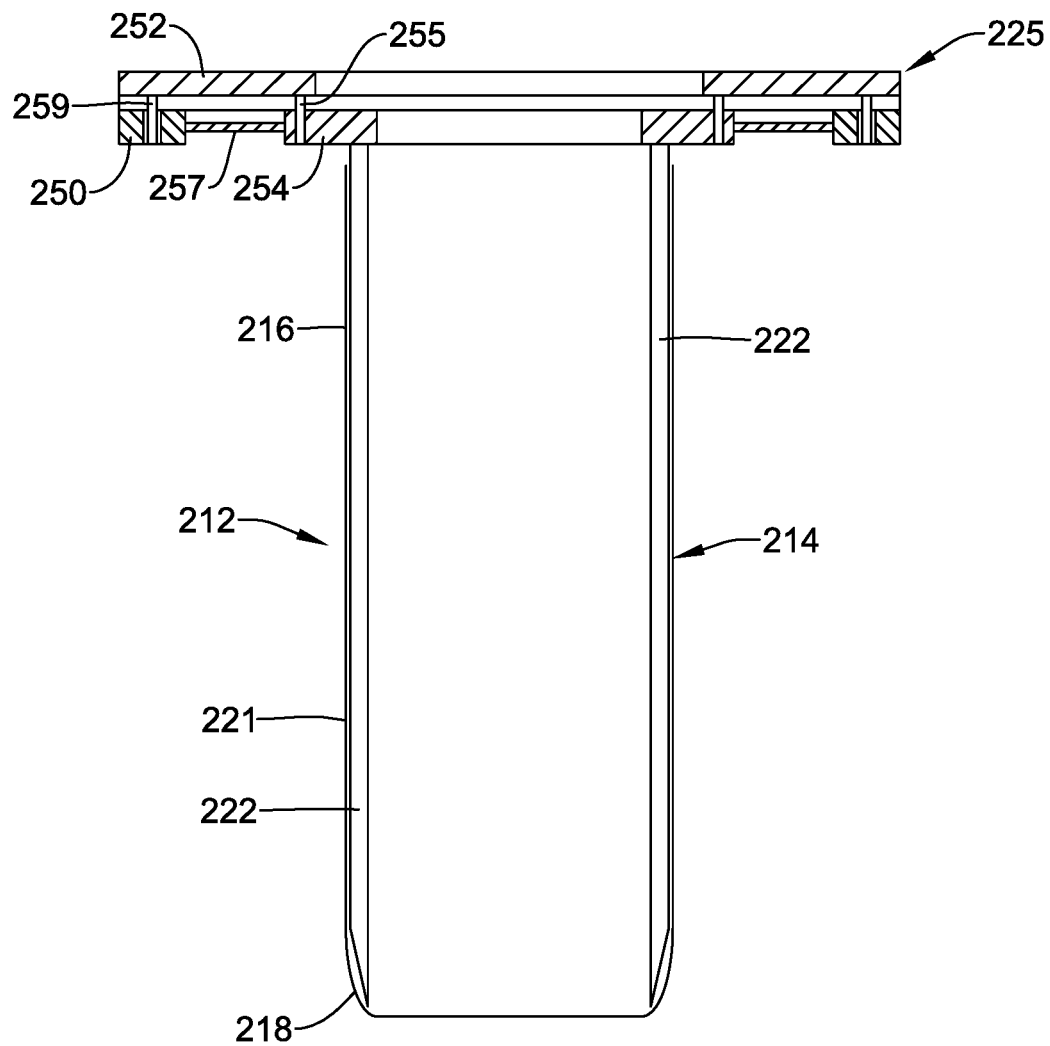
Figure 2D:
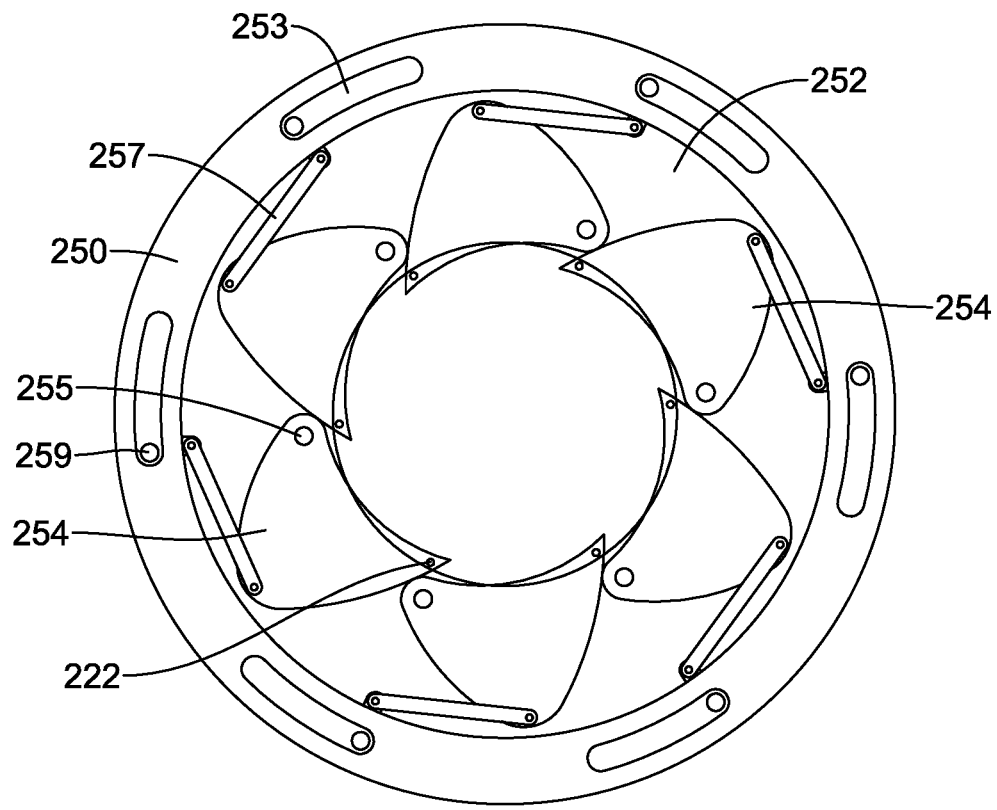
Figure 3A:
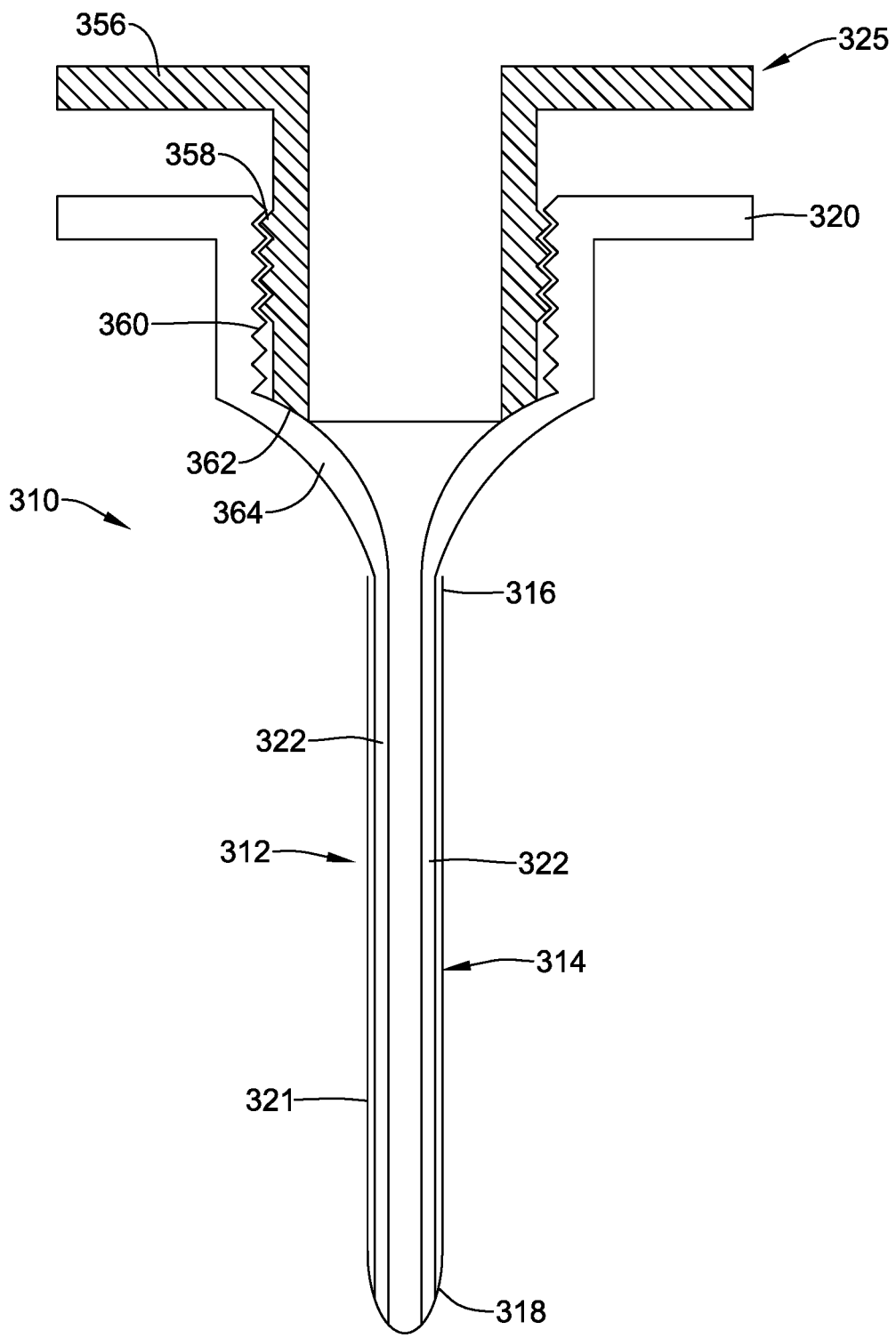
FIGS. 3A-3D illustrate an example medical device for accessing the central nervous system.
Figure 3B:
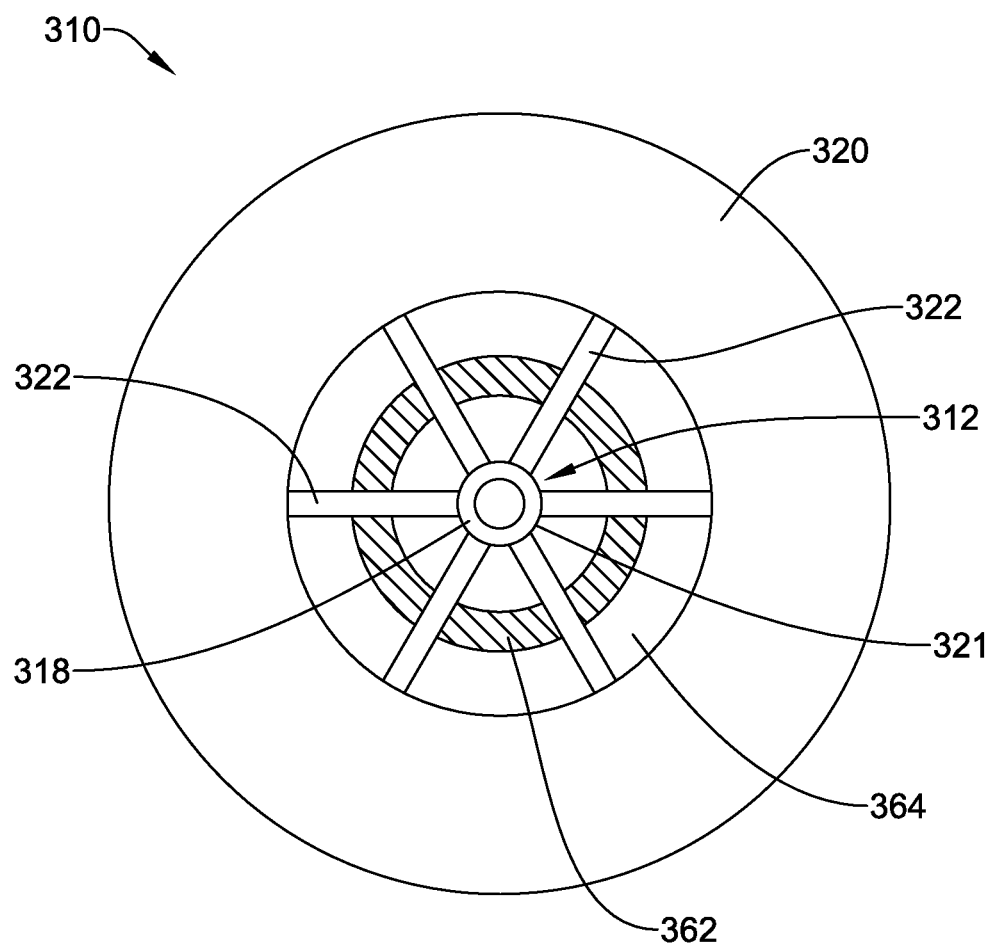
Figure 3C:
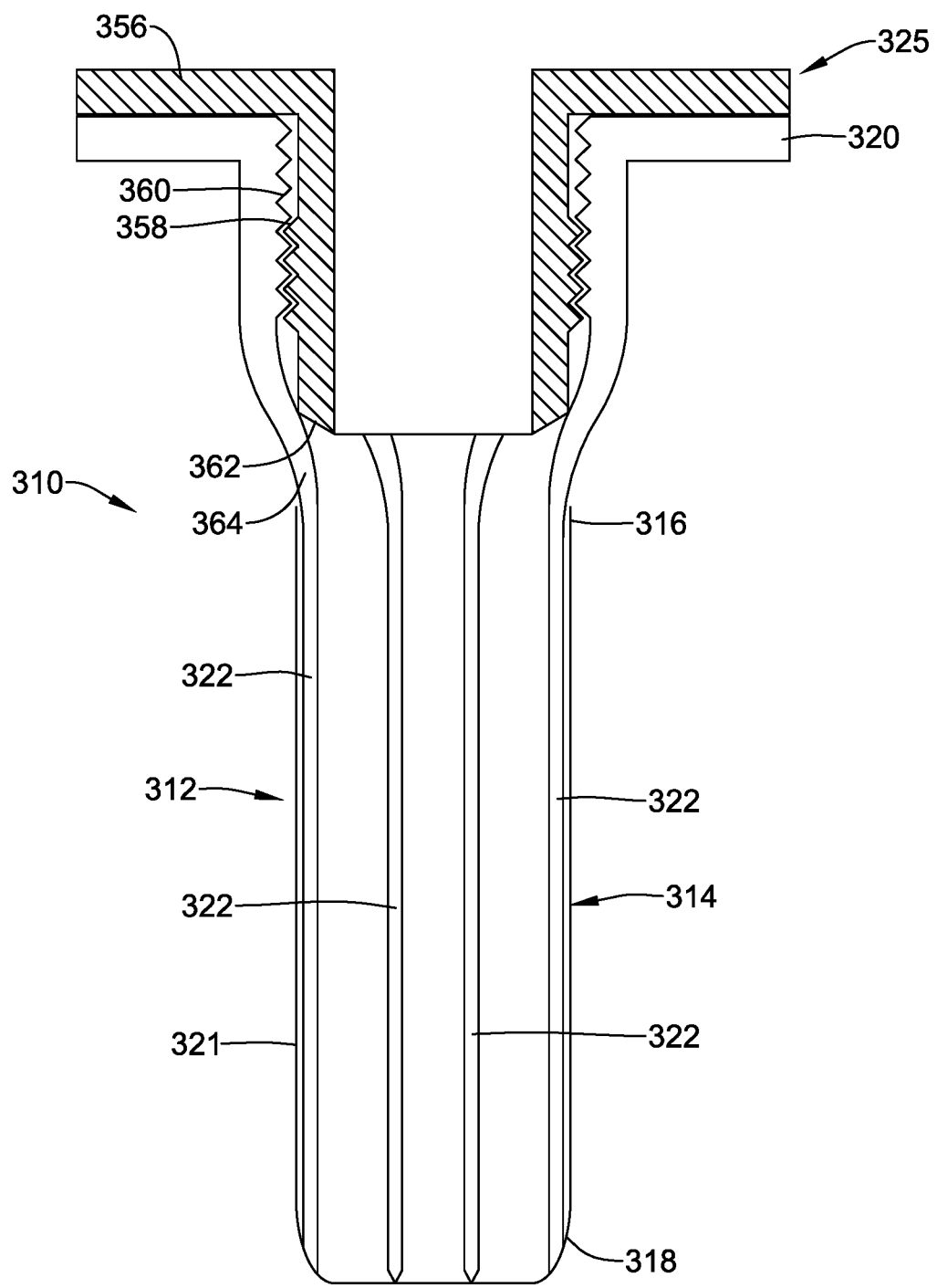
Figure 3D:
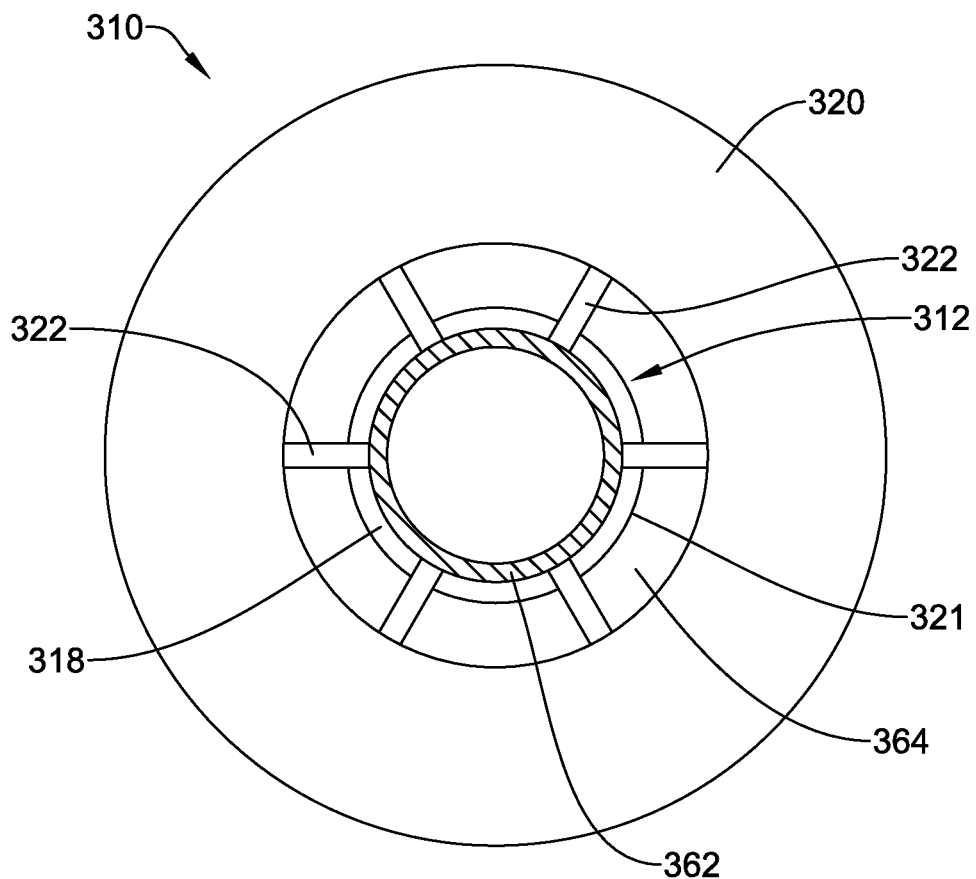

An expansion mechanism and/or member 225 may be disposed at or otherwise coupled to the proximal end region 216. The expansion member 225 may resemble or otherwise take the form of an iris mechanism and/or expansion device and/or valve. Iris mechanisms are generally know, and may be generally described as an adjustable mechanism of a plurality of blades that can be moved by rotational movement of a support so as to change the diameter of a central opening formed by the blades. For example, the example iris expansion member 225 may include a ring member 250 and a top base 252. A groove or slot 253 may be formed in the ring member 250 (e.g., as shown in FIGS. 2B and 2D). The expansion member 225 may also include a plurality of blade members 254. In this example, the blade members 254 are coupled to the top base 252 by a pin 255. A linkage 257 may extend between the ring member 250 and the blade members 254. Another pin 259 may extend between the ring member 250 and the top base 252. This is just one example of a possible configuration for the expansion member 225. A number of different iris mechanism types of expansion members 225 are contemplated. Some examples of these iris expansion structures that may be suitable for use as part of the expansion member 225 are disclosed in U.S. Pat. Nos. 4,130,113, 5,779,681, U.S. Patent Application Pub. No. US 2011/0054405, and U.S. Patent Application Pub. No. US 2014/0114138, the entire disclosures of which are herein incorporated by reference.

FIGS. 2B and 2D are end views from the distal end region 218 of the expandable access sheath 212. From these figures it can be seen that rotation of the top base 252 relative to the ring member 250 may rotate or otherwise "open" the blade members 254, which may move the axial support members 222 radially outward and shift the expandable access sheath 212 from a first configuration (e.g., as depicted in FIG. 2A) to an expanded configuration as shown in FIGS. 2C-2D. For example, rotation of the top base 252 relative to the ring member 250 exerts a force on the linkage 257 and causes the blade members 254 to rotate about the pin 255. When the blade members 254 rotate radially outward, the axial support members 222 also shift radially outward, shifting the expandable access sheath 212 from a first configuration to an expanded configuration. It should be noted that an iris expansion device (e.g., the expansion member 225) may allow for incremental changes in the level of expansion of the expandable access sheath 12. Thus, the expansion member 225 may allow for the expandable access sheath 212 to shift between the first configuration and the expanded configuration as well as a plurality of positions (e.g., essentially an infinite of positions) therebetween. The expansion mechanism may include a lock or other mechanism to maintain the sheath 212 in the desired position. Additionally, as discussed above relative to the sheath 12, the sleeve 221 and/or one or more axial support members 222 may be made of and/or include an elastic and/or resilient and/or superelastic material that may provide a biasing force into a closed configuration.

FIGS. 3A-3D illustrate another example medical device 310 that may be similar in form and function to other medical devices disclosed herein. The medical device 310 may include an expandable access sheath 312. The expandable access sheath 312 may include a tubular body 314 having a proximal end region 316 and a distal end region 318. A hub or flange 320 may be disposed at the proximal end region 316. The tubular body 314 of the expandable access sheath 312 may include a sheath or sleeve 321. The sheath or sleeve 321 may be made of and/or include materials and/or may function similarly to the sheath or sleeve 21, 121, 221 as discussed above. One or more axial support member 322 may be disposed along, coupled to, or embedded in the sleeve 321. The one or more axial support member 322 may be made of and/or include materials and/or may function similarly to the support member 22, 122, 222 as discussed above. In at least some instances, the hub 320 may be defined by and/or attached to the proximal ends of the axial support members 322. In this embodiment, support members 322 include inwardly curved and/or bowed regions near the proximal ends thereof.

An expansion mechanism and/or member 325 may be disposed at or otherwise coupled to the proximal end region 316. In this example, the expansion member 325 may include a threaded actuation mechanism and/or bolt 356 having a threaded region 358. The threaded region 358 may be designed to engage threads along the hub 320 and/or proximal regions of the axial support members 322 (e.g., at or near the hub 320). Actuation/rotation of the actuation mechanism and/or bolt 356 may cause a distal end region 362 of the mechanism and/or bolt 356 to engage the inwardly bowed and/or curved region 364 of the axial support members 322. Because the axial support members 322 may be substantially rigid, the engagement of the distal end region 362 of the actuation mechanism 356 and the curved regions 364 may urge or deflect the axial support members 322 radially outward (e.g., and shift the expandable access sheath 312 toward the expanded configuration).

Just like the expansion member 225, the expansion member 325 may allow for the expandable access sheath 312 to shift between the first configuration and the expanded configuration as well as a plurality of positions (e.g., essentially an infinite of positions) there between. The expandable access sheath 312 may be biased toward the first and/or collapsed configuration. For example, the axial support members 322 may be made of a resilient and/or elastic and/or superelastic material, and may include a shape, such as the inwardly bowed and/or curved region, that will bias the sheath 312 into the first and/or collapsed configuration. The actuation mechanism may provide a force to overcome this bias, and force the sheath into an expanded configuration. When the actuation mechanism and/or bolt 356 is backed out and/or moved proximally, such that the distal end region 362 moves proximally, and disengages from the inwardly bowed and/or curved region 364, the access sheath 312 may revert back toward the first and/or collapsed configuration. In some embodiments, the sleeve 121 may be made of and/or include an elastic and/or resilient and/or superelastic material that may provide a biasing force into a closed configuration—either in lieu of and/or in addition to the bias of the axial support members 322.

FIGS. 4A-4E illustrate a medical device system 400 and some examples of the methods for using the system 400 and/or the medical device 10 and/or the expandable access sheath 12. The system 400 may include the expandable access sheath 12 (and/or other expandable access sheaths disclosed herein). The system 400 may also include the expansion member 25 (e.g., which may include the cannula 26 and/or the trocar 28).

The system 400 may also include a stylet 466. The stylet 466 may be an elongated tool used to help navigate to a target within the anatomy, and may aid in the placement and/or orientation of other devices, such as the access sheath 12. The stylet 466 includes a distal shaft 468, a tip member 470, and a proximal shaft 472. In some instances, the tip member 470 may include a camera or other type of imaging member. The stylet 466 may include and/or be used with a surgical navigation and/or tracking system to aid the user in navigating and/or tracking the stylet 466 to a desired location and/or orientation within the anatomy. For example, the stylet may include and/or be usable with an optical and/or electromagnetic tracking system. In such systems, the stylet may include a series or markers and/or sensors 476 disposed on the proximal shaft 472. These markers and/or sensors 476 are registered relative to the location and/or orientation of the tip member 470. In the case of an example optical navigation system, markers 476 would be passive/reflective optical markers, and the operating suite would include a series of cameras that detect the position and orientation of the markers 476, which is then used to determine the position of the tip 470. In the case of an example electromagnetic navigation system, sensors 476 would be electromagnetic field sensors, and the operating suite would include one or more electromagnetic field generators. The position of the sensors would be determined relative to the electromagnetic field, and thus provide the position of the tip 470.

In some embodiments, the stylet may also include other markers and/or reference points, such as visual markers, markers detectable by magnetic resonance imaging, markers detectable by optical coherence tomography, markers detectable by fluoroscopy, or markers detectable by another mechanism. In at least some instances, the markers 476 may be used to trace, detect, and/or otherwise track the position of the stylet 466 (e.g., relative to the patient).

The system 400 may also include a device orienting assembly 478. The device orienting assembly 478 may include a base 480 and one or more adjustable legs 482 coupled thereto. The adjustable legs 482 may be used to adjust the position, height, tilt or angle, and/or otherwise the orientation of the base 480. A locking arm 484 may also be coupled to the base 480. The base 480 may also include an opening or passageway 486 for accommodating the expandable access sheath 12. A locking member (not shown) may be positioned at or near the opening 486. The locking member may be used to secure the expandable access sheath 12 to the device orienting assembly 478.

Figure 4A:
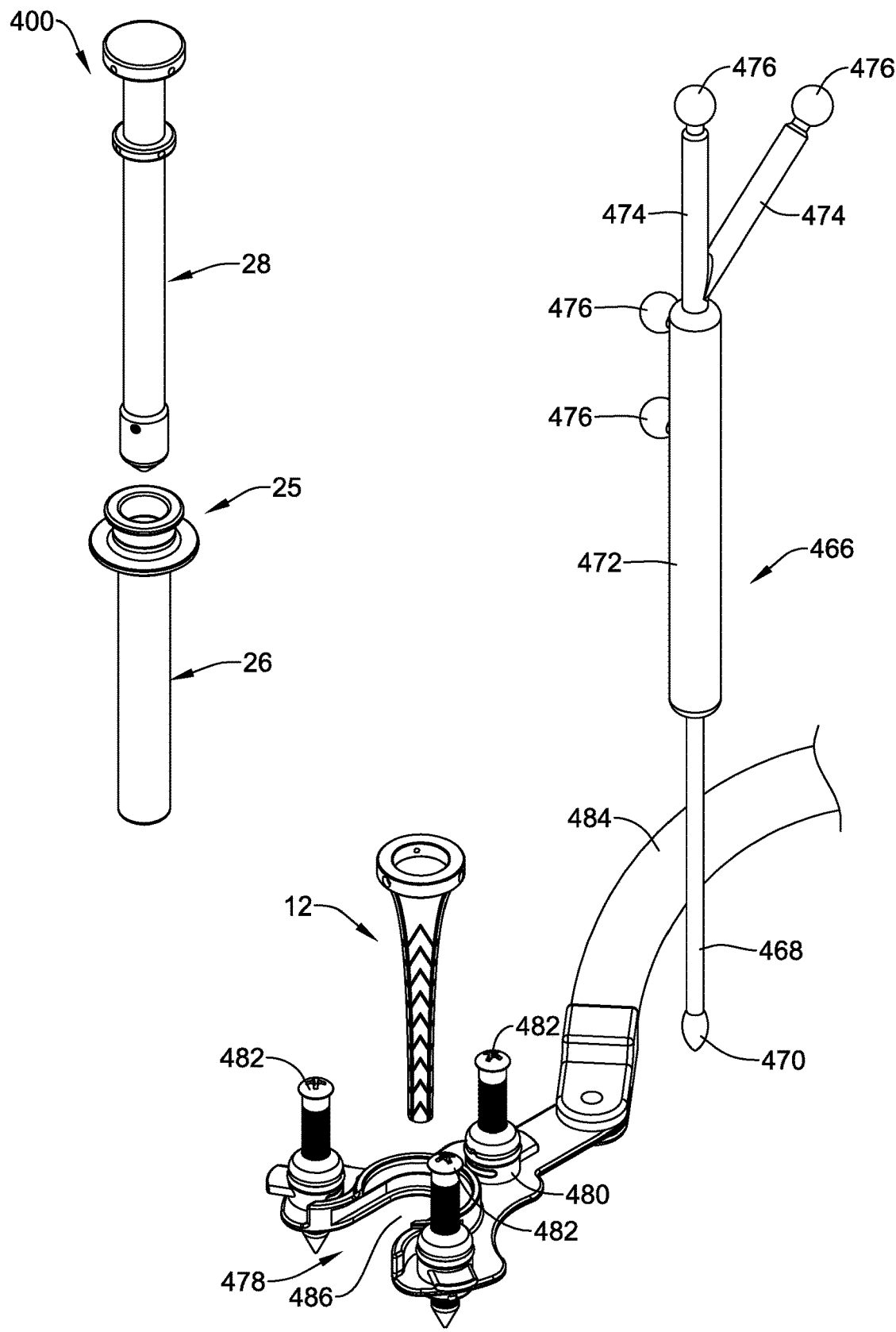
FIGS. 4A-4E illustrate an example medical device system and the use of the example medical device system.
Figure 4B:
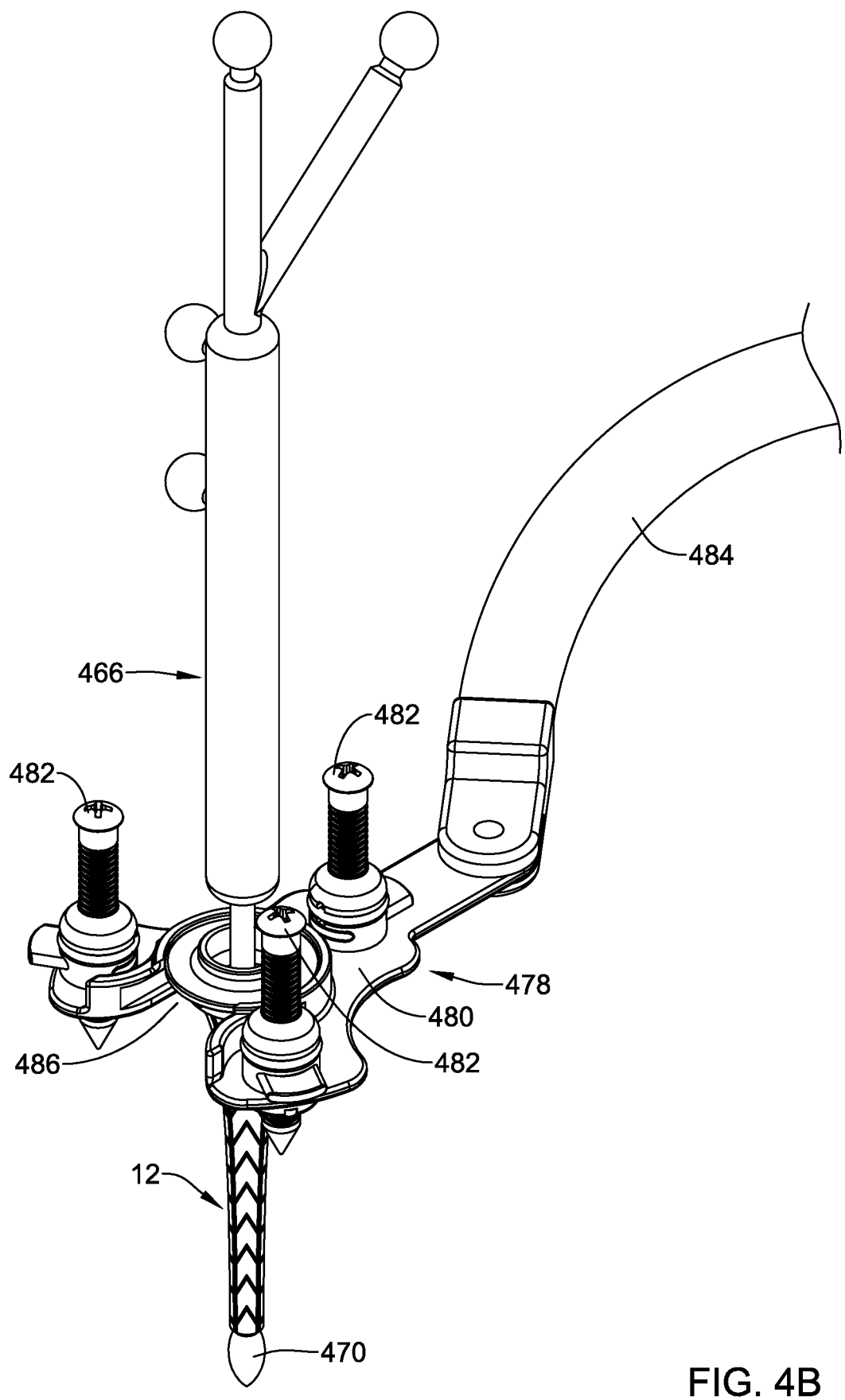

In use, the base 480 may be placed onto an appropriately prepared surface of a patient such as along the head. The adjustable legs 482 and the locking arm 484 may be used to orient the base 480 in a desired manner so as to guide the expandable access sheath 12 toward the target region (e.g., including the desired angle, height, etc.). The expandable access sheath 12 having the stylet 466 extending therethrough may extend through the opening 486 as shown in FIG. 4B and into the patient. When doing so, the stylet 466 may be used to help locate the target. In some interventions, the distance from the device orienting assembly 478 may differ from the length of the expandable access sheath 12. In such instances, the axial position of the expandable access sheath 12 can be adjusted by shifting the position of the adjustable legs relative to the base 480. This may raise or lower the expandable access sheath 12 within the anatomy, and may help to guide the expandable access sheath 12 to the desired depth within the brain.

Figure 4C:
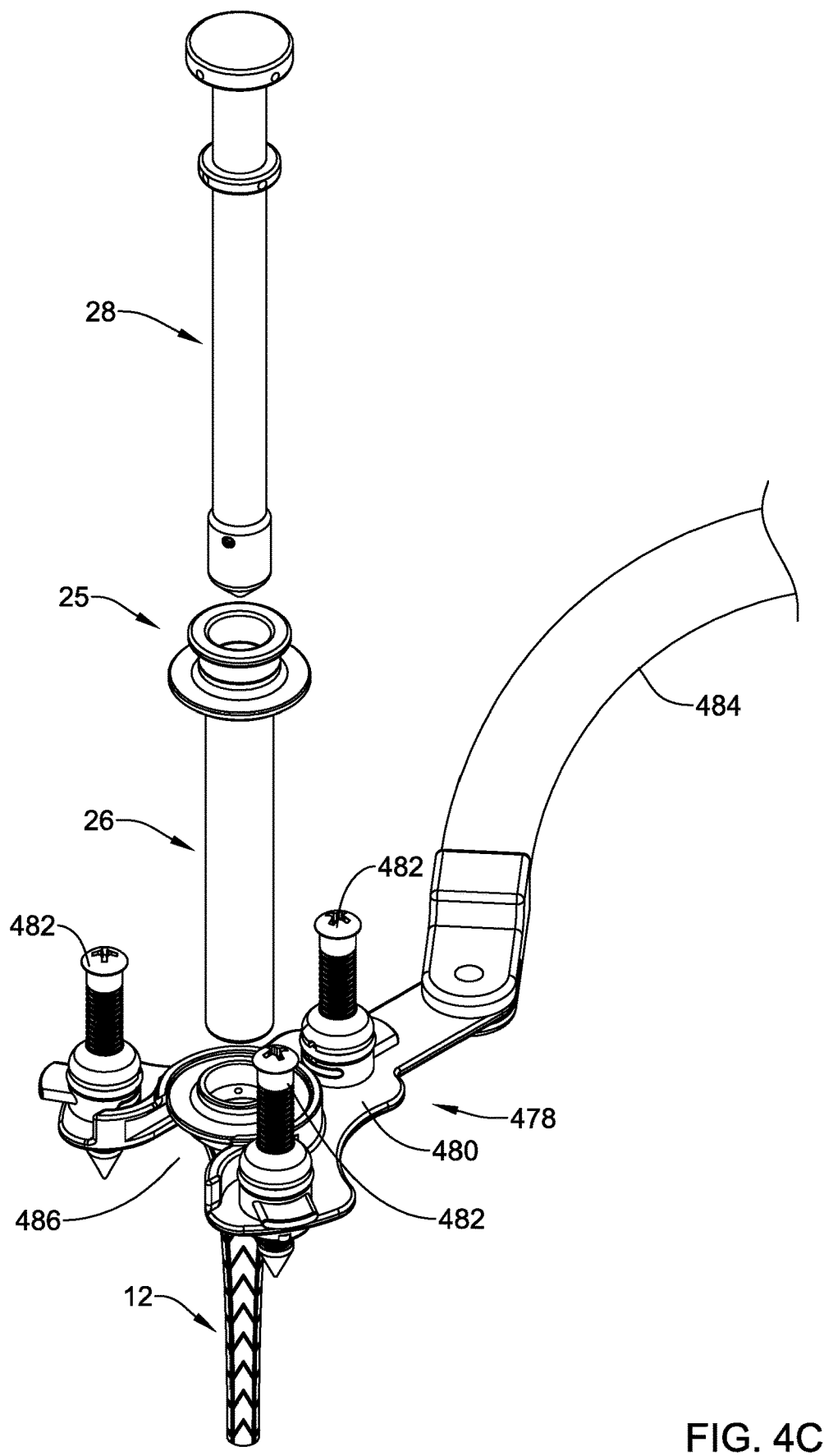
Figure 4D:
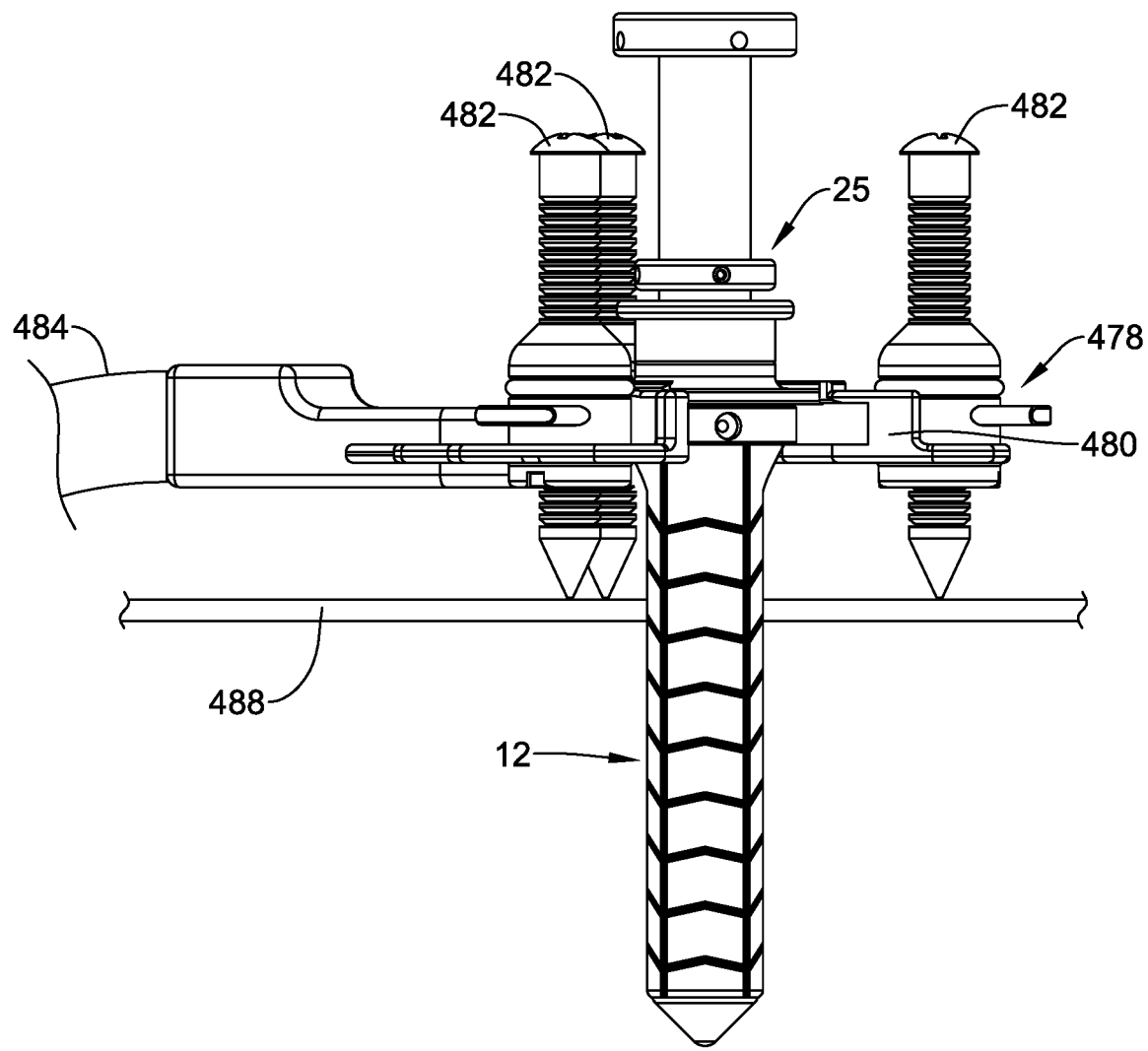
Figure 4E:
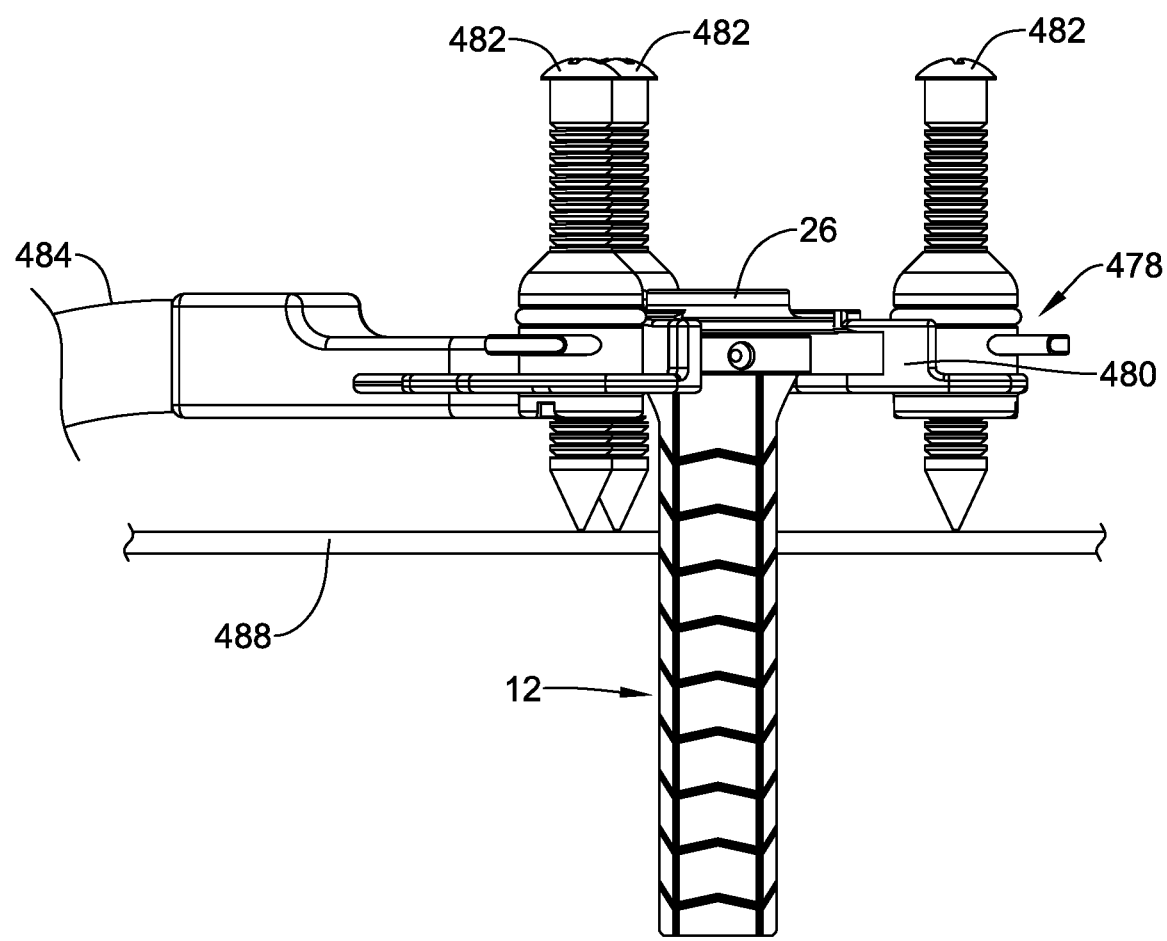

Upon reaching the target, the stylet 466 can be removed. The expansion member 25 can be disposed within the expandable access sheath 12 as depicted in FIGS. 4C-4D. When doing so, the expandable access sheath 12 may shift to the expanded configuration. If desired, the trocar 28 can be removed as shown in FIG. 4E. A suitable treatment device can be passed through the expandable access sheath 12 to treat the target region.

FIGS. 5A-5D illustrate a medical device system 500 and some examples of the methods for using the system 500 and/or the medical device 10 and/or the expandable access sheath 12. The system 500 may include the expandable access sheath 12 (and/or other expandable access sheaths disclosed herein). The system 500 may also include the expansion member 25 (e.g., which may include the cannula 26 and/or the trocar 28). The system 500 may also include the stylet 466.

The system 500 may also include a device orienting assembly 578. The device orienting assembly 578 may include a base 580. A locking arm 584 may be coupled to the base 580. An adjustable member 590 may be coupled to the base 580. The adjustable member 590 may include an adjustment mechanism 592 designed to engage a corresponding adjustment mechanism 594 disposed along the base 580. The adjustment mechanism 592 on the adjustable member 590 as well as the adjustment mechanism 594 on the base 580 may include a plurality of corresponding teeth that may be interlocking and/or resemble a ratcheting system. The base 580 may also include an actuator 596. The actuator 596 may take the form of pinchable arms or a spring clip that allows the adjustment mechanism 594 on the base 580 to open, widen, and/or otherwise unlock. When doing so, the axial position of the adjustable member 590 can be shifted relative to the base 580. When the actuator 596 is release, the adjustment mechanism 594 on the base 580 may close, shorten, or otherwise lock such that the axial position of the adjustable member 590 may be fixed relative to the base 580. When the expandable access sheath 12 is coupled to the adjustable member, the axial position of the expandable access sheath 12 can be adjusted relative to the base 580. In some instances, the device orienting assembly 578 may also allow the expandable access sheath 12 to pivot (e.g., change the angle of the expandable access sheath 12 relative to the patient).

Figure 5A:
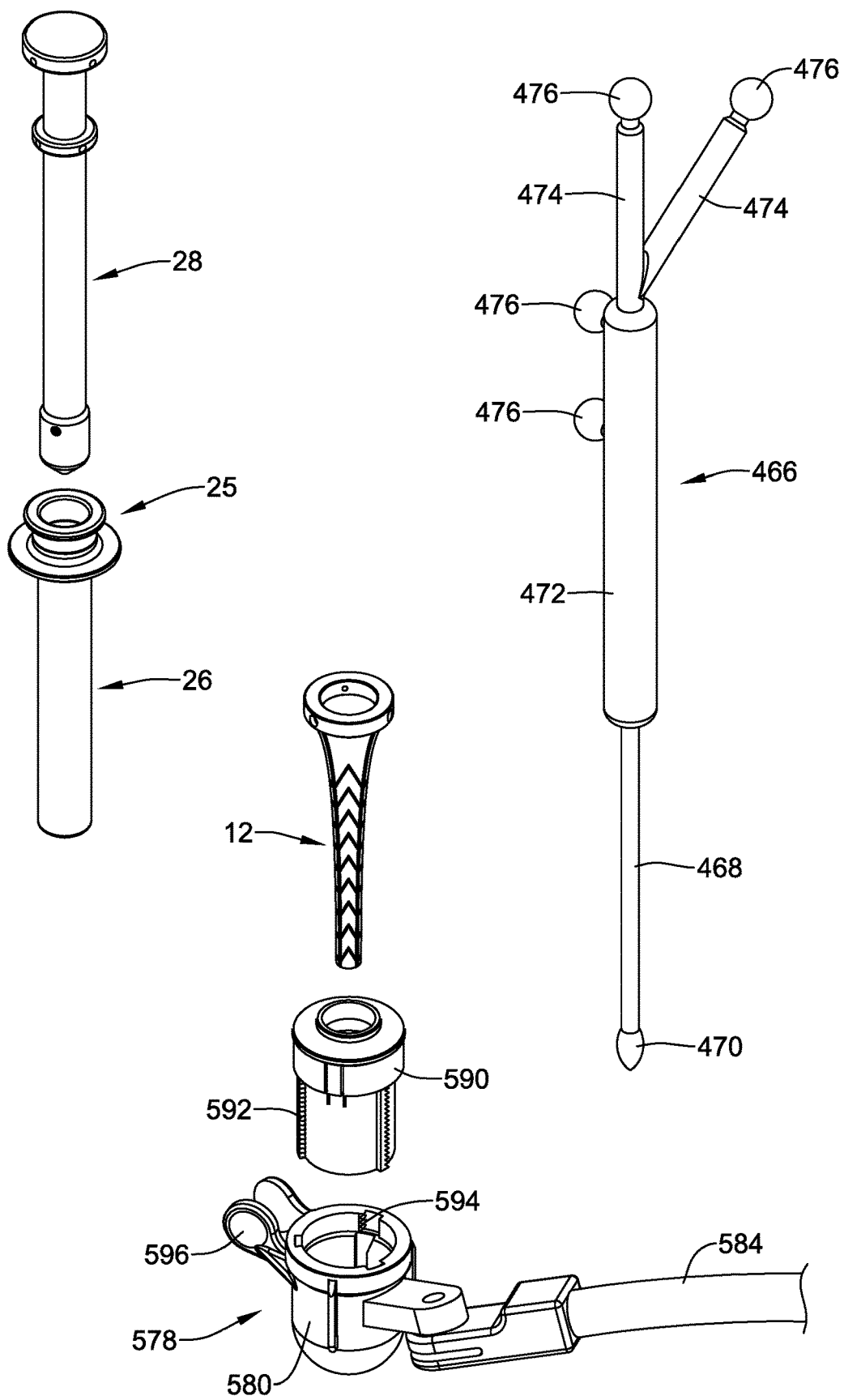
FIGS. 5A-5D illustrate an example medical device system and the use of the example medical device system.
Figure 5B:
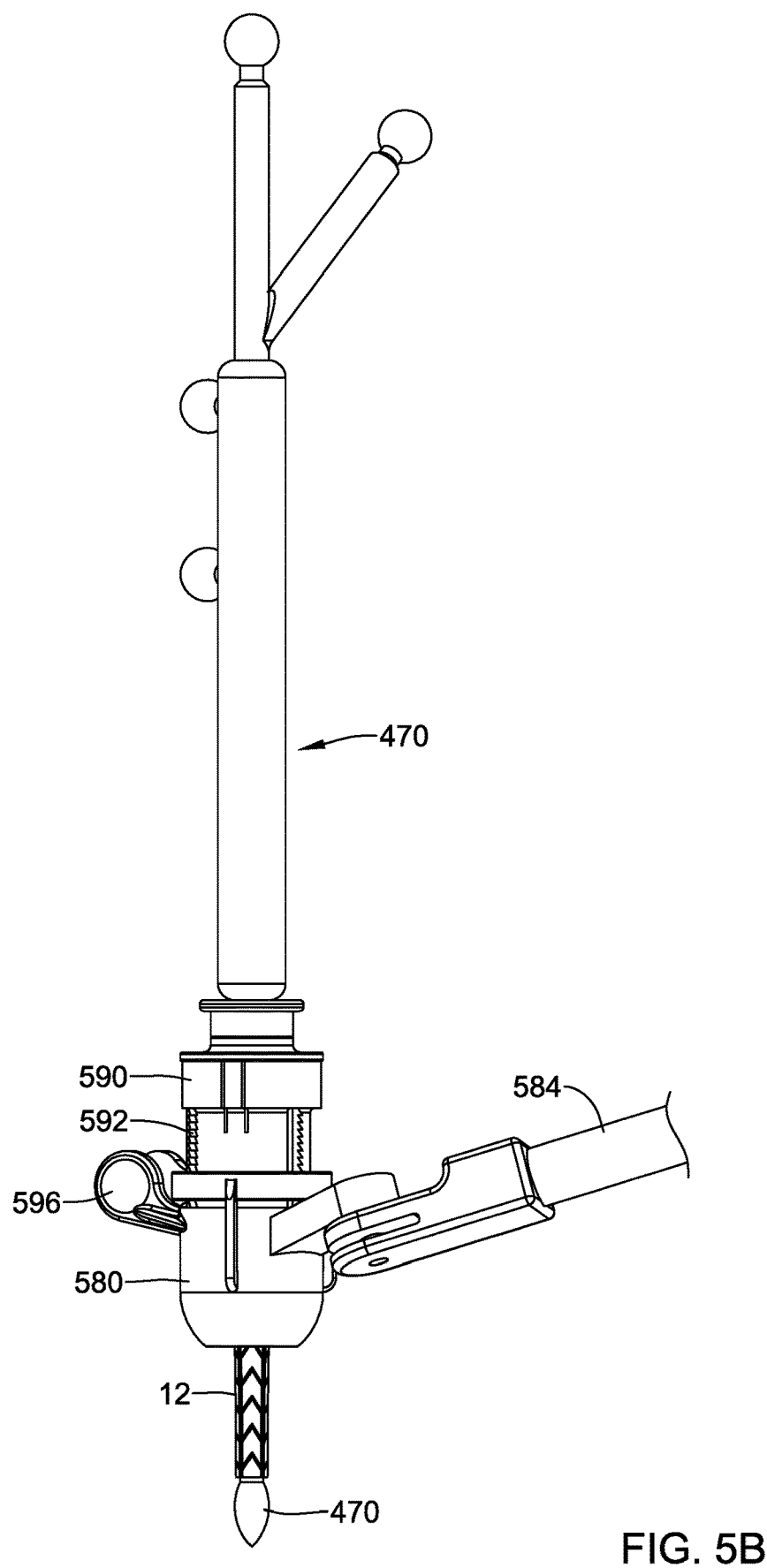

In use, the base 580 may be placed onto an appropriately prepared surface of a patient such as along the head. The expandable access sheath 12 having the stylet 466 extending therethrough may extend through the device orienting assembly 578 as shown in FIG. 5B and into the patient. When doing so, the stylet 466 may be used to help view and/or locate the target. In some interventions, the distance from the device orienting assembly 578 may differ from the length of the expandable access sheath 12. In such instances, the axial position of the expandable access sheath 12 can be adjusted by shifting the position of the adjustable member 590 relative to the base 580. This may help to guide the expandable access sheath 12 to the desired depth within the brain.

Figure 5C:
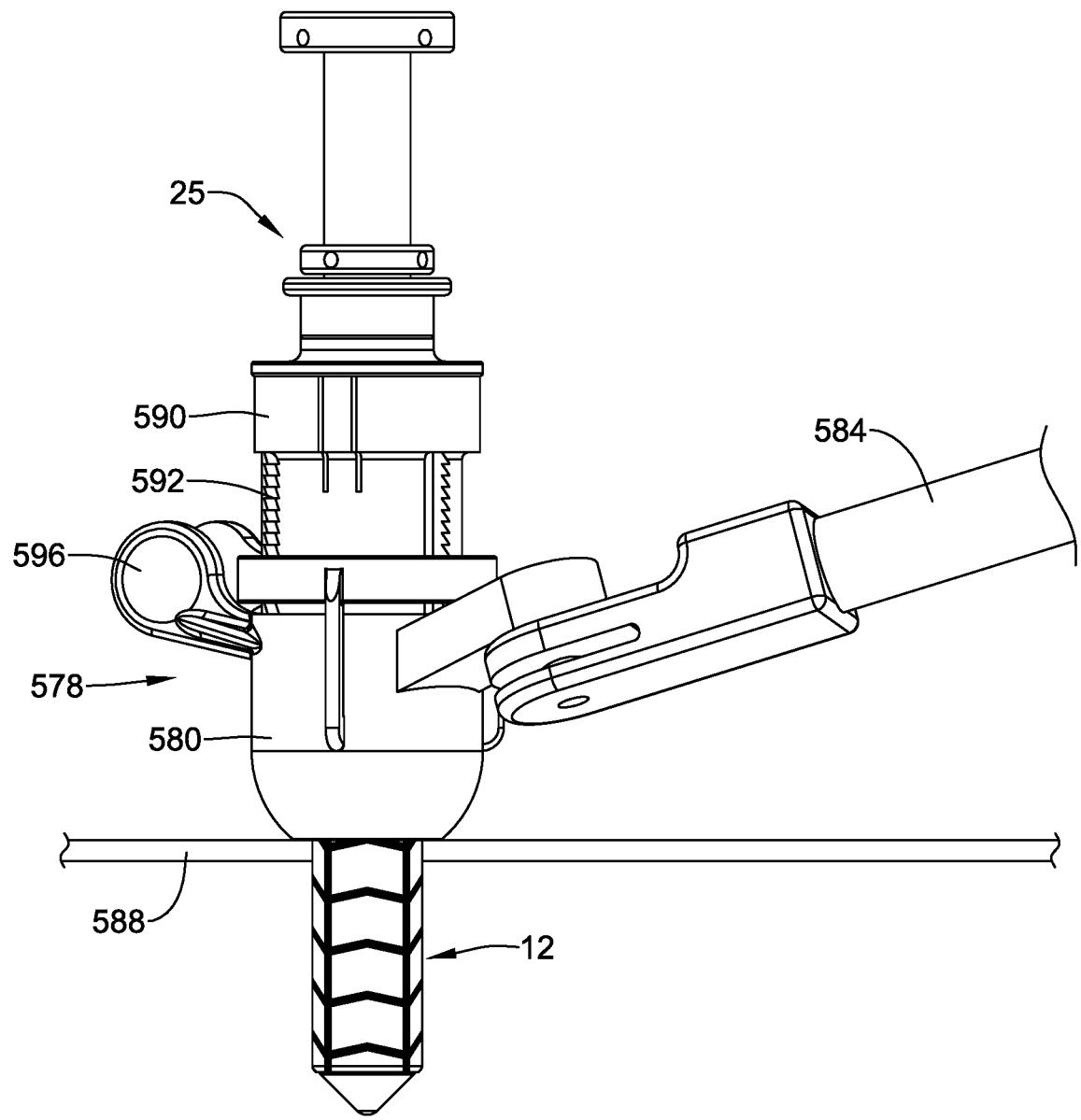
Figure 5D:
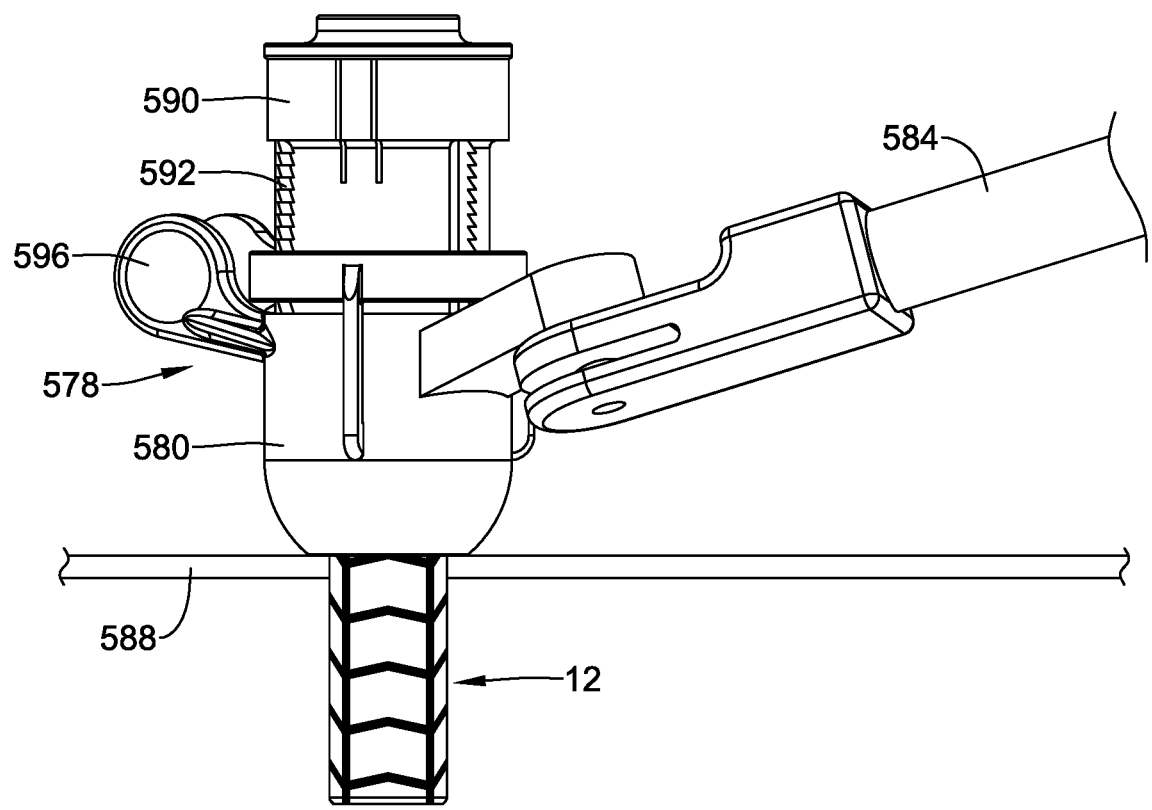

The device orienting assembly 578 may be oriented relative to a surface 588 of a patient. Upon reaching the target, the stylet 466 can be removed. The expansion member 25 can be disposed within the expandable access sheath 12 as depicted in FIG. 5C. When doing so, the expandable access sheath 12 may shift to the expanded configuration. If desired, the trocar 28 can be removed as shown in FIG. 5D. A suitable treatment device can be passed through the expandable access sheath 12 to treat the target region.

Figure 6A:
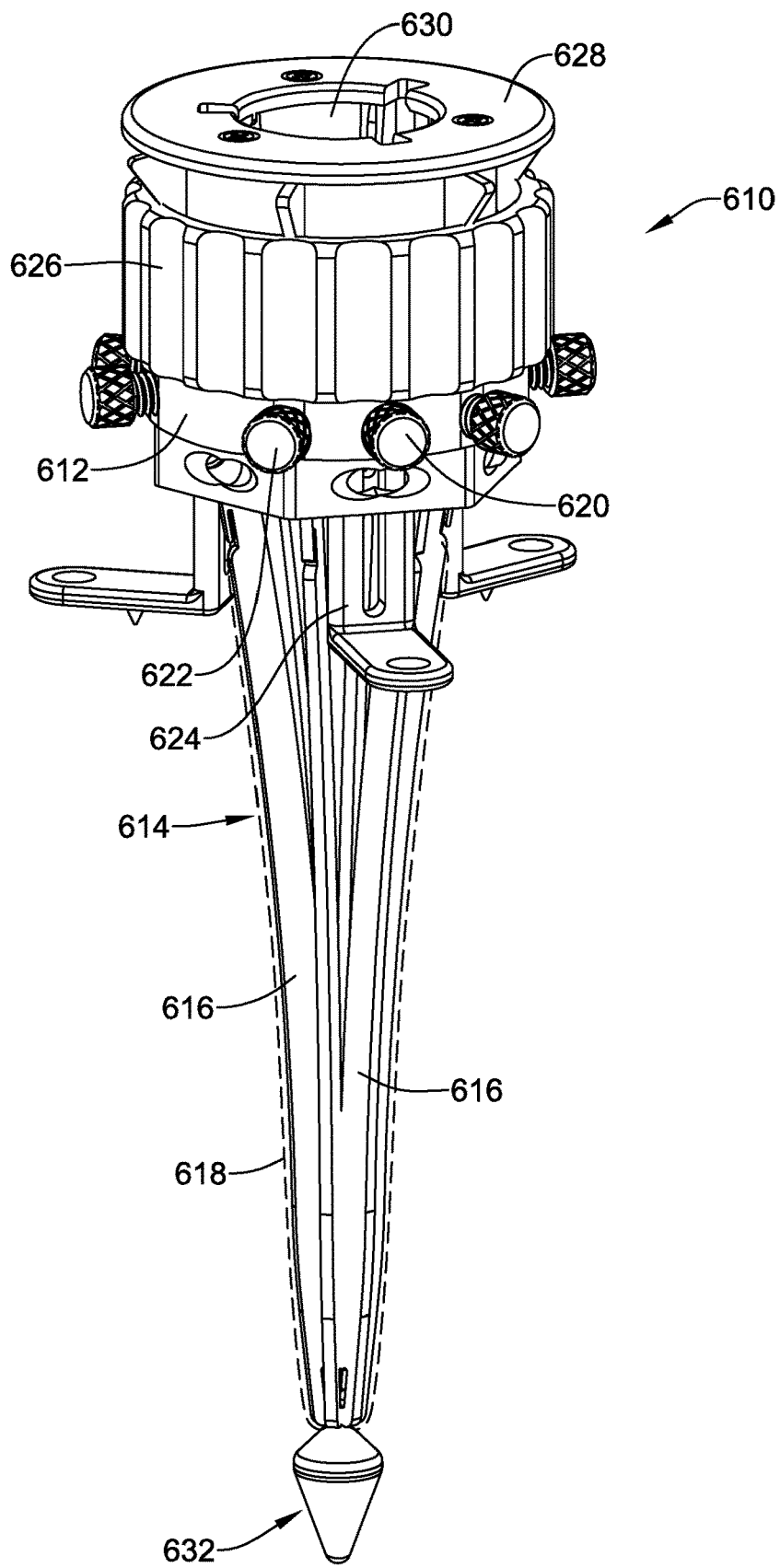
FIG. 6A is a perspective view of an example expandable access port.

FIG. 6A is a perspective view of an example expandable access port 610. The expandable access port 610 may be similar in form and function other medical devices, expandable access sheaths, expandable access ports, and/or the like as disclosed herein. In general, the expandable access port 610 may be used to access a target region along the central nervous system. The term "port" may be understood to indicate that the expandable access port 610 may take the form of an access point or hub that allows a clinician to access regions of the brain. It may be appropriate to describe the expandable access port 610 as an access sheath or other similar device. In some instances, the expandable access port 610 may include a base or housing 612. An expandable conduit 614 may be coupled to the housing 612. In general, the expandable conduit 614 may be designed to shift between a first configuration and an expanded configuration. The first configuration may be suitable for navigating the expandable access port 610 toward a target region such as a region along the central nervous system. In some instances, the first configuration may be understood to be a collapsed configuration, a partially collapsed configuration, or an unexpanded configuration. The expanded configuration is typically larger than the first configuration (e.g., the expandable conduit 614 has a greater diameter when in the expanded configuration than when in the first configuration). The expanded configuration may help to open up space around the expandable access port 610 in order to aid visualization, diagnosis, provide access for another device, aid in the delivery of a drug or other active agent, or the like.

The expandable conduit 614 may include a plurality of arms or tines 616. The tines 616 may be disposed circumferentially about the housing 612 in order to form or define the expandable conduit 614. The tines 616 may take the form of wires, ribbons, rods, or the like. The expandable access port 610 may include a suitable number of tines 616. For example, the expandable access port 610 may include two, three, four, five, six, seven, eight, nine, ten, or more tines 616. In some instances, all of the tines 616 have the same shape, size, and/or configuration. In other words, in some instances, all of the tines 616 are the same. In other instances, one or more of the tines 616 may differ shape, size, and/or configuration from other one(s) of the tines 616. In other words, in some instances, some of the tines 616 are different from other one(s) of the tines 616. In some instances, the tines 616 may be evenly spaced about the housing 612. Alternatively, the tines 616 may be unevenly spaced about the housing 612.

In some instances, a sleeve 618 may extend along the tines 616 and/or expandable conduit 614. Indeed, in some instances, the sleeve 618 may help to define the expandable conduit 614 (e.g., along with the tines 616). The sleeve 618 may extend along the outer surfaces of the tines 616. In some instances, the sleeve 618 may extend to the distal ends of the tines 616 and may be secured to the distal ends. In other instances, the sleeve 618 may wrap around the distal end of the tines 616 and along a portion of the inner surfaces of the tines 616. In these instances, the sleeve 618 may be secured to the inner surface of the tines 616.

In some instances, the sleeve 618 may be formed from or otherwise include an elastomeric material. For example, the sleeve 618 may include a silicone, a urethane, polytetrafluoroethylene, other materials such as those disclosed herein, and the like, and/or other suitable materials. In some instances, the sleeve 618 may be described as compliant and/or fully elastic. In such instances, the sleeve 618 may be described as being stretchable and able to recover/return to an original, unstressed shape when no longer exposed to stress forces. In other instances, the sleeve 618 may be described as being partially compliant and/or partially elastic. In such instances, the sleeve 618 may be able to stretch or partially stretch and, upon removal of stress forces, the sleeve 618 may partially recover an original, unstressed shape. In still other instances, the sleeve 618 may be described as being non-compliant and/or inelastic. In such instances, the sleeve 618 may be plastically deform when stressed beyond a pre-determined limit.

A plurality of adjustment mechanisms may be coupled to the housing 612 including a first adjustment mechanism 620 and a second adjustment mechanism 622. In some instances, the first adjustment mechanism 620 may take the form of a set screw that secures a stabilizing member 624 to the housing 612. The use of the set screws 620 may allow the stabilizing member 624 to be axially shifted (e.g., translated and/or otherwise raised or lowered) relative to the housing 612. Each of the stabilizing member 624 may be coupled to the housing with its own set screw 620 such that each stabilizing member 624 can be adjusted independently of one another. In this example, a plurality of stabilizing members 624 may be disposed about the housing 612. For example, one, two, three, four, five, six, or more stabilizing members 624 may be disposed about housing 612. The form of the stabilizing member 624 may vary. The stabilizing members 624 may take the form of arms. In some instances, the stabilizing members 624 may include a bend or elbow region. The stabilizing members 624 may also include a tissue contacting region. Other variations are contemplated. The stabilizing members 624 may be designed to contact a patient and help to stabilize the position of the expandable access port 610 relative to the patient.

In some instances, the second adjustment mechanism 622 may take the form of a set screw that is designed to adjust the position of one of the tines 616. The use of the set screws 622 may allow one of the tines 616 to be shifted/pivoted as described in more detail herein.

An actuation member 626 may be coupled to the housing 612. In general, the actuation member 626 may be used to shift the expandable conduit 614 and/or the tines 616 between the first configuration and the expanded configuration. In some instances, the actuation member 626 takes the form of a nut that is designed to threadably engage with the housing 612. Rotation of the actuation member 626 may shift the position (e.g., the axial position) of the actuation member 626 along the housing 612. This movement/translation may cause the actuation member 626 to interact with the tines 616 in a manner that cause the tines 616 to shift/pivot as described in more detail herein.

Other features of the expandable access port 610 are shown in FIG. 6A. For example, the housing 612 may include a proximal end region or flange 628. The housing 612 may have a proximal opening 630. The proximal opening 630 may be in fluid communication with the expandable conduit 614. In some instances, the proximal opening 630 may be shaped and/or configured to mechanically fit with another device designed to extend therethrough. For example, the proximal opening 630 may include one or more radial slots that allow another device to mechanically engage or "key" with the proximal end region 628.

A nose cone 632 may be disposed at the distal end of the expandable conduit 614. In general, the nose cone 632 may help form an atraumatic distal end for the expandable conduit 614. In some instances, the nose cone 632 may be coupled to one of the tines 616. In other instances, the nose cone 632 may be coupled to another portion of the expandable access port 610 or to another structure for use with the expandable access port 610. The nose cone 632 may have a tapered distal end region and/or a tapered proximal end region. Such a shape may allow the expandable access port 610 to be advanced into the anatomy in a manner that reduces trauma.

Figure 6B:
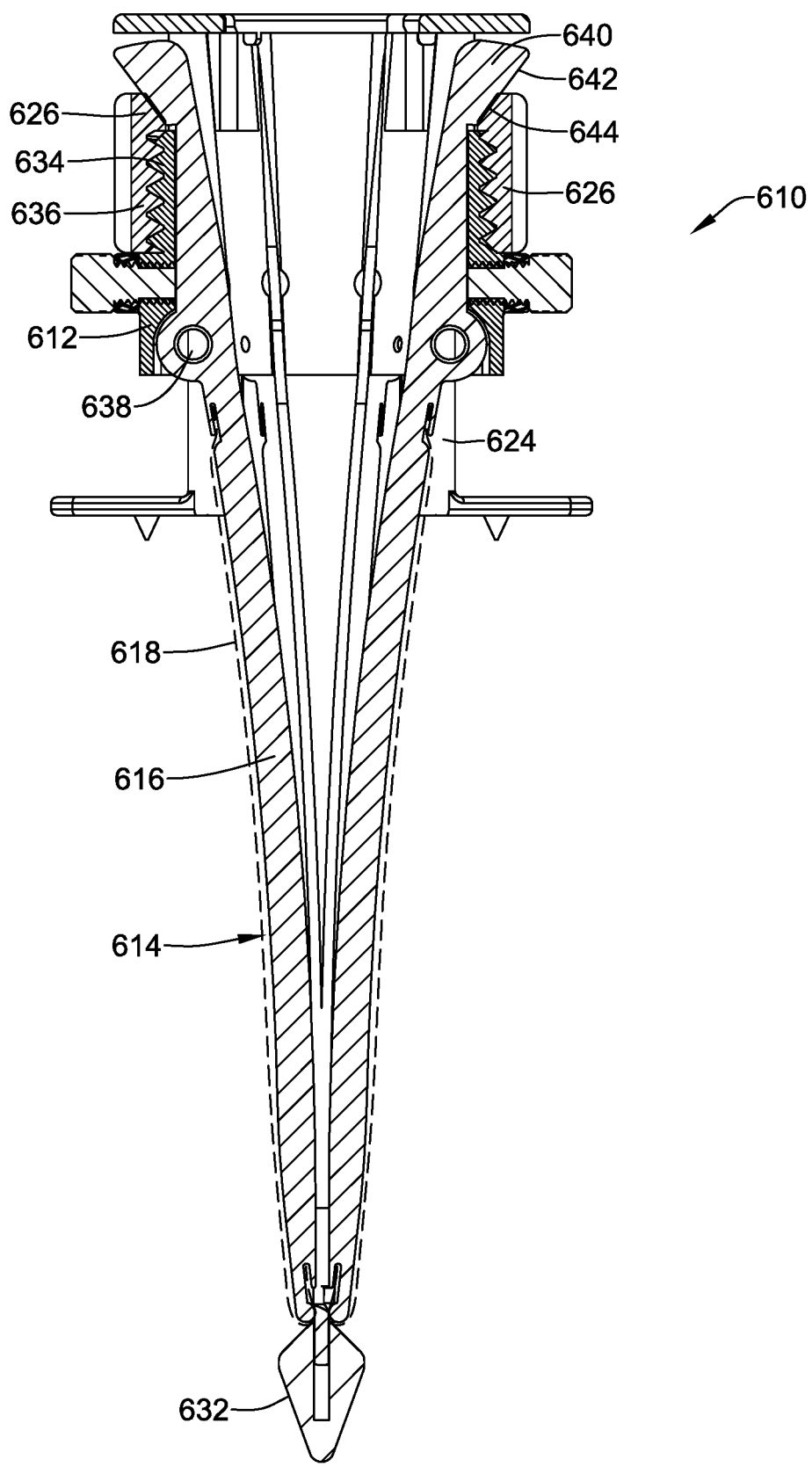
FIG. 6B is a cross-sectional view of an example expandable access port.

FIG. 6B is a cross-sectional view of the expandable access port 610. Here is can be seen that the housing 612 may include a threaded region 634. The actuation member 626 may include a corresponding threaded region 636 designed to engage the threaded region 634 of the housing 612.

Figure 6C:
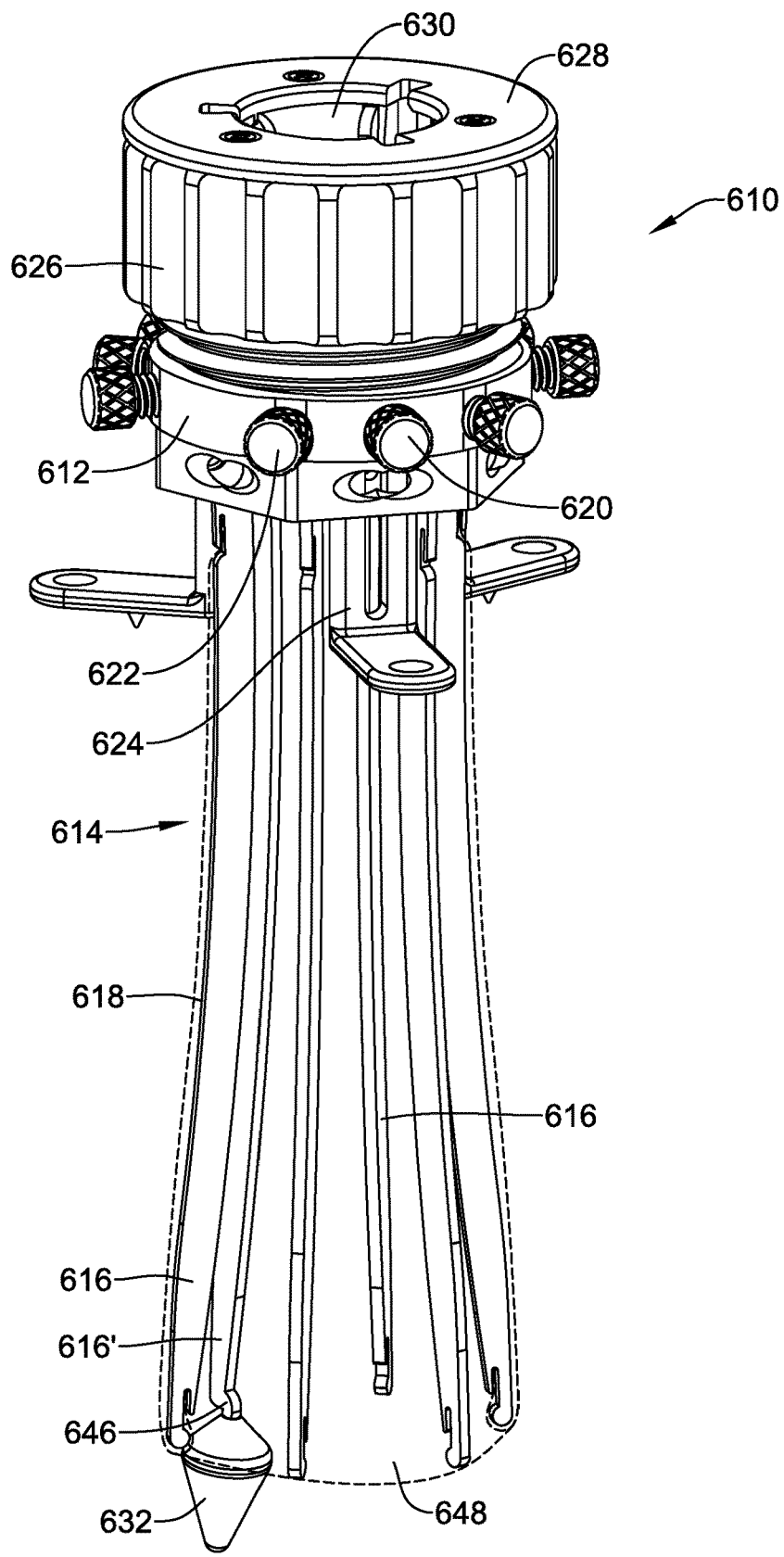
FIG. 6C is a perspective view of an example expandable access port.
Figure 6D:
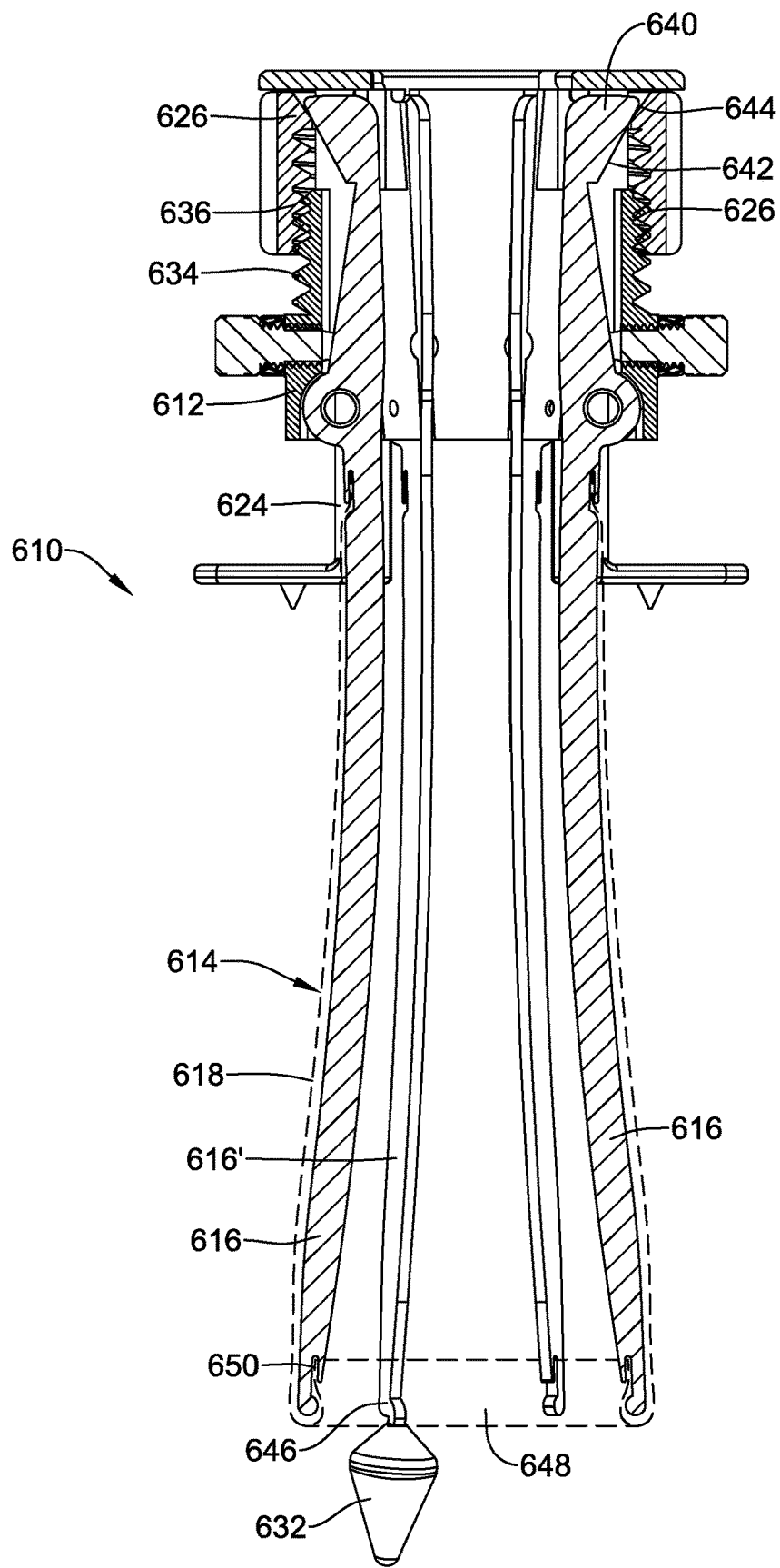
FIG. 6D is a cross-sectional view of an example expandable access port.

The plurality of tines 616 may be coupled to the housing 612 by a pivot member 638. In at least some instances, the pivot member 638 may take the form of a pivot pin. The pivot member 638 may allow the tines 616 to pivot in order to shift between the first configuration and the expanded configuration. In some instances, each of the plurality of tines 616 may have a proximal end region 640 having an angled surface 642. The actuation member 626 may have a corresponding angled surface 644 designed to engage the angled surface 642 of the proximal end region 640. Thus as the actuation member 626 is rotated and begins translating along the housing 612, the angle surface 644 of the actuation member 626 may engage the angled surface 642 of the proximal end region 640 of the tines 616. When doing so, the proximal end regions 640 of the tines 616 may be urged radially inward toward the housing 612. In some instances, the housing 612 may include a plurality of slots formed therein that allow the proximal end regions 640 of the tines 616 to move further radially inward. When the proximal end regions 640 of the tines 616 are urged radially inward, the distal end region may shift radially outward due to a pivoting action of the tines 616 about the pivot member 638 as depicted in FIGS. 6C-6D. In some instances, more or less expansion of each of the tines 616 can be accomplished independently using one of the second adjustment mechanisms (e.g., set screws) 622. When in the expanded configuration, the expandable conduit 614 may define a distal opening 648. In some instances, when the expandable conduit 614 is in the first configuration, the distal opening 648 may be the same size or smaller than the proximal opening 630. In some of these and in other instances, when the expandable conduit 614 is in the expanded configuration, the distal opening 648 may be the same size or larger than the proximal opening 630.

In some instances, the plurality of tines 616 may include a first tine 616'. The nose cone 632 may be coupled to the first tine 616'. For example, the first tine 616' may include a curved region 646 and the nose cone 632 may be coupled to the curved region 646. The first tine 616', thus, may differ in shape from at least one of the other tines 616. The arrangement of the nose cone 632 may be described as being aligned with a central and/or longitudinal axis of the housing 612 when the expandable conduit 614 is in the first configuration (e.g., as depicted in FIGS. 6A-6B). The nose cone 632 may be described as being offset (e.g., radially offset) from the central and/or longitudinal axis of the housing 612 when the expandable conduit 614 is in the expanded configuration (e.g., as depicted in FIGS. 6C-6D).

At least some of the tines 616 may include a gripping region 650. In general, the gripping region 650 may be designed to secure the sleeve 618 to the tines 616 and/or the expandable conduit 614. For example, the gripping region 650 may take the form of a slot or groove, into which the sleeve 618 can be inserted into. In some instances, the sheath 618 may be secured to the gripping regions 650 by crimping the gripping regions 650. In other instances, the sheath 618 may be secured to the tines 616, as desired, in another manner such as by adhesive bonding, thermal bonding, stitching, or the like.

Figure 6E:
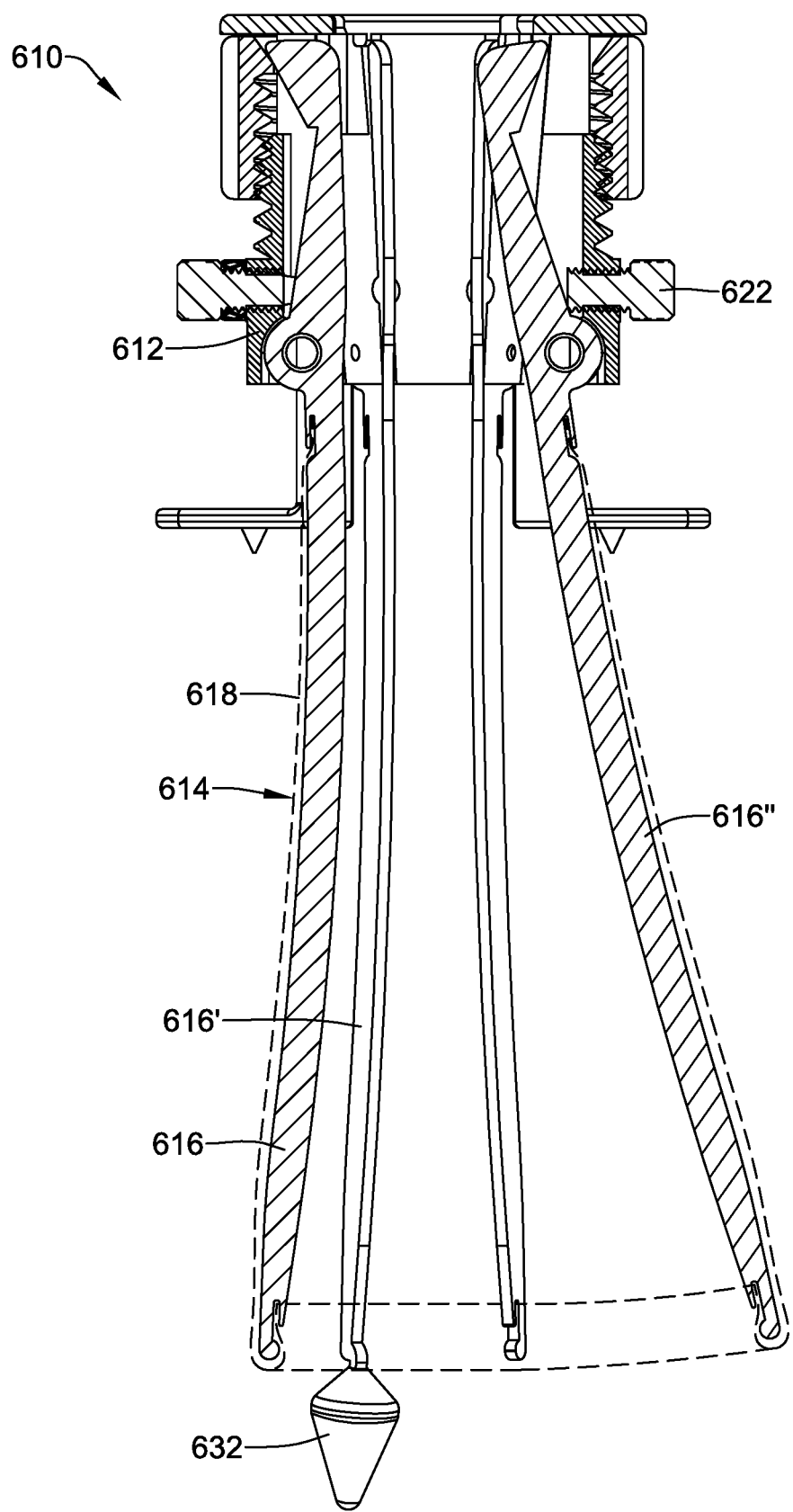
FIG. 6E is a cross-sectional view of an example expandable access port.

As indicated above, shifting the expandable conduit 614 and/or the tines 616 to or toward the expanded configuration may include actuating the actuation member 626. In addition, the second adjustment mechanism 622 can be utilized to independently adjust one of the tines 616. For example, FIG. 6E illustrates a configuration of the expandable conduit 614 where the second adjustment mechanism 622 (e.g., one of the set screws 622) is adjusted to further adjust (e.g., further expand) one of the tines 616".

Figure 6F:
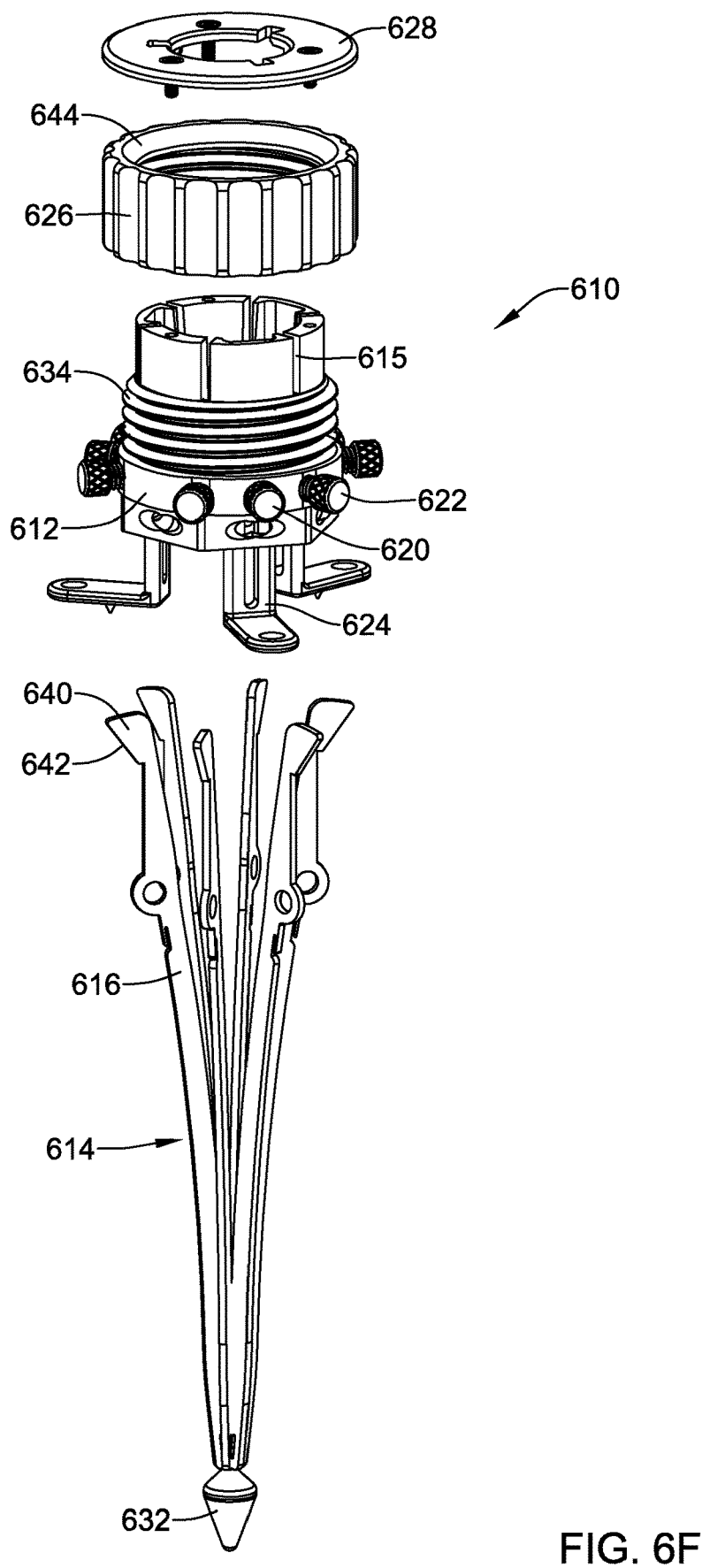
FIG. 6F is an exploded view of an example expandable access port.

FIG. 6F is an exploded view of the expandable access port 610. Here, a number of the structural features of the expandable access port 610 can be seen from a different perspective. For example, one or more slots 615 can be seen in the housing 612. The slots 615 may allow the proximal end regions 640 to shift further radially inward relative to the housing 612, for example when the actuation member 626 is rotated and translates along the housing 612.

Figure 7A:
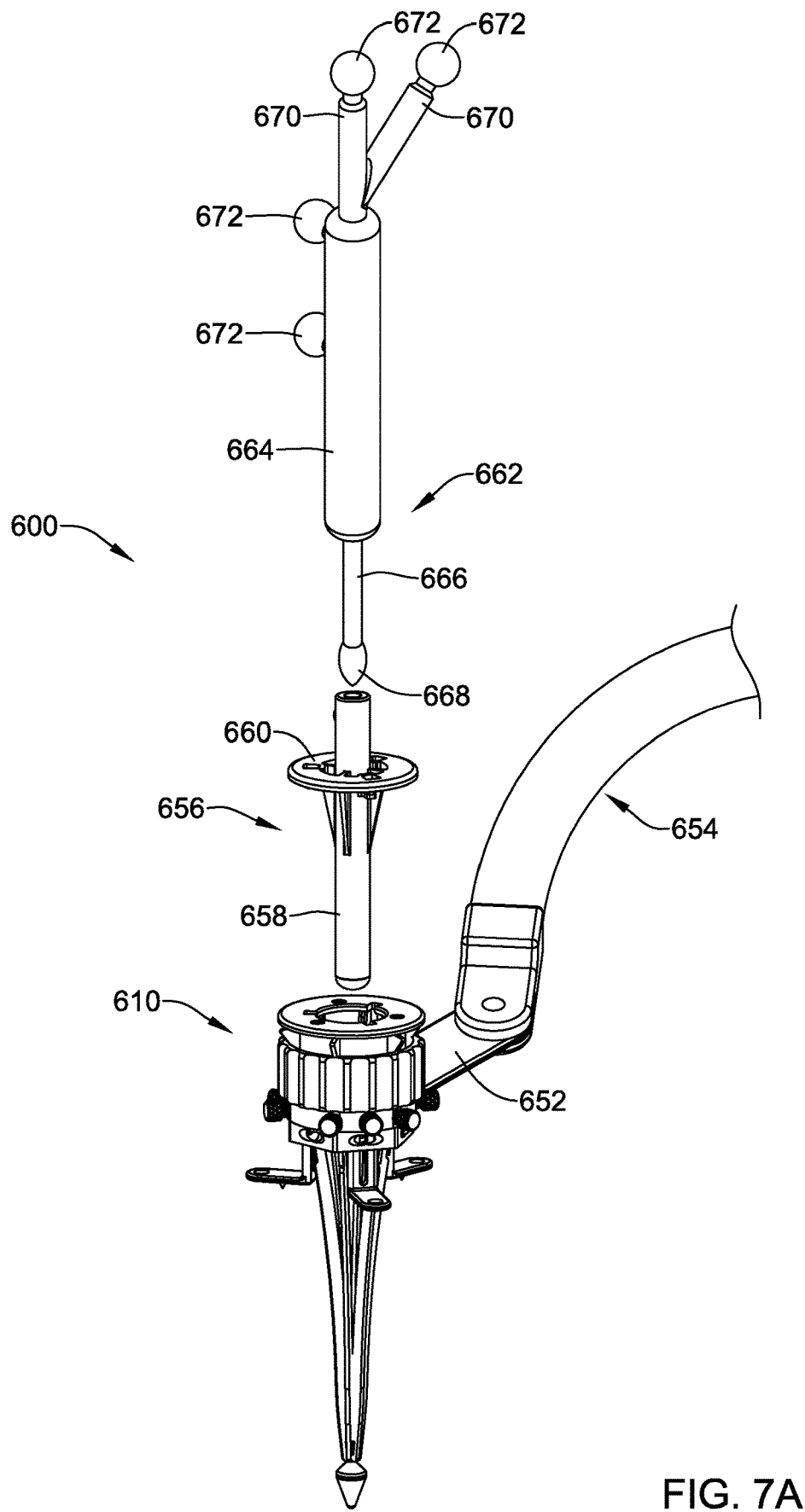
FIGS. 7A-7C illustrate a system for accessing the central nervous system.
Figure 7B:
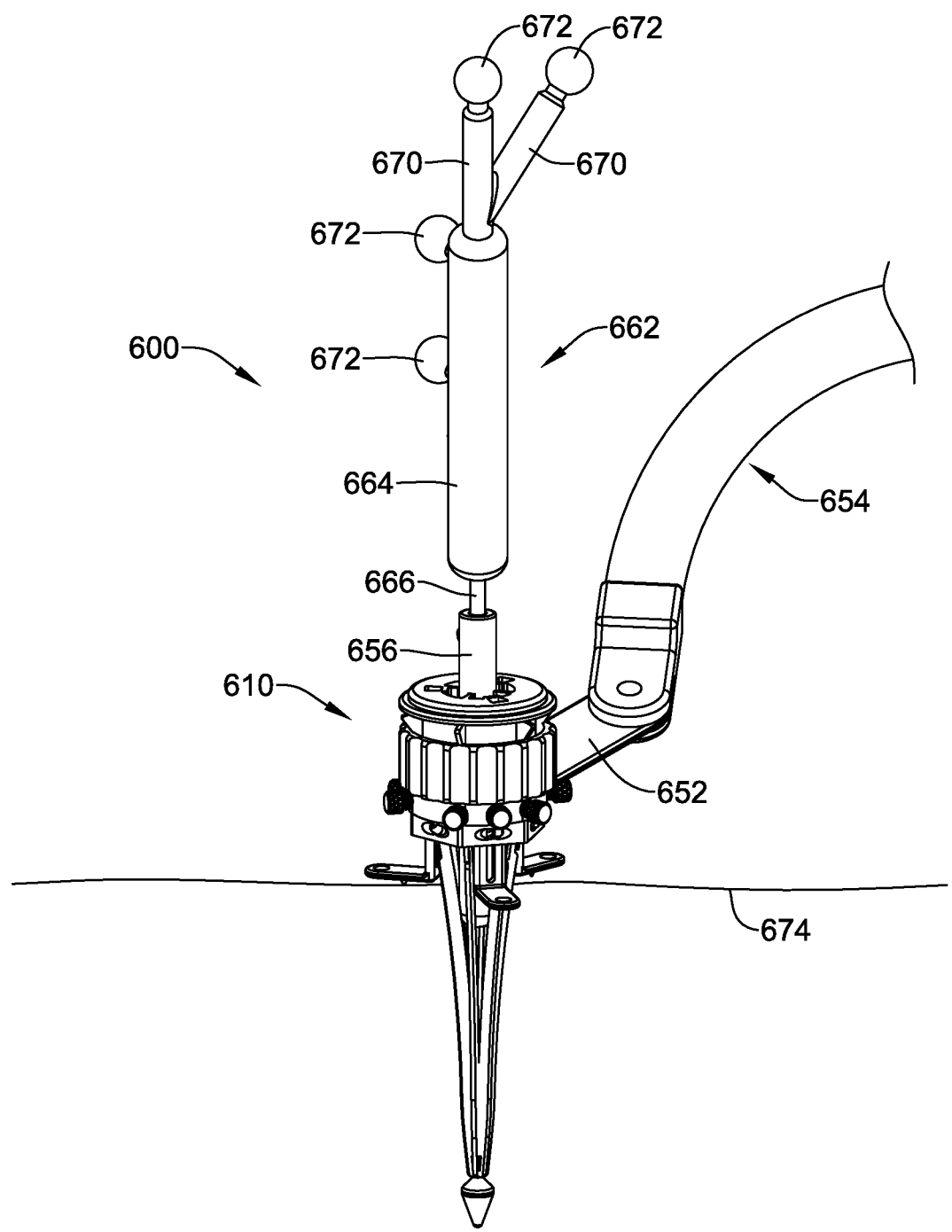
Figure 7C:
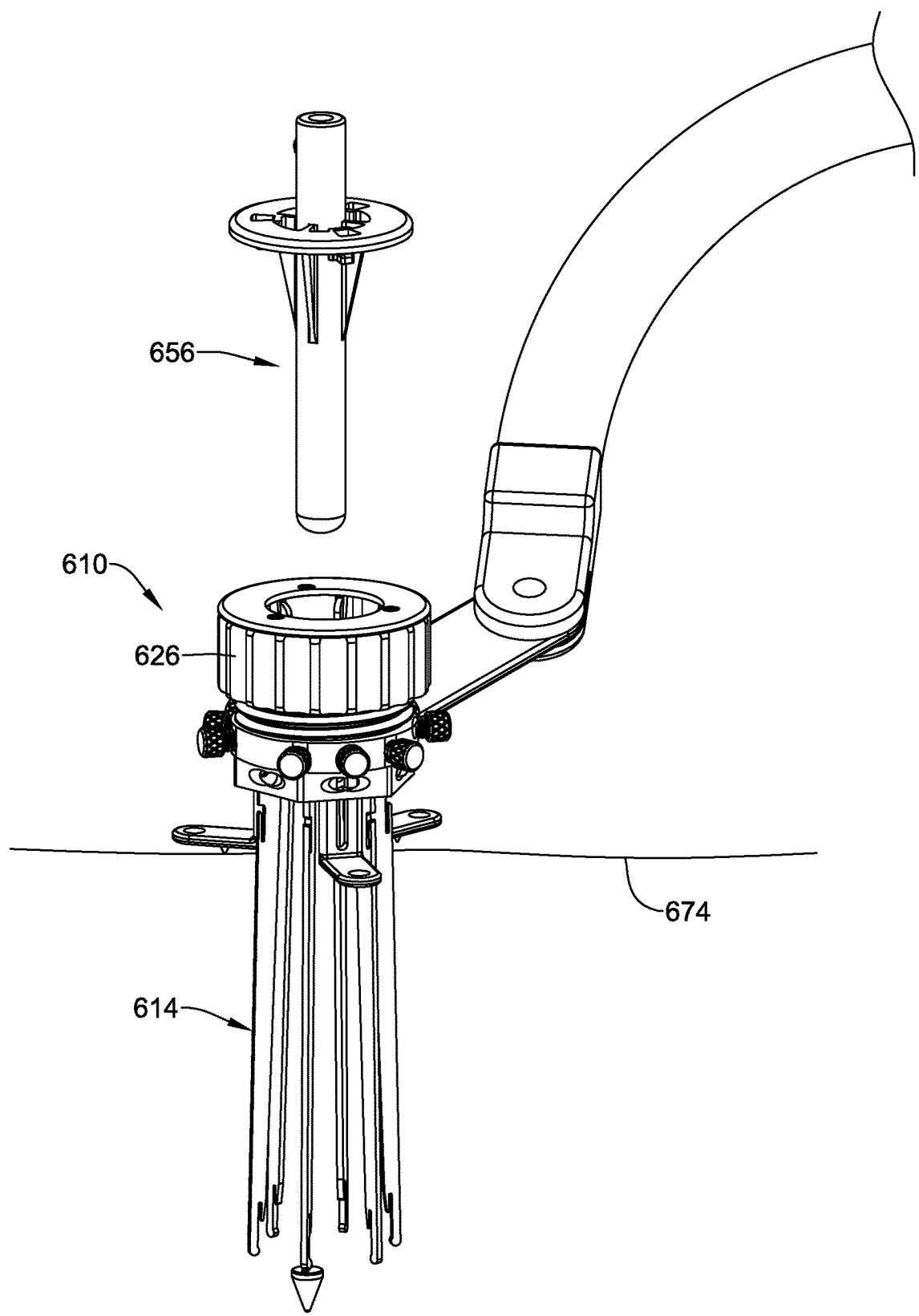

FIGS. 7A-7C illustrate a system for accessing the central nervous system 600. The system 600 may include the expandable access port 610 (e.g., as shown in FIGS. 6A-6F). In this example, the expandable access port 610 is shown with a stabilizing bar 652, which may be used to couple/secure the expandable access port 610 to a stabilizing system 654. Some example stabilizing systems that may be used with the stabilizing bar 652 may include those manufactured by INTEGRA, MIZUHO, TEDAN SURGICAL, as well as systems including GREENBERG, BUDDE, SUGITA, FUKUSHIMA, and the like. The stabilizing bar 652 may take the form of a rod or shaft that projects from the housing 612.

The system 600 may also include a holder 656. The holder 656 may include a tubular body 658 and a flange 660 disposed along the tubular body 658. In general, the flange 660 may be designed to engage the proximal end region 628 of the housing 612 and function as a stop that limits further movement of the holder 656 into the expandable access sheath 610.

In some instances, the system 600 may also include a visual navigation probe 662. The visual navigation probe 662 may include a base 664. A shaft 666 may extend from the base 664. The shaft 666 may include a tip 668. The tip 668 may be a rounded tip, an angled tip, or the like. One or more additional shafts 670 may extend from the base 664. The base 664 and/or the shafts 670 may include one or more visualization members 672.

The visual navigation probe 662 may be inserted into the holder 656 and the holder 656 may be inserted into the expandable access port 610. The system 600 may then be placed along a patient 674 and/or otherwise guided toward a target region as depicted in FIG. 7B. When suitably positioned, the holder 656 and the visual navigation probe 662 may be removed. The actuation member 626 may be actuated to shift the expandable conduit 614 to the expanded configuration as shown in FIG. 7C.

Figure 8A:
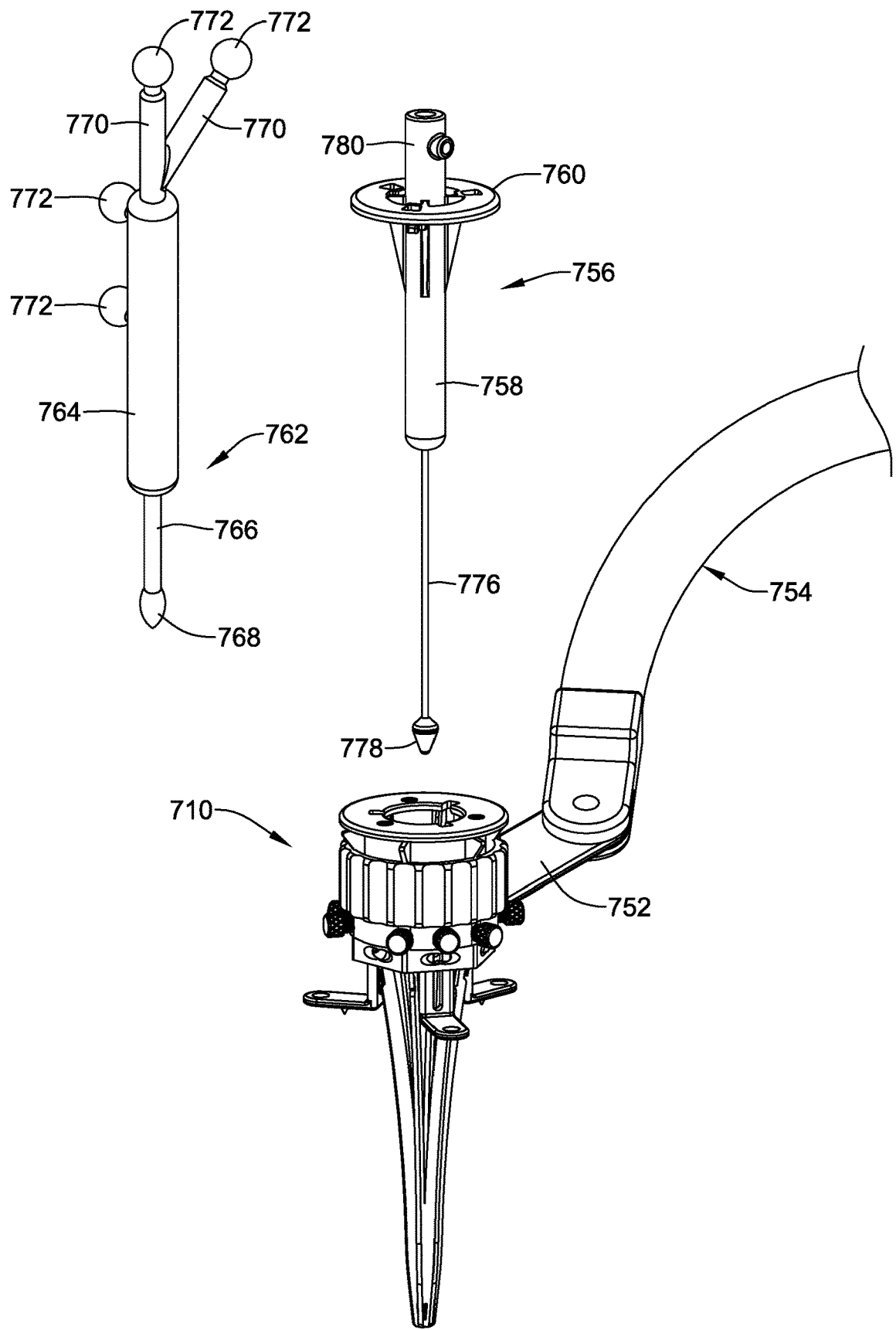
FIGS. 8A-8C illustrate a system for accessing the central nervous system.
Figure 8B:
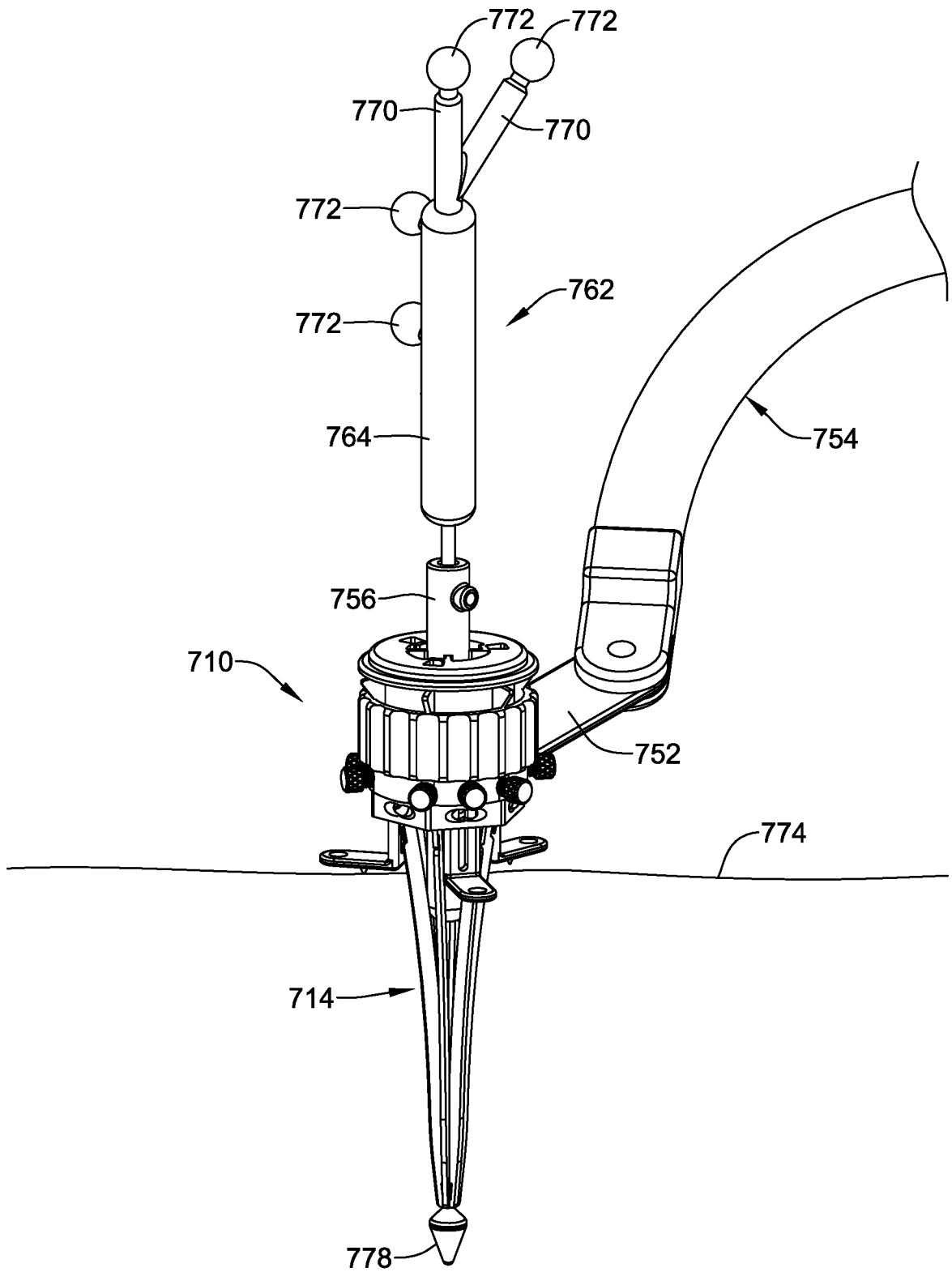
Figure 8C:
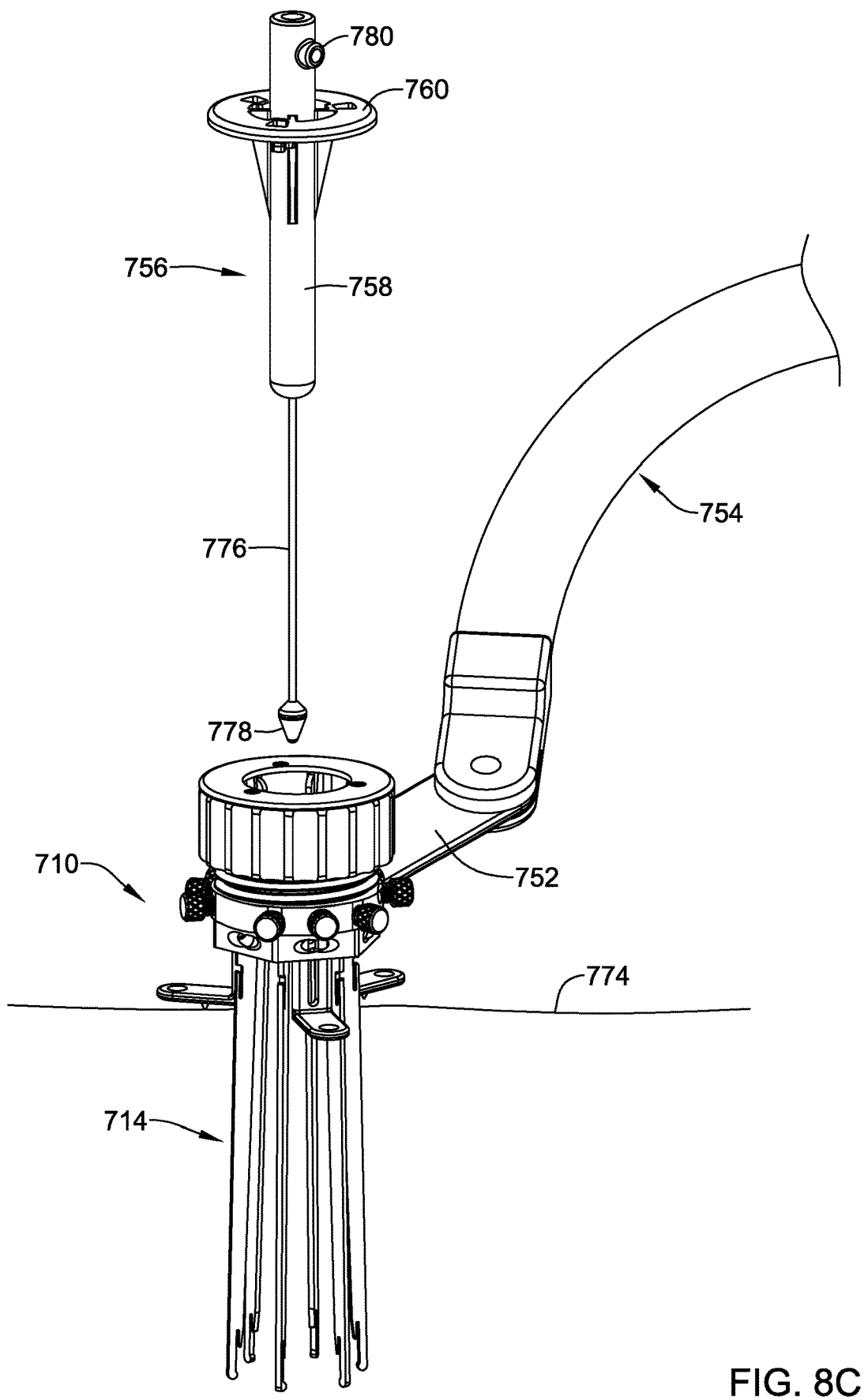

FIGS. 8A-8C illustrate a system for accessing the central nervous system 700. The system 700 may include an expandable access port 710. The expandable access port 710 may be similar in form and function to other access ports disclosed herein. In this example, the expandable access port 710 is shown with a stabilizing bar 752, which may be used to couple/secure the expandable access port 710 to a stabilizing system 754. Some example stabilizing systems that may be used with the stabilizing bar 752 may include those manufactured by INTEGRA, MIZUHO, TEDAN SURGICAL, as well as systems including GREENBERG, BUDDE, SUGITA, FUKUSHIMA, and the like. Also, in this example, the expandable access port 710 may be free from a nose cone. Some additional discussion pertaining to the expandable access port 710 can be found herein with reference to FIG. 9.

The system 700 may also include a holder 756. The holder 756 may include a tubular body 758 and a flange 760 disposed along the tubular body 758. In some instances, set screw 780 may be disposed along the tubular body 758. As indicated above, the expandable access port 710 may lack a nose cone. In this case, the holder 756 may include a shaft 776 extending from the tubular body 758 and a nose cone 778 may be coupled to the shaft 776. The shaft 776 and the nose cone 778 may be designed so that the holder 756 can be inserted into the expandable access port 710 and, when fully inserted, the nose cone 778 may be disposed at the distal end of the expandable access sheath 710. In some instances, the nose cone 778 may have a generally atraumatic shape. For example, the nose cone 778 may include a tapered proximal end region and/or a tapered distal end region. This may allow the nose cone 778 to more easily be inserted into and through the expandable access sheath 710 and/or more easily removed from the expandable access sheath 710. When doing so, the expandable access sheath 710 may partially expand or flex while allowing the nose cone 778 to pass therethrough. Furthermore, the nose cone 778 (and/or the holder 756, in general) can be inserted into or removed from the expandable access sheath 710 without having to shift the expandable conduit 714 to the expanded configuration.

The system 700 may also include a visual navigation probe 762. The visual navigation probe 762 may include a base 764. A shaft 766 may extend from the base 764. The shaft 766 may include a tip 768. One or more additional shafts 770 may extend from the base 764. The base 764 and/or the shafts 770 may include one or more visualization members 772. The visual navigation probe 762 may be inserted into the holder 756 and the holder 756 may be inserted into the expandable access port 710. The system 700 may then be placed along a patient 774 and/or otherwise navigated toward a target region as shown in FIG. 8B. The holder 756 and the visual navigation probe 762 may be removed. The actuation member 726 may be actuated to shift the expandable conduit 714 to the expanded configuration as shown in FIG. 8C.

Figure 9:
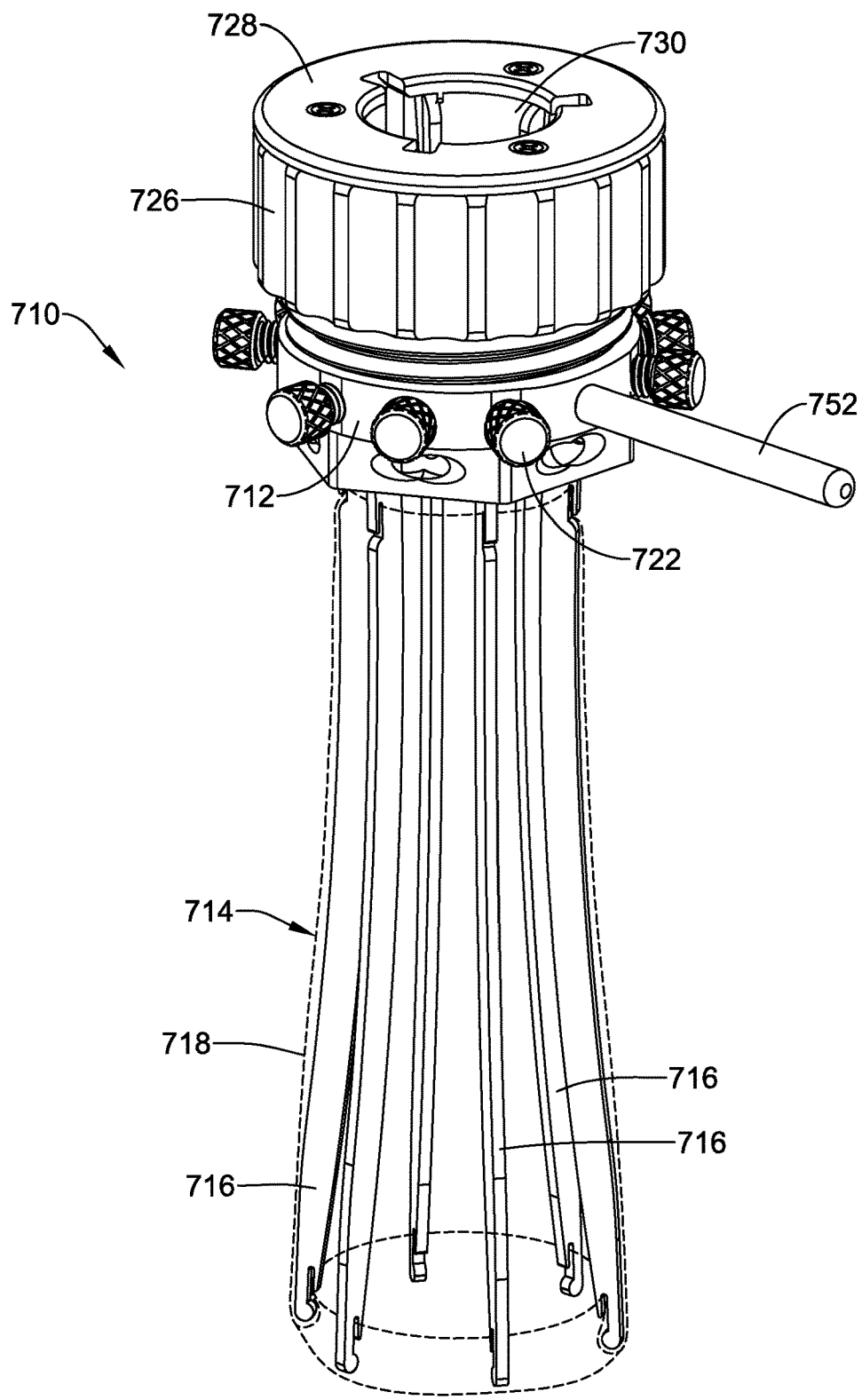
FIG. 9 is a perspective view of an example expandable access port.

FIG. 9 illustrates the expandable access port 710. The expandable access port 710 may include a number of the structural features of the expandable access port 610. For example, the expandable access port 710 may include a housing 712 and an expandable conduit 714 coupled to the housing 712. The expandable conduit 714 may include a plurality of tines 716. A sleeve 718 may be disposed along the tines 716. The housing 712 may include a flanged region 728 and a distal opening 730. An actuation member 726 may be coupled to the housing 712 and may function similarly to the actuation member 626. An adjustment mechanism 722 may be coupled to the housing 712.

As indicated above, the expandable access port 710 may lack a nose cone and, in at least some instances, may be used with another device such as the holder 756 (e.g., which include a nose cone 778). Because the expandable access port 710 may lack a nose cone, all of the tines 716 may be substantially similar. Alternatively, one or more of the tines 716 may differ from other one(s) of the tines 716.

In some instances, the housing may lack the first adjustment mechanisms (e.g., set screws 620) coupled to stabilizing members (e.g., stabilizing members 624) and/or lack stabilizing members resembling the stabilizing members 624. Instead, a stabilizing bar 752 may be coupled to the housing 712 and project radially therefrom. The stabilizing bar 752 may be used to secure the expandable access port 710 to a stabilizing system. Some example stabilizing systems that may be used with the stabilizing bar 752 may include those manufactured by INTEGRA, MIZUHO, TEDAN SURGICAL, as well as systems including GREENBERG, BUDDE, SUGITA, FUKUSHIMA, and the like. The form of the stabilizing bar 752 may vary. In some instances, a stabilizing bar similar to the stabilizing bar 752 may be utilized with the expandable access port 610.

Figure 10:
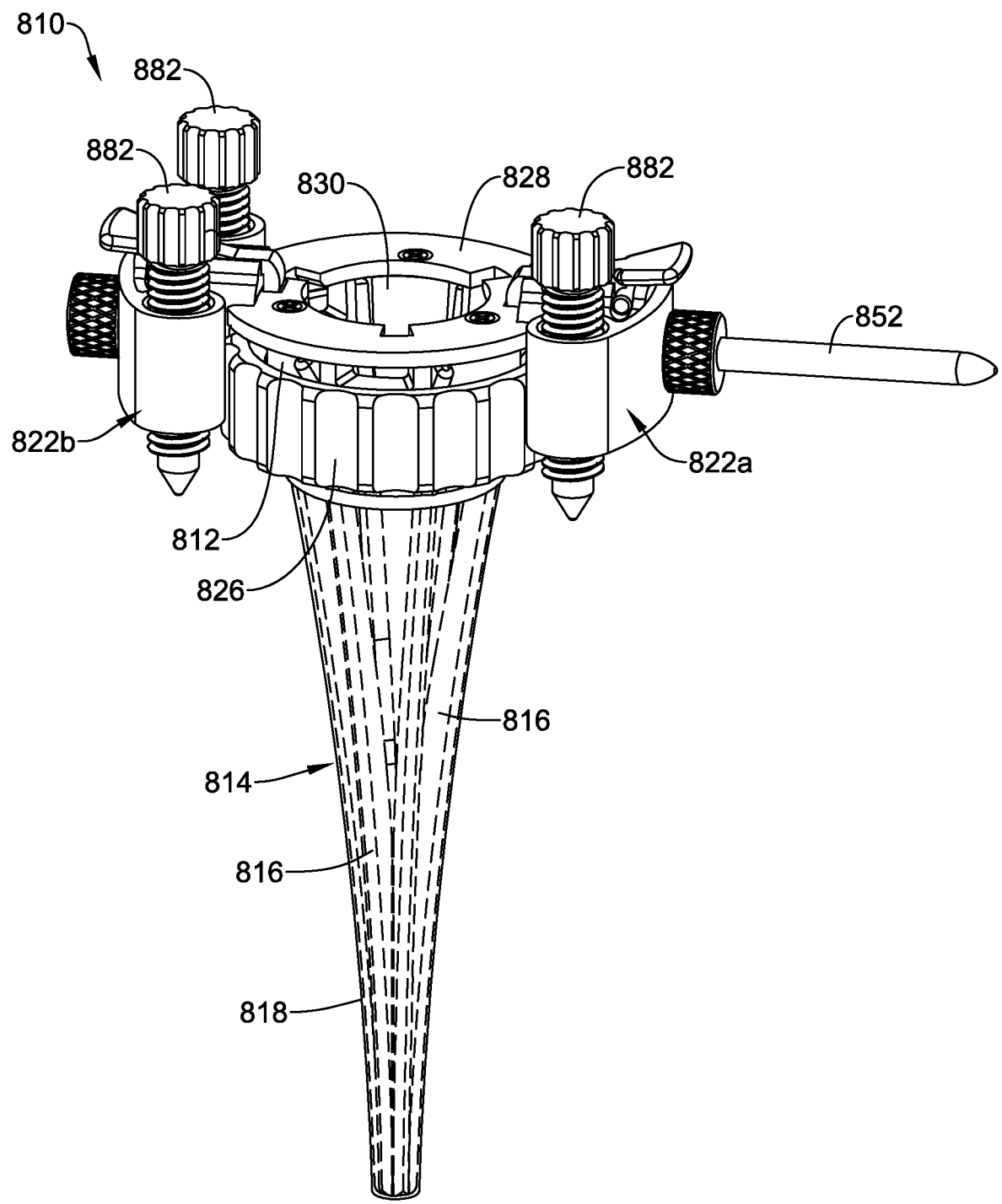
FIGS. 10-15 illustrate an example expandable access port.
Figure 11:
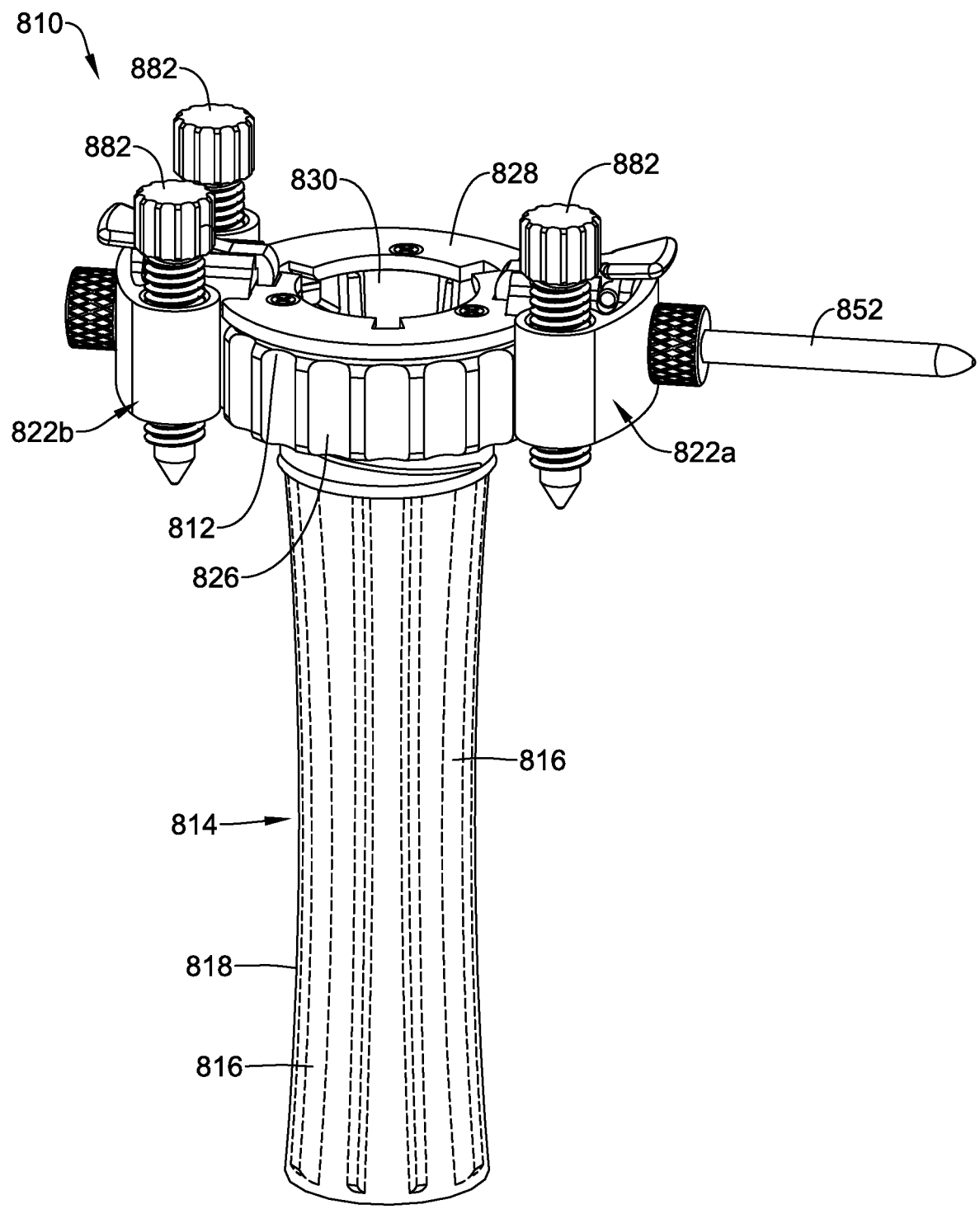

FIGS. 10-15 illustrate an expandable access port 810 (e.g., the expandable access port 810 may also be described as an expandable access sheath 810) that may be similar in form and function to other access ports/sheaths disclosed herein. The expandable access port 810 may include a housing 812 and an expandable conduit 814 coupled to the housing 812. The expandable conduit 814 may include a plurality of tines 816. A sleeve 818 may be disposed along the tines 816. The housing 812 may include a cap 828 and a distal opening 830. An actuation member 826 may be coupled to the housing 812 and may function similarly to other actuation members disclosed herein in order to shift the expandable conduit between a first configuration (e.g., as shown in FIG. 10) and a second or expanded configuration (e.g., as shown in FIG. 11).

One or more adjustment mechanisms, for example a first adjustment mechanism 822a and a second adjustment mechanism 822b, may be coupled to the cap 828. The form of the first adjustment mechanism 822a, the second adjustment mechanism 822b, or both may vary. For example, in some instances the first adjustment mechanism 822a may include a threaded leg 882 that may be used to adjust the position of the expandable access port 810 relative to the patient. The first adjustment mechanism 822a may also include a stabilizing bar 852, which may be used to couple/ secure the expandable access port 810 to a stabilizing system (not shown). Some example stabilizing systems that may be used with the stabilizing bar 852 may include those manufactured by INTEGRA, MIZUHO, TEDAN SURGICAL, as well as systems including GREENBERG, BUDDE, SUGITA, FUKUSHIMA, and the like. The second adjustment mechanism 822b may include one or more threaded legs 882 that may be used to adjust the position of the expandable access port 810 relative to the patient. Other adjustment mechanisms are contemplated that include a single threaded leg 882, two or more threaded legs 882, lack a threaded leg 882, a single stabilizing bar 852, two more stabilizing bars 852, lack a stabilizing bar 852, and the like.

Figure 12:
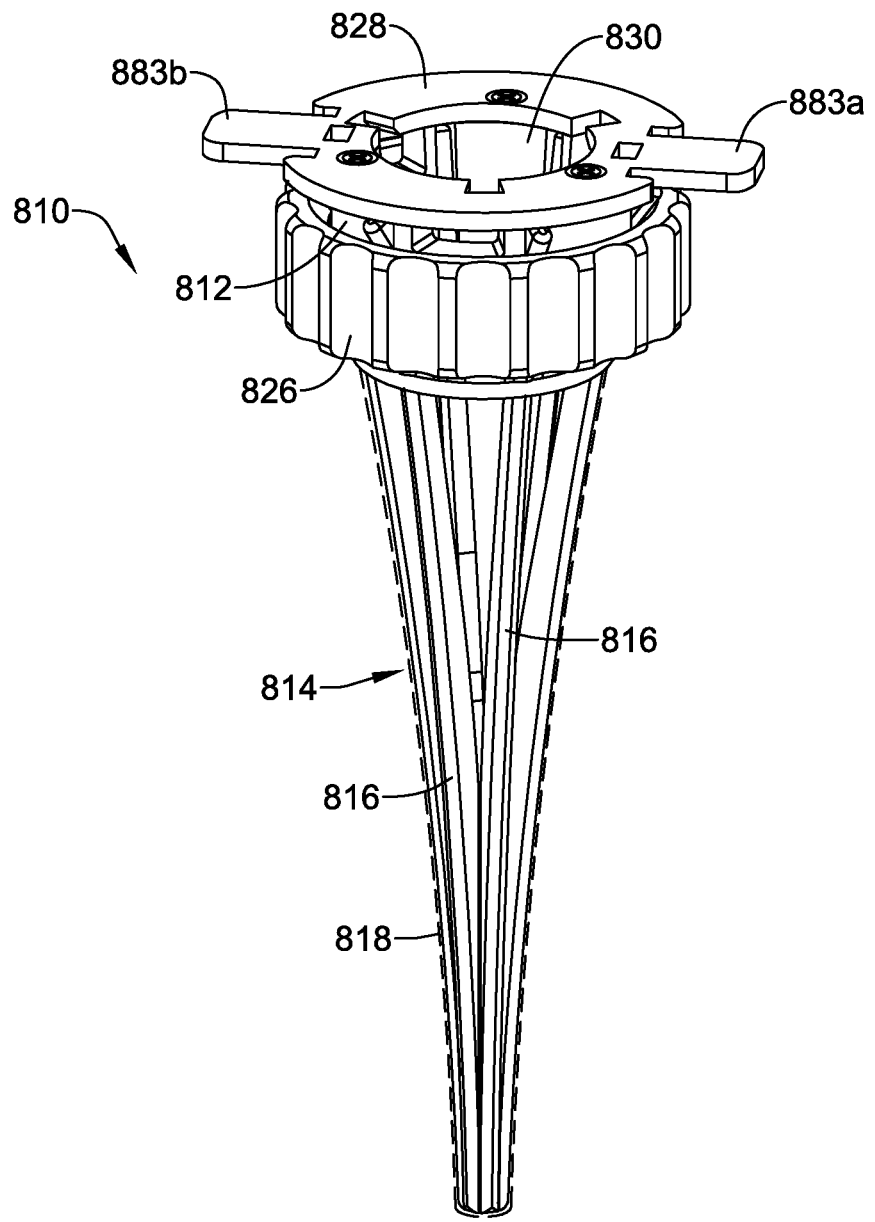
Figure 13:
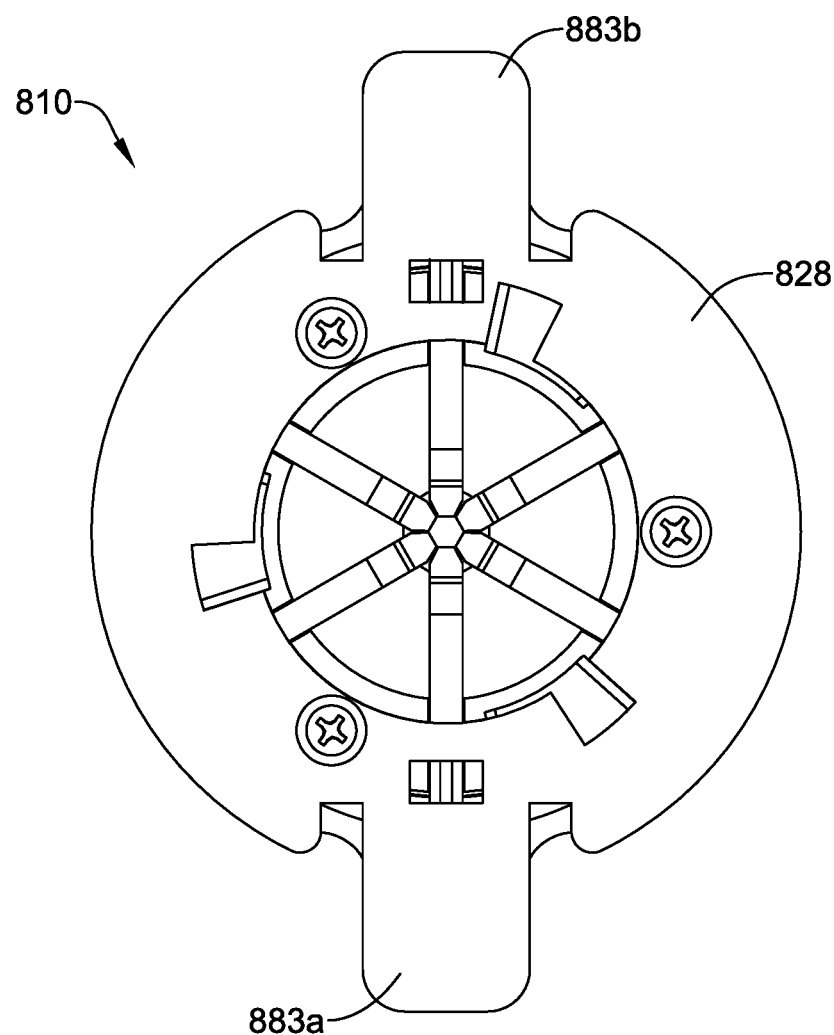
Figure 14A:
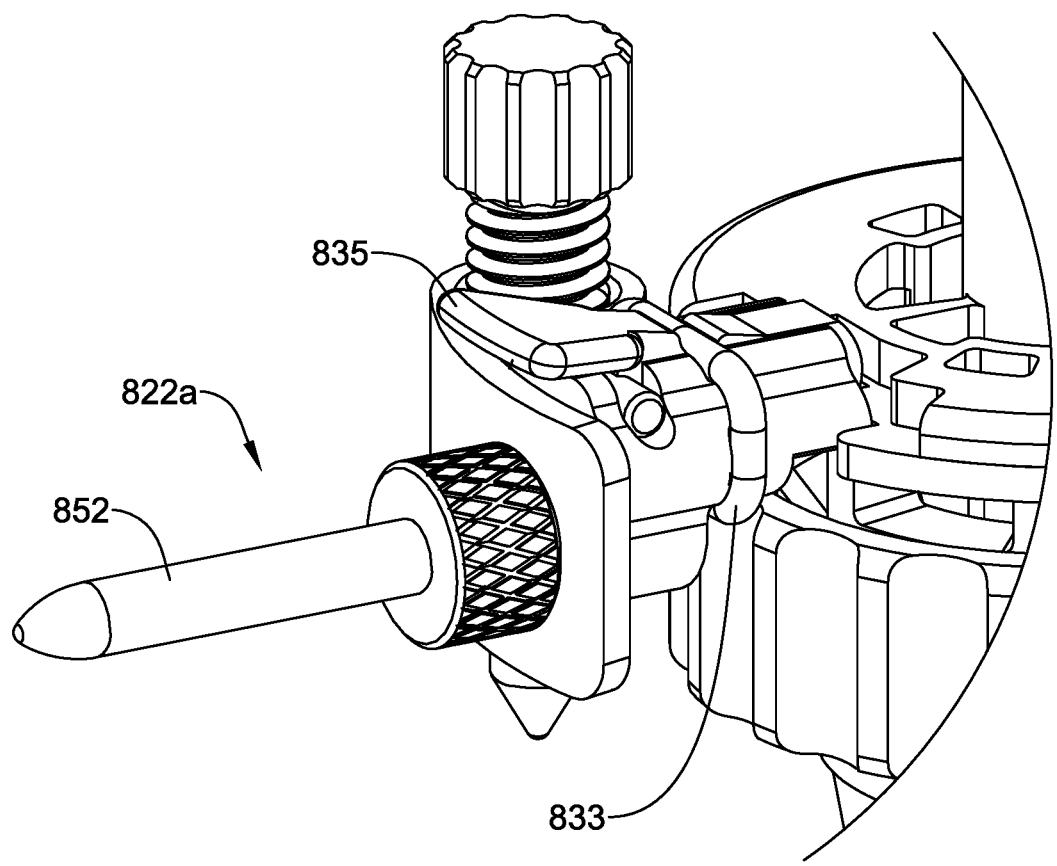

FIGS. 12-13 illustrates the expandable access port 810 with the first adjustment mechanism 822a and the second adjustment mechanism 822b detached from the cap 828. Here it can be seen that the cap 828 may include a first attachment region 883a and a second attachment region 883b. In at least some instances, the first attachment region 883a and the second attachment region 883b allow for a variety of adjustment mechanisms to be releasably coupled thereto. For example, the first attachment region 883a and/or the second attachment region 883b may take the form of a flange designed to have an adjustment mechanism (e.g., the first adjustment mechanism 822a, the second adjustment mechanism 822b, or both) releasably attached to the cap 828. The adjustment mechanisms 822a/822b may include spring-release attachment/detachment mechanism including a spring or elastic member 833 and a lever member 835 as shown in FIG. 14A. In some instances, the elastic member 833 takes the form of an O-ring that is used as or like a spring to hold down the lever member 835 (e.g., so that adjustment mechanisms 822a/822b can be securely attached to the attachment regions 883a/883b). The lever member 835 can be depressed to enlarge or otherwise expand the elastic member 833. This allows the adjustment mechanisms 822a/822b to easily be securely attached/detached from the attachment regions 883a/883b, as desired.

Figure 14:
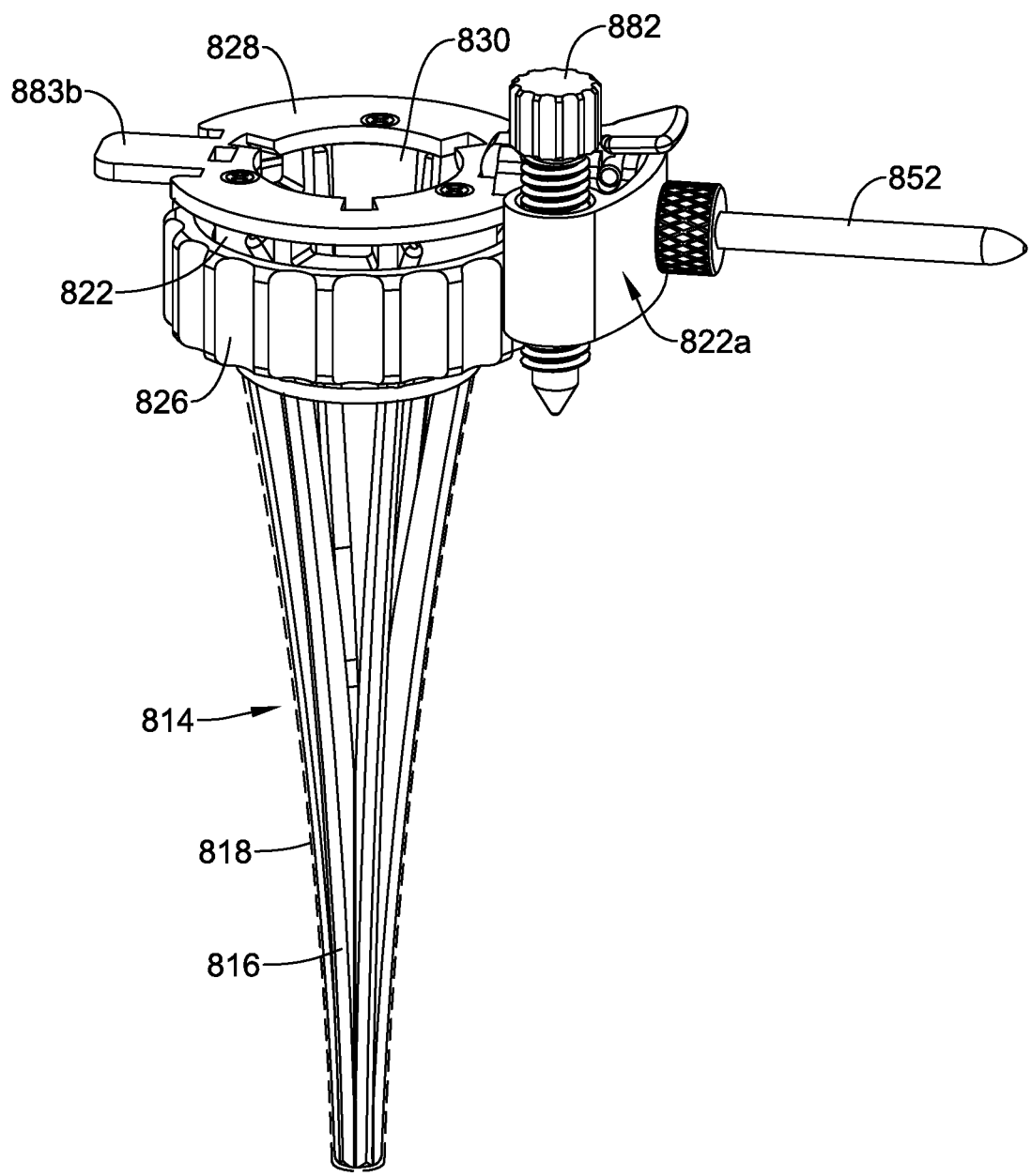
Figure 15:
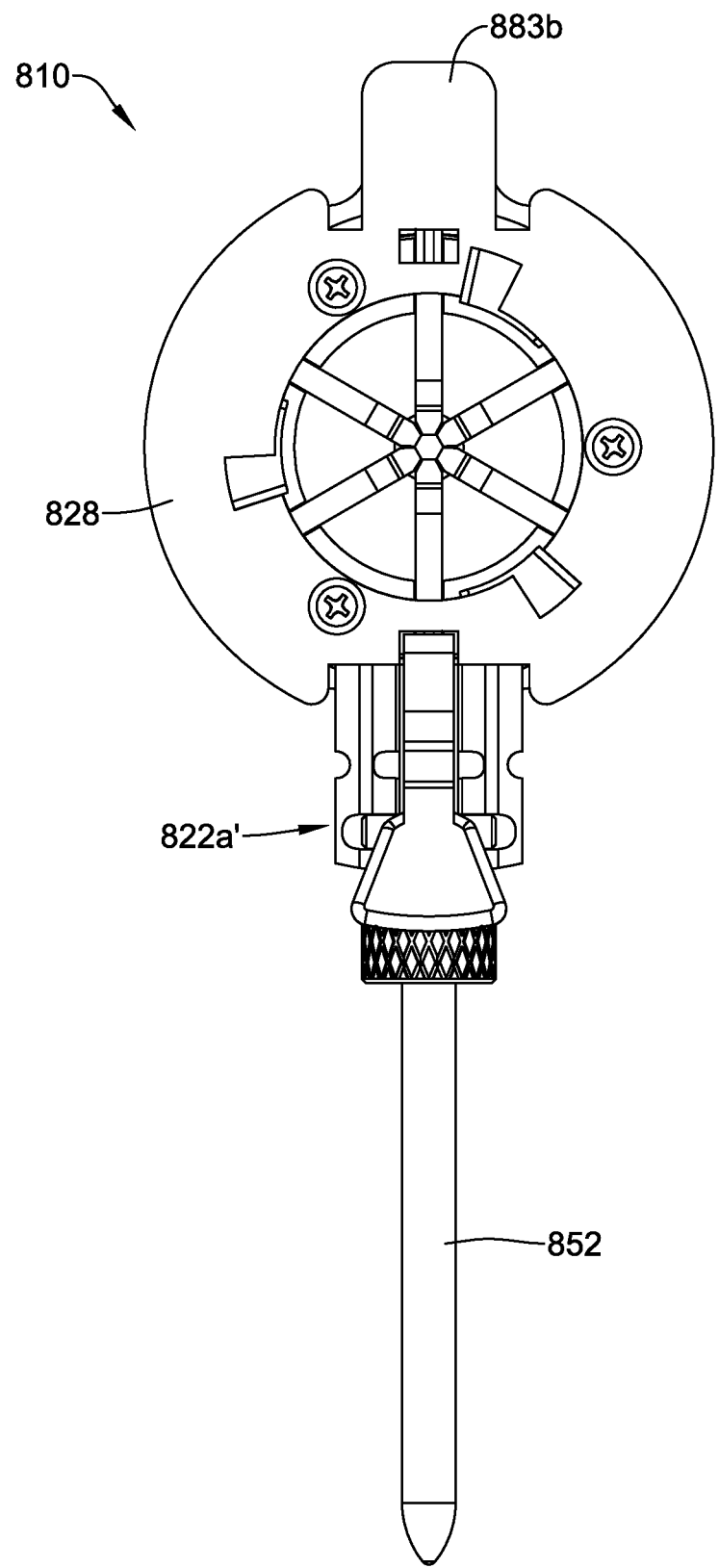

In use, a clinician may choose to attach a suitable number of adjustment mechanisms to the cap 828 (e.g., the first attachment region 883a and/or the second attachment region 883b). The form or type of adjustment mechanism may vary and, in at least some instances, the type of adjustment mechanism may be selected in order to best suit the needs of a particular intervention. For example, the first adjustment mechanism 822a may be attached to the first attachment region 883a as shown in FIG. 14. In this example, an adjustment mechanism is not attached to the second attachment region 883b. Further illustrating the variability of the adjustment mechanisms contemplated, FIG. 15 illustrates another adjustment mechanism 822a' attached to the cap 828 (e.g., the first attachment region 883a) of the expandable access port 810. In this example, the adjustment mechanism 822a' includes the stabilizing bar 852 but does not include a set screw. Other variations are contemplated.

Figure 16:
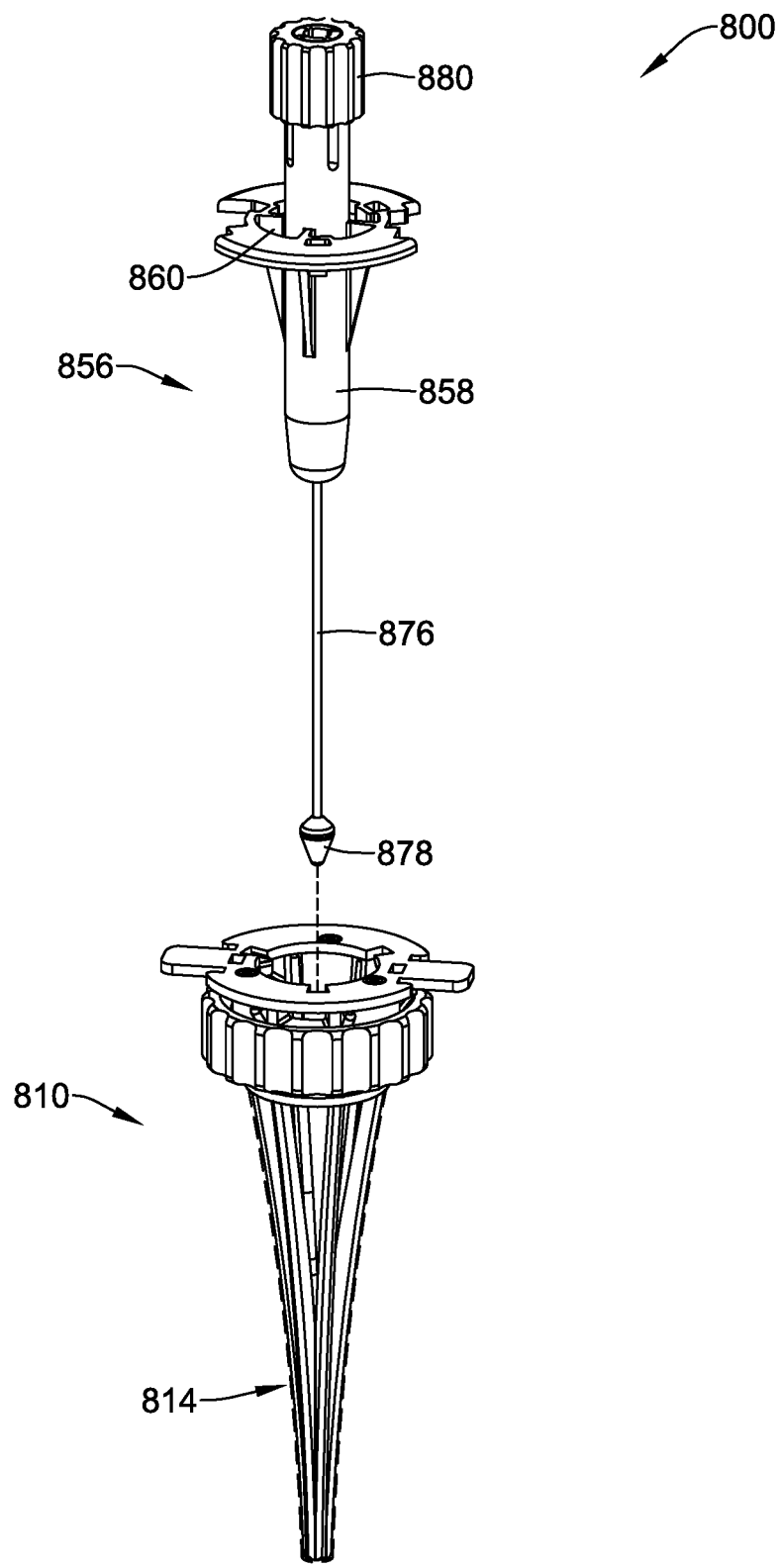
FIGS. 16-17 illustrate a system for accessing the central nervous system.
Figure 17:
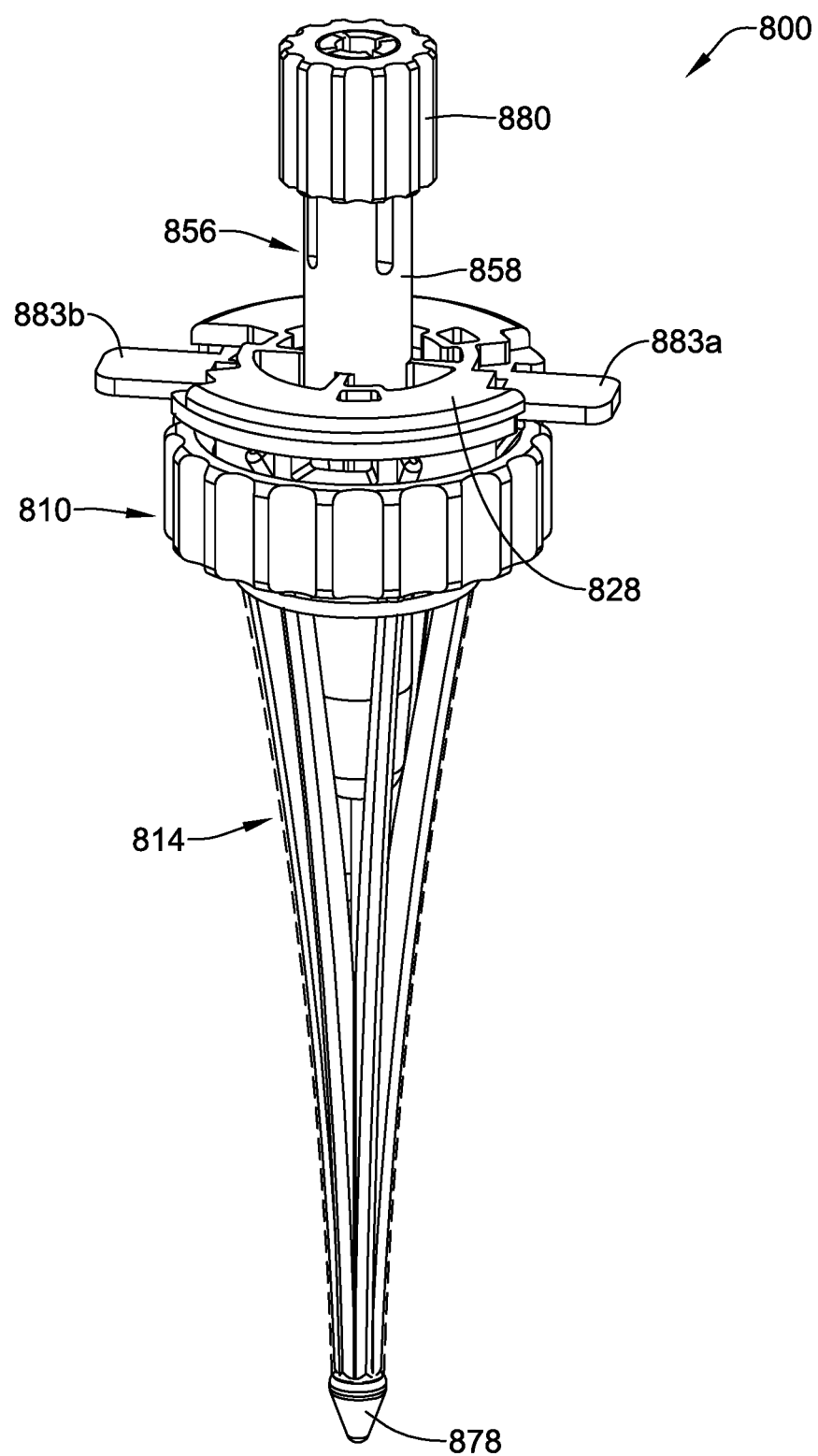

FIGS. 16-17 illustrates a system 800 that include the expandable access port 810 along with a holder 856. The holder 856 may include a tubular body 858 and a flange 860 disposed along the tubular body 858. In some instances, a nut or grip region 880 may be disposed along the tubular body 858. The holder 856 may include a shaft 876 extending from the tubular body 858 and a nose cone 878 may be coupled to the shaft 876. The shaft 876 and the nose cone 878 may be designed so that the holder 856 can be inserted into the expandable access port 810 and, when fully inserted, the nose cone 878 may be disposed at the distal end of the expandable access port 810. In some instances, the nose cone 878 may have a generally atraumatic shape. For example, the nose cone 878 may include a tapered proximal end region and/or a tapered distal end region. This may allow the nose cone 878 to more easily be inserted into and through the expandable access port 810 and/or more easily removed from the expandable access port 810. When doing so, the expandable access port 810 may partially expand or flex while allowing the nose cone 878 to pass therethrough. Furthermore, the nose cone 878 (and/or the holder 856, in general) can be inserted into or removed from the expandable access port 810 without having to shift the expandable conduit 814 to the expanded configuration.

The materials that can be used for the various components of the medical device 10 (and/or other medical devices/ system disclosed herein) may include those commonly associated with medical devices. For simplicity purposes, the following discussion makes reference to the medical device 10. However, this is not intended to limit the devices and methods described herein, as the discussion may be applied to other similar medical devices and/or system disclosed herein.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (Mill) compatibility is imparted into the medical device 10. For example, the medical device 10, or portions thereof, may be made of a material that does not substantially distort the image and create substantial artifacts (e.g., gaps in the image). Certain ferromagnetic materials, for example, may not be suitable because they may create artifacts in an MRI image. The medical device 10, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A system for accessing a central nervous system, the system comprising:
    an expandable access port, the expandable access port comprising:
        a housing having an expandable conduit coupled thereto and having a threaded region with an external thread disposed along an exterior surface of the threaded region, the expandable conduit including a plurality of tines, the plurality of tines including a first tine,
        a planar cap coupled to the housing, the planar cap comprising a rounded base and one or more attachment regions projecting laterally outward from the rounded base, the one or more attachment regions each including two substantially parallel side surfaces that extend radially outward relative to the rounded base and an end surface at an end region of the two substantially parallel side surfaces,
        an adjustment mechanism releasably coupled to one of the one or more attachment regions, the adjustment mechanism including an elastic member and a lever member for releasably coupling the adjustment mechanism directly to one of the one or more attachment regions; and
        an actuation member threadably engaged with the external thread, the actuation member being designed to shift the expandable conduit between a first configuration and an expanded configuration by rotating the actuation member about the exterior surface of the threaded region; and
    a holder designed to extend at least partially through the expandable conduit, the holder comprising:
        a tubular base,
        a shaft extending from the tubular base, and
        a nose cone attached to the shaft.

2. The system of claim 1, wherein the actuation member includes a nut threadably engaged with the threaded region.

3. The system of claim 1, wherein the first tine is secured to the housing with a pivot member and wherein the pivot member includes a pivot pin.

4. The system of claim 1, wherein the first tine includes a proximal end region with an angled surface and wherein the actuation member includes an actuation surface designed to engage the angled surface.

5. The system of claim 1, wherein the expandable conduit includes a sleeve extending along at least some of the plurality of tines.

6. The system of claim 1, wherein the housing defines a central axis and wherein the nose cone is aligned with the central axis when the plurality of tines are in the first configuration.

7. The system of claim 1, further comprising one or more stabilization members coupled to the housing.

* * * * *